US008410178B2

(12) United States Patent
Carroll et al.

(10) Patent No.: US 8,410,178 B2
(45) Date of Patent: *Apr. 2, 2013

(54) CIS 3,4-DIHYDROXY-2-(3-METHYLBUTANOYL)-5-(3-METHYLBUTYL)-4-(4-METHYLPENTANOYL)CYCLOPENT-2-EN-1-DERIVATIVES, SUBSTANTIALLY ENANTIOMERICALLY PURE COMPOSITIONS AND METHODS

(75) Inventors: Brian J. Carroll, Gig Harbor, WA (US); Gary Darland, Gig Harbor, WA (US); Anuradha Desai, Gig Harbor, WA (US); Veera Konda, Gig Harbor, WA (US); Clinton J. Dahlberg, Port Orchard, WA (US); Jan Urban, Gig Harbor, WA (US)

(73) Assignee: KinDex Therapeutics, LLC, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/284,852

(22) Filed: Oct. 28, 2011

(65) Prior Publication Data

US 2012/0108671 A1    May 3, 2012

Related U.S. Application Data

(60) Provisional application No. 61/408,572, filed on Oct. 30, 2010, provisional application No. 61/448,150, filed on Mar. 1, 2011, provisional application No. 61/508,434, filed on Jul. 15, 2011.

(51) Int. Cl.
*A61K 31/12* (2006.01)
*C07C 49/00* (2006.01)
(52) U.S. Cl. ........................ 514/690; 568/379
(58) Field of Classification Search .................. 568/379; 514/690
See application file for complete search history.

(56) References Cited

U.S. PATENT DOCUMENTS

| | | | |
|---|---|---|---|
| 7,195,785 B2 | 3/2007 | Babish et al. |
| 7,205,151 B2 | 4/2007 | Babish et al. |
| 7,270,835 B2 | 9/2007 | Tripp et al. |
| 7,332,185 B2 | 2/2008 | Babish et al. |
| 7,431,948 B2 | 10/2008 | Tripp et al. |
| 7,666,449 B2 | 2/2010 | Babish et al. |
| 7,718,198 B2 | 5/2010 | Tripp et al. |
| 7,722,903 B2 | 5/2010 | Tripp et al. |
| 7,736,677 B2 | 6/2010 | Tripp et al. |
| 7,790,205 B2 | 9/2010 | Tripp et al. |
| 7,794,757 B2 | 9/2010 | Tripp et al. |
| 7,807,203 B2 | 10/2010 | Babish et al. |
| 7,811,610 B2 | 10/2010 | Babish et al. |
| 7,815,944 B2 | 10/2010 | Babish et al. |
| 7,820,206 B2 | 10/2010 | Tripp et al. |
| 7,901,713 B2 | 3/2011 | Tripp et al. |
| 7,901,714 B2 | 3/2011 | Tripp et al. |
| 7,919,125 B2 | 4/2011 | Tripp et al. |
| 8,142,819 B2 | 3/2012 | Tripp et al. |
| 2004/0115290 A1 | 6/2004 | Tripp et al. |
| 2004/0219240 A1 | 11/2004 | Babish et al. |
| 2006/0127511 A1 | 6/2006 | Tripp et al. |
| 2006/0127513 A1 | 6/2006 | Tripp et al. |
| 2006/0127514 A1 | 6/2006 | Tripp et al. |
| 2006/0127515 A1 | 6/2006 | Tripp et al. |
| 2007/0160692 A1 | 7/2007 | Tripp et al. |
| 2007/0172532 A1 | 7/2007 | Babish et al. |
| 2007/0184133 A1 | 8/2007 | Tripp et al. |
| 2007/0281045 A1 | 12/2007 | Tripp et al. |
| 2011/0021637 A1 | 1/2011 | Tripp et al. |
| 2011/0039927 A1 | 2/2011 | Madsen et al. |
| 2011/0257074 A1 | 10/2011 | Carroll et al. |

FOREIGN PATENT DOCUMENTS

| | | |
|---|---|---|
| WO | 03000185 A2 | 1/2003 |
| WO | 2004037180 A2 | 5/2004 |
| WO | 2005039483 A2 | 5/2005 |
| WO | 2007002128 A2 | 1/2007 |
| WO | 2007070355 A2 | 6/2007 |
| WO | 2007081710 A2 | 7/2007 |
| WO | 2007081729 A2 | 7/2007 |
| WO | 2008115783 A1 | 9/2008 |
| WO | 2008140842 A1 | 11/2008 |
| WO | 2010068731 A1 | 6/2010 |

OTHER PUBLICATIONS

Babish, J. G., et al., "Antidiabetic Screening of Commercial Botanical Products in 3T3-L1 Adipocytes and db/db Mice," J. Med. Food 13(3):535-547 (2010).
Berge, S. M., et al., "Pharmaceutical Salts," J. Pharm. Sci. 66:1-19 (1977).
Boden, G., "Role of Fatty Acids in the Pathogenesis of Insulin Resistance and NIDDM," Diabetes 45:3-10 (1996).
Dahlberg, C. J., et al., "Countercurrent Purification of the Tetrahydro Iso-alpha Acids Derived from Humulus Lupulus L," J. Sep. Sci. 33:2828-2832 (2010).
De Keukeleire, D., et al., "The Structure and the Absolute Configuration of (−)Humulone," Tetrahedron 26:385-393 (1970).
De Keukeleire, D., et al., "The Absolute Configuration of the Isohumulones and the Humulinic Acids," Tetrahedron 27:4939-4945 (1971).
Dong, S., et al., "Enantioselective Synthesis of Bicyclo[2.2.2]octenones Using a Copper-Mediated Oxidative Dearomatization/[4+2] Dimerization Cascade," J. Am. Chem. Soc. 130(9):2738-2739 (2008).

(Continued)

*Primary Examiner* — Sikarl Witherspoon
(74) *Attorney, Agent, or Firm* — Perkins Coie LLP; Patrick D. Morris

(57) ABSTRACT

The present application provides cis 3,4-dihydroxy-2-(3-methylbutanoyl)-5-(3-methylbutyl)-4-(4-methylpentanoyl)cyclopent-2-en-1-one derivatives and substantially enantiomerically pure compositions thereof. These derivatives include (+)-(4S,5R)-3,4-dihydroxy-2-(3-methylbutanoyl)-5-(3-methylbutyl)-4-(4-methylpentanoyl)cyclopent-2-en-1-one, (−)-(4R,5S)-3,4-dihydroxy-2-(3-methylbutanoyl)-5-(3-methylbutyl)-4-(4-methylpentanoyl)cyclopent-2-en-1-one, and salts and crystals thereof. The application further provides methods of using the disclosed compounds and compositions to activate PPARγ, activate GPR120, inhibit inflammation, and treat conditions responsive to PPARγ modulation, conditions responsive to GPR120 modulation, and metabolic disturbances such as diabetes.

17 Claims, 24 Drawing Sheets

OTHER PUBLICATIONS

Fasshauer, M., et al., "Hormonal Regulation of Adiponectin Gene Expression in 3T3-L1 Adipocytes," Biochem. Biophys. Res. Comm. 290:1084-1089 (2002).

Gotoh, C., et al., "The Regulation of Adipogenesis Through GPR120," Biochem. Biophys. Res. Commun. 354:591-597 (2007).

Hajjaj, H., et al. "Lovastatin Biosynthesis by *Aspergillus terreus* in a Chemically Defined Medium," Applied Environ. Microbiol. 67(6):2596-2602 (2001).

Hara, T et al., "Free Fatty Acid Receptors FFAR1 and GPR120 as Novel Therapeutic Targets for Metabolic Disorders," J. Pharm. Sci. 100(9):3594-3601 (2011).

Hirasawa, A., et al., "Free Fatty Acids Regulate Gut Incretin Glucagon-Like Peptide-1 Secretion Through GPR120," Nat. Med. 11(1):90-94 (2005).

Konda, V. R., et al., "META060 Inhibits Osteoclastogenesis and Matrix Metalloproteinases In Vitro and Reduces Bone and Cartilage Degradation in a Mouse Model of Rheumatoid Arthritis," Arthritis & Rheumatism 62(6):1683-1692 (2010).

Li, Y. et al "Differential Gene Regulation by PPARγ Agonist and Constitutively Active PPARγ2," Mol. Endocrinol. 16(5):1040-1048 (2002).

Martin, G., et al., "PPARgamma Activators Improve Glucose Homeostasis by Stimulating Fatty Acid Uptake in the Adipocytes," Atherosclerosis 137 Suppl.:S75-S80 (1998).

Miyake, T, et al., "Effects of the Principal Nutrients on Lovastatin Production by *Monascus pilosus*," Biosci. Biotechnol. Biochem. 70:1154-1159 (2006).

Oh, D. Y., et al., "GPR120 is an Omega-3 Fatty Acid Receptor Mediating Potent Anti-Inflammatory and Insulin Sensitizing Effects," Cell 142(5):687-698 (2010).

Pascual, G., et al., "A Sumoylation-Dependent Pathway Mediating Transrespression of Inflammatory Response Genes by PPARγ," Nature 437(7059):759-763 (2005).

Raz, I., et al., "Diabetes: Insulin Resistance and derangements in Lipid Metabolism. Cure Through Intervention in Fat Transport and Storage," Diabetes Metab. Res. Rev. 21:3-14 (2005).

Stumvoll, M., et al., "Glitazones: Clinical Effects and Molecular Mechanisms," Ann. Med. 34:217-224 (2002).

Talukdar, S., et al., "Targeting GPR120 and Other Fatty Acid-Sensing GPCRs Ameliorates Insuling Resistance and Inflammatory Diseases," Trends in Pharmacol. Sci. 32(9):543-550 (2011).

Tontonoz, P., et al., "Stimulation of Adipogenesis in Fibroblasts by PPAR gamma 2, A Lipid-Activated Transcription Factor," Cell 79:1147-1156 (1994).

Tontonoz, P., et al., "mPPARγ2: Tissue-Specific Regulator of an Adipocyte Enhancer," Genes Dev. 8:1224-1234 (1994).

Tripp, M.L., et al., "Rho-Iso-Alpha Acids and Tetrahydro-Iso-Alpha Acids are Selective Protein Kinase Inhibitors which Potently Reduce Inflammation in Macrophages In Vitro and in the Collagen-Induced Rheumatoid Arthritis Model In Vivo," Acta Hort (ISHS) 848:221-233 (2009).

Wang, G., et al., "Terpene Biosynthesis in Glandular Trichomes of Hop1,2[W][OA]," Plant Physiol. 148:1254-1266 (2008).

United States Patent and Trademark Office, International Search Report and Written Opinion for PCT/US2011/058477, dated Mar. 16, 2012.

A.

B.

A.

B.

A.

B.

A.

B.

A.

B.

CIS 3,4-DIHYDROXY-2-(3-METHYLBUTANOYL)-5-(3-METHYLBUTYL)-4-(4-METHYLPENTANOYL)CYCLOPENT-2-EN-1-DERIVATIVES, SUBSTANTIALLY ENANTIOMERICALLY PURE COMPOSITIONS AND METHODS

RELATED APPLICATIONS

The present application claims the benefit of U.S. Provisional Application No. 61/408,572, filed Oct. 30, 2010, U.S. Provisional Application No. 61/448,150, filed Mar. 1, 2011, and U.S. Provisional Application No. 61/508,434, filed Jul. 15, 2011. The disclosures of these provisional applications are incorporated by reference herein in their entirety, including drawings.

BACKGROUND

The most abundant member of the alpha acid family is (−)-humulone. The absolute configuration of (−)-humulone has been reported previously (De Keukeleire 1970), as well as the absolute configurational assignments of cis and trans iso-alpha acids which are derived from (−)-humulone (De Keukeleire 1971).

The so-called 'reduced iso-alpha acids'—reduction products derived from both the cis and trans iso-alpha acids—are further categorized. This additional categorization depends on the location and degree of saturation. The class of compounds resulting from the reduction of only the C6 carbonyl to a hydroxyl is collectively referred to as the rho iso-alpha acids (RIAAs). The tetrahydro iso-alpha acid (THIAA) class refers collectively to those compounds where only both isoprenyl moieties are saturated. Similarly, the hexahydro-iso-alpha acids (HIAAs) refers collectively to reduced derivatives of iso-alpha acids containing both the hydroxyl at C6 and saturation of both isoprenyl moieties. In addition to the existence of cis and trans diastereomers, there are a variety of congeners within each of the three classes as a result of the incorporation of various short-chain fatty acids into the biosynthetic pathway of the corresponding phlorglucinols (Wang 2008). The phlorglucinols are common precursors to the alpha acids that are precursors to iso-alpha acids, which are in turn precursors to the reduced alpha iso-acids.

Recently the reduced iso-alpha acids have been shown to possess beneficial effects in the treatment of obesity, dyslipidemia, and inflammation in a variety of in vitro and murine models. A mixture of congeners and stereoisomers of rho iso-alpha acids—referred to as RIAA—demonstrated anti-inflammatory activity in tumor necrosis factor alpha (TNF-α)-stimulated mature 3T3-L1 adipocytes and lipogenic activity in differentiating 3T3-L1 adipocytes (Babish 2010).

A mixture of congeners and stereoisomers of tetrahydro iso-alpha acids—referred to as THIAA—inhibited the activities of spleen tyrosine kinase (Syk), Bruton's tyrosine kinase (Btk), phosphatidylinositol 3-kinase (PI 3-kinase), and glycogen synthase kinase 3β (GSK3β) as well as β-catenin phosphorylation in vitro. Additionally, THIAA inhibited osteoclastogenesis, as indicated by decreased transformation of RAW 264.7 cells to osteoclasts and reduced TRAP activity, and inhibited IL-1β-activated prostaglandin $E_2$, matrix metalloproteinase 3, IL-6, IL-8, and monocyte chemotactic protein 1 in RASFs. Furthermore, in mice with collagen induced arthritis (CIA), this same mixture of congeners and stereoisomers (i.e., THIAA) significantly reduced the arthritis index and decreased bone, joint, and cartilage degradation. Serum IL-6 concentrations in these mice were also inhibited in a dose-dependent manner when treated with THIAA (Konda 2010).

Consistent with these findings it has also been reported that RIAA and THIAA, respectively, inhibited prostaglandin $E_2$ ($PGE_2$) production in lipopolysaccharide-stimulated RAW 264.7 macrophages as well as inhibited inducible cyclooxygenase-2 (COX-2) protein expression. In addition to this, each of these mixtures, i.e., RIAA and THIAA, respectively, are reported to have reduced NF-κB nuclear translocation and abundance in a dose dependent manner (Tripp 2009).

The heterogeneity of the RIAA and THIAA prevents an understanding or knowledge of the relationship among the various congeners and stereo-isomers—present in either the RIAA or THIAA mixture—with respect to their individual and hence relative biological activities. Furthermore, the potential for synergy among the numerous compounds present in RIAA and THIAA may account for much, if not all, of the observed biological activity of these mixtures.

In order to achieve an understanding and knowledge of the relationship among the various congeners and stereo-isomers with respect to their individual and hence relative biological activity, it is imperative that the compounds of interest are obtained, as substantially and enantiomerically pure compounds, and that their individual biological activity is measured in a substantially and enantiomerically pure form. This imperative necessarily follows from the dependence of the biological activity of any heterogenous substance comprised of a mixture of different molecules (e.g., THIAA, RIAA, and HHIAA) on the percent composition, stereochemistry, structure and other properties of the different molecules that comprise the heterogeneous substance. For these reasons there exists a need to prepare and purify substantially enantiomerically pure reduced iso-alpha acid derivatives for use in pharmaceutical compositions and treatments.

In addition to this need there is also a need to manufacture a substantially and enantiomerically pure compound in a form that is suitable for various processes routinely encountered in pharmaceutical development. The manufacture of pure crystalline forms of potential drug candidates is advantageous for drug development. One advantage is the improved characterization of a drug candidate's chemical and physical properties. It is not uncommon for crystalline forms to possess more favorable pharmacokinetics compared to an amorphous form and they are often easier to process. Improved storage stability is an additional advantage often associated with crystalline forms. The physical properties inherent to crystalline forms of potential drug candidates are a significant factor in choosing a particular pharmaceutical active ingredient. An example is the formulation of the potential drug into a suitable composition for manufacture, storage and consumption. Specifically, the flowability of the crystalline solid, pre- and post-milling greatly impacts the manner of how the drug candidate is handled during processing and dose manufacture. In cases where particles of the milled solid form do not flow easily, formulations scientists will endeavor to develop a formulation to compensate for this difficulty. This often involves the use of glidants such as colloidal silicon dioxide, talc, and starch or tri-basic calcium phosphate. An additional solid-state property of a potential pharmaceutical compound is its dissolution rate in aqueous fluid. The physical properties associated with a particular crystalline polymorph are inherently due to the spatial orientation and unique conformation of individual molecules that comprise the unit cell of the crystalline polymorph. A particular crystalline polymorph possesses unique thermal properties that are generally different from either an amorphous form or another polymorph.

The thermal properties of polymorphs are measured using techniques such as capillary melting point, thermogravimetric analysis (TGA) and differential scanning calorimetry (DSC). The results of these measurements are used to distinguish and identify the existence of polymorphic forms and distinguish them from each other. A particular polymorphic form generally possesses distinct crystallographic and spectroscopic properties that are detectable by a variety of techniques including but not limited to powder X-ray powder diffraction (XRPD), single crystal x-ray crystallography, and infrared spectrometry.

SUMMARY

Provided herein in certain embodiments are cis 3,4-dihydroxy-2-(3-methylbutanoyl)-5-(3-methylbutyl)-4-(4-methylpentanoyl)cyclopent-2-en-1-one ("KDT500") derivatives and substantially enantiomerically pure compositions and pharmaceutical compositions comprising these derivatives.

In certain embodiments, the KDT500 derivatives provided herein are selected from (+)-(4S,5R)-3,4-dihydroxy-2-(3-methylbutanoyl)-5-(3-methylbutyl)-4-(4-methylpentanoyl)cyclopent-2-en-1-one ("(+)-KDT500") having the structure set forth in Formula I, (−)-(4R,5S)-3,4-dihydroxy-2-(3-methylbutanoyl)-5-(3-methylbutyl)-4-(4-methylpentanoyl)cyclopent-2-en-1-one ("(−)-KDT500") having the structure set forth in Formula II, and salts and crystals thereof.

Formula I

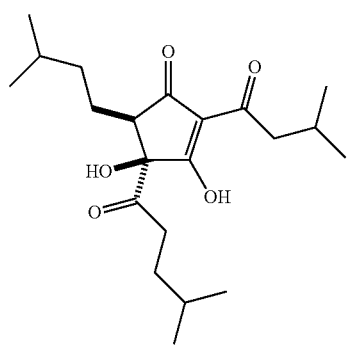

Formula II

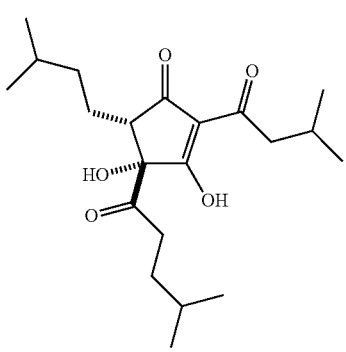

In certain embodiments, the KDT500 derivatives provided herein are salts of (+)-KDT500 or (−)-KDT500. In certain embodiments, these derivatives may be inorganic or organic salts, including but not limited to potassium, aluminum, calcium, copper, guanidinium, iron, lithium, magnesium, sodium, zinc, cinchonidine, cinchonine, and diethanolamine salts of (+)-KDT500 or (−)-KDT500. In certain of these embodiments, the derivative may be a potassium salt of (+)-KDT500 having the structure set forth in Formula III ("(+)-KDT501").

Formula III

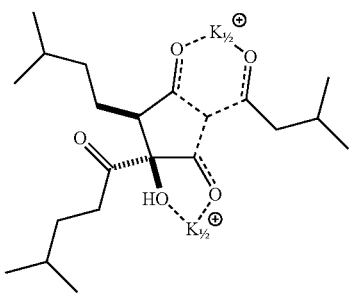

In certain embodiments, the KDT500 derivatives provided herein are crystals of (+)-KDT500, (−)-KDT500, or a salt thereof. In certain of these embodiments, the derivative is a crystal of (+)-KDT501, and in certain of these embodiments the crystal has a monoclinic space group P 21 21 2, and unit cell dimensions of a=23.3110(9)Å, α=90°, b=28.9052(12)Å, β=90°, c=13.6845(5)Å, and γ=90°. In certain embodiments, the crystal has one or more of the traits set forth in Tables 2-4.

Provided herein in certain embodiments are substantially enantiomerically pure compositions of the KDT500 derivatives provided herein. In certain embodiments, these substantially enantiomerically pure compositions comprise (+)-KDT500, (−)-KDT500, or salts or crystals thereof.

Provided herein in certain embodiments are substantially enantiomerically pure pharmaceutical compositions comprising a KDT500 derivative as provided herein and one or more pharmaceutically acceptable carriers. In certain embodiments, these substantially enantiomerically pure pharmaceutical compositions comprise (+)-KDT500, (−)-KDT500, or salts or crystals thereof.

Provided herein in certain embodiments are methods of inducing lipogenesis, inducing adipogenesis, activating PPARγ, or activating GPR120 in vitro or in vivo using one or more of the KDT500 derivatives or compositions thereof provided herein. In certain embodiments, the composition is an substantially enantiomerically pure pharmaceutical composition comprising a KDT500 derivative and one or more pharmaceutically acceptable carriers. In certain embodiments, the methods are used to treat a condition associated with decreased lipogenesis, decreased adipogenesis, or decreased PPARγ or GPR120 activity in a subject in need thereof.

Provided herein in certain embodiments are methods of treating a condition responsive to PPARγ modulation, treating a condition responsive to GPR120 modulation, treating a metabolic disturbance, inhibiting inflammation, or treating a condition associated with inflammation in a subject in need thereof by administering to the subject a therapeutically effective amount of one or more of the KDT500 derivatives or compositions thereof provided herein. In certain of these embodiments, the derivatives are administered via a substantially enantiomerically pure pharmaceutical composition as provided herein. In certain embodiments, the condition responsive to PPARγ modulation is type II diabetes, obesity, hyperinsulinemia, metabolic syndrome, non alcoholic fatty liver disease, non alcoholic steatohepatitis, an autoimmune disorder, or a proliferative disorder. In certain embodiments, the metabolic disturbance is diabetes. In certain embodiments, administration of the compounds or compositions provided herein results in a decrease in glucose and/or lipid levels, including triglyceride levels.

DETAILED DESCRIPTION

Figure 1:
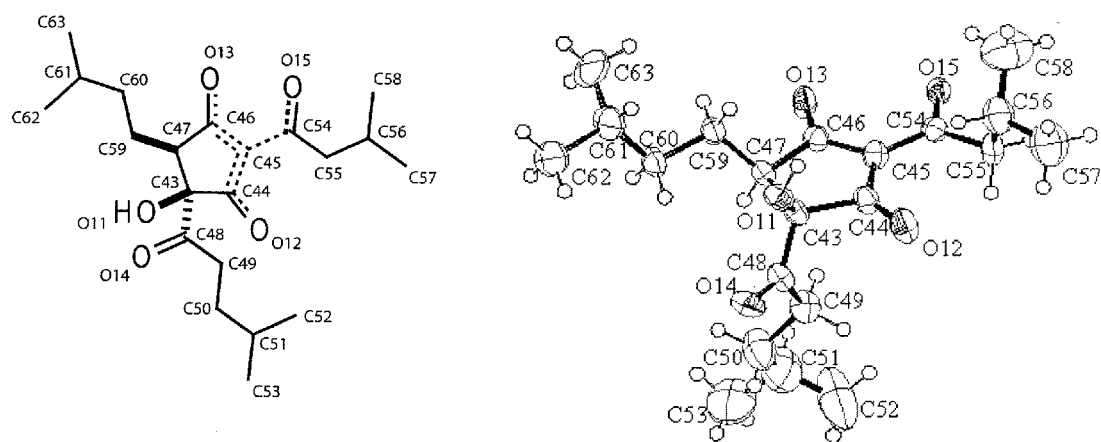
FIG. 1: The stereochemical structure of (+)-KDT501. Potassium ions and water molecule from unit cell are omitted.

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

As disclosed herein, cis 3,4-dihydroxy-2-(3-methylbutanoyl)-5-(3-methylbutyl)-4-(4-methylpentanoyl)cyclopent-2-en-1-one ("KDT500") derivatives have been synthesized, purified, and characterized. Therefore, provided herein in certain embodiments are KDT500 derivatives and salts and crystals thereof, including crystals of the salts. Also provided herein are compositions comprising these derivatives and salts and crystals thereof, including substantially enantiomerically pure compositions.

The term "salt" as used herein may refer to any pharmaceutically acceptable salt, including for example inorganic base salts such as potassium, aluminum, calcium, copper, guanidinium, iron, lithium, magnesium, sodium, and zinc salts and organic base salts such as cinchonidine, cinchonine, and diethanolamine salts. Additional examples of pharmaceutically acceptable salts and preparations in accordance with the present invention can be found in, for example, Berge J Pharm Sci 66:1 (1977).

In certain embodiments, a KDT500 derivative as provided herein has the structure set forth in Formula I or Formula II:

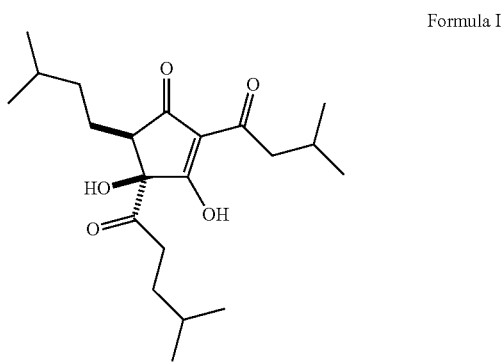

Formula I

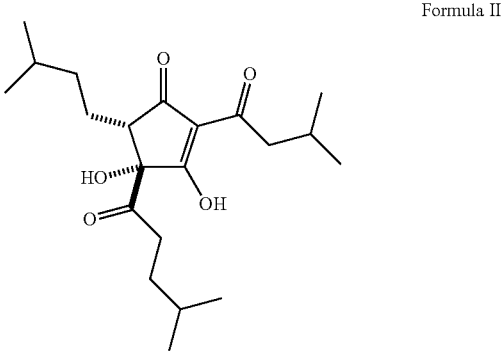

Formula II

The compounds of Formula I and Formula II represent (+)-(4S,5R)-3,4-dihydroxy-2-(3-methylbutanoyl)-5-(3-methylbutyl)-4-(4-methylpentanoyl)cyclopent-2-en-1-one (referred to herein as "(+)-KDT500") and (−)-(4R,5S)-3,4-dihydroxy-2-(3-methylbutanoyl)-5-(3-methylbutyl)-4-(4-methylpentanoyl)cyclopent-2-en-1-one (referred to herein as "(−)-KDT500"), respectively. Therefore, in certain preferred embodiments, a KDT500 derivative as provided herein is (+)-KDT500 or (−)-KDT500.

In certain embodiments, a KDT500 derivative as provided herein is a salt of KDT500. Salts of KDT500 include, but are not limited to, potassium salts, magnesium salts, calcium salts, zinc salts, iron salts, sodium salts, copper salts, guanidinium salts, cinchonidine salts, and cinchonine salts of KDT500. For example, a salt of KDT500 may be ((+)-(4S, 5R)-3,4-dihydroxy-2-(3-methylbutanoyl)-5-(3-methylbutyl)-4-(4-methylpentanoyl)cyclopent-2-en-1-one potassium salt (referred to herein as "(+)-KDT501") has the structure set forth in Formula III:

Formula III

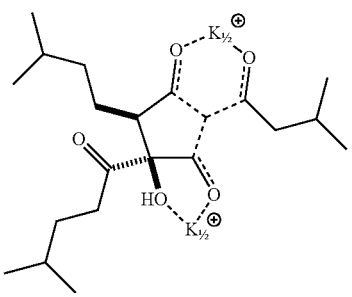

In other embodiments, a KDT500 derivative as provided herein is a crystal of KDT500 or a salt thereof, including for example KDT501. In certain of these embodiments, crystals of (+)-KDT501 are provided that have a monoclinic space group P 21 21 2 and unit cell dimensions of a=23.3110(9)Å (α=90°), b=28.9052(12)Å (β=90°), and c=13.6845(5)Å (γ=90°). This crystal form of (+)-KDT501 is referred to herein as "crystal (+)-KDT501."

In certain embodiments, crystal (+)-KDT501 has the three dimensional atomic coordinates set forth in Table 2, the bond lengths and angles set forth in Table 3, and/or the anisotropic displacement parameters set forth in Table 4, where the anisotropic displacement factor exponent takes the form: $-2\pi^2 [h^2 a^{*2} U^{11} + \ldots + 2hka^*b^*U^{12}]$.

Provided herein in certain embodiments are compositions comprising one or more of the KDT500 derivatives provided herein. In certain of these embodiments, the compositions are substantially enantiomerically pure. The term "substantially enantiomerically pure" as used herein refers to a composition in which 90% or more of a particular compound in the composition is in a first enantiomeric form, while 10% or less is in a second enantiomeric form. For example, in a substantially enantiomerically pure (+)-KDT500 composition, 90% or more of the KDT500 in the composition is (+)-KDT500 and 10% or less is (−)-KDT500. In certain embodiments, the "first enantiomeric form" of a compound includes salts and crystals of that enantiomeric form. For example, in a substantially enantiomerically pure (+)-KDT500 composition, 90% or more of the KDT500 in the composition is in the form of (+)-KDT500 or salts or crystals thereof, while 10% or less is in the form of (−)-KDT500 or salts or crystals thereof. In certain embodiments, a substantially enantiomerically composition may contain 91%, 92%, 93%, 94%, 95%, 96%, 97%, 98%, 99%, 99.5%, 99.9%, 99.95%, or 99.99% or greater of a first enantiomeric form of a compound.

In certain embodiments, compositions of (+)-KDT500 are provided. In certain of these embodiments, the compositions are substantially enantiomerically pure. In certain of these embodiments, a percentage of the (+)-KDT500 in the composition is in the form of salts or crystals of (+)-KDT500. In some of these embodiments, all of the (+)-KDT500 in the composition is in salt or crystal form. Thus, provided herein are substantially enantiomerically pure compositions of (+)-KDT500 salts or crystals. In other embodiments, none of the (+)-KDT500 in the composition is in salt or crystal form.

In certain embodiments, compositions of (+)-KDT500 are provided. In certain of these embodiments, the compositions are substantially enantiomerically pure. In certain of these embodiments, a percentage of the (−)-KDT500 in the composition is in the form of salts or crystals of (−)-KDT500. In some of these embodiments, all of the (−)-KDT500 in the composition is in salt or crystal form. Thus, provided herein are substantially enantiomerically pure compositions of (−)-KDT500 salts or crystals. In other embodiments, none of the (−)-KDT500 in the composition is in salt or crystal form.

Provided herein in certain embodiments are pharmaceutical compositions comprising one or more of the KDT500 derivatives provided herein and one or more pharmaceutically acceptable carriers. In certain embodiments, the pharmaceutical compositions are substantially enantiomerically pure. In certain of these embodiments, the substantially enantiomerically pure pharmaceutical compositions comprise (+)-KDT500, (−)-KDT500, or salts or crystals thereof. A "pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. Such a carrier may comprise, for example, a liquid or solid filler, diluent, excipient, solvent, encapsulating material, stabilizing agent, or some combination thereof. Each component of the carrier must be "pharmaceutically acceptable" in that it must be compatible with the other ingredients of the composition and must be suitable for contact with any tissue, organ, or portion of the body that it may encounter, meaning that it must not carry a risk of toxicity, irritation, allergic response, immunogenicity, or any other complication that excessively outweighs its therapeutic benefits.

Examples of pharmaceutically acceptable carriers for use in the compositions provided herein include, but are not limited to, (1) sugars, such as lactose, glucose, sucrose, or mannitol; (2) starches, such as corn starch and potato starch; (3) cellulose and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) disintegrating agents such as agar or calcium carbonate; (14) buffering agents, such as magnesium hydroxide and aluminum hydroxide; (15) alginic acid; (16) pyrogen-free water; (17) isotonic saline; (18) Ringer's solution; (19) alcohol, such as ethyl alcohol and propane alcohol; (20) phosphate buffer solutions; (21) paraffin; (22) lubricants, such as talc, calcium stearate, magnesium stearate, solid polyethylene glycol, or sodium lauryl sulfate; (23) coloring agents; (24) glidants such as colloidal silicon dioxide, talc, and starch or tri-basic calcium phosphate; and (24) other non-toxic compatible substances employed in pharmaceutical compositions such as acetone. In one embodiment, the pharmaceutically acceptable carrier used herein is an aqueous carrier, e.g., buffered saline and the like. In other embodiments, the pharmaceutically acceptable carrier is a polar solvent, e.g., acetone and alcohol.

Pharmaceutical compositions as provided herein may further comprise one or more pharmaceutically acceptable auxiliary substances as required to approximate physiological conditions. For example, compositions may comprise one or more pH adjusting agents, buffering agents, or toxicity adjusting agents, including for example sodium acetate, sodium chloride, potassium chloride, calcium chloride, sodium lactate, and the like.

Pharmaceutical compositions as provided herein may be formulated into a suitable dosage form, including for example capsules, cachets, pills, tablets, lozenges (using a flavored basis, usually sucrose and acacia or tragacanth), powders, granules, as a solution or a suspension in an aqueous or non-aqueous liquid, as an oil-in-water or water-in-oil liquid emulsion, as an elixir or syrup, or as pastilles (using an inert base, such as gelatin and glycerin, or sucrose and acacia) and/or as mouth washes and the like, each containing a predetermined amount of a KDT500 derivative as an active ingredient. In certain embodiments, the compositions may be formulated as a time release delivery vehicle, such as for example a time release capsule. A "time release vehicle" as used herein refers to any delivery vehicle that releases active agent over a period of time rather than immediately upon administration. In other embodiments, the compositions may be formulated as an immediate release delivery vehicle.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a substantially enantiomerically pure mixture of the powdered KDT500 derivative or further moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of a KDT500 derivative therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain pacifying agents and may be of a composition that they release the KDT500 derivative (s) only, or preferentially, in a certain portion of the gastrointestinal tract, optionally, in a delayed manner. Examples of embedding compositions which can be used include polymeric substances and waxes. The KDT500 derivative can also be in micro-encapsulated form, if appropriate, with one or more of the above-described excipients.

The concentration of KDT500 derivatives in the compositions provided herein may vary. Concentrations may be selected based on fluid volumes, viscosities, body weight, and the like in accordance with the particular mode of administration selected and the biological system's needs. In certain embodiments, the concentration of a KDT500 derivative in a composition provided herein may be from about 0.0001% to 100%, from about 0.001% to about 50%, from about 0.01% to about 30%, from about 0.1% to about 20%, or from about 1% to about 10% wt/vol.

Further provided herein are methods of analyzing, synthesizing, purifying, and/or crystallizing the KDT500 derivatives provided herein, as well as methods of analyzing, synthesizing, purifying, and/or crystallizing the substantially enantiomerically pure KDT500 compositions provided herein.

In certain embodiments, the synthesis methods provided herein generate a single enantiomer of a KDT500 derivative. For example, the synthesis methods may generate only (+)-KDT500 or only (−)-KDT500. In other embodiments, the synthesis methods result in a mixture of enantiomeric forms of KDT500 derivatives. In these embodiments, one or more subsequent separation and/or purification steps may be performed to isolate a single enantiomeric form or to generate a substantially enantiomerically pure composition as provided herein.

In certain of the synthesis and purification methods provided herein, (+)-KDT500 and/or (−)-KDT500 may be synthesized using lupulone as a starting material (see, e.g., Example 11 below). In one of these synthesis/purification methods, lupulone is first converted to tetrahydro-deoxyhumulone via reductive de-alkylation, and tetrahydro-deoxyhumulone is converted to enantiomerically pure tetrahydro-humulone ((+) and/or (−)) via asymmetric oxidation. The resulting enantiomer is purified and converted to the corresponding cis iso-humulone via enantio- and diastereoselective isomerization.

In another embodiment, (+)-KDT500 and/or (−)-KDT500 may be synthesized using deoxy humulone as a starting material (see, e.g., Example 12 below). In one embodiment, deoxy humulone is first converted to (+)-humulone and/or (−)-humulone respectively via asymmetric oxidation. The (+)-humulone is converted to the corresponding enantiomerically pure (−)-cis isohumulone by enantio- and diastereoselective isomerization, and then further converted to (−)-KDT500 via hydrogenation. The (−)-humulone is converted to the corresponding enantiomerically pure (+)-cis isohumulone by enantio- and diastereoselective isomerization, and then further converted to (+)-KDT500 via hydrogenation.

In another embodiment, enantiomerically pure (+)-humulone and (−)-humulone can be purified from the racemic (±)-humulone (see, e.g., Example 13 below). In another embodiment, enantiomerically pure (+)-tetrahydro humulone and (−)-tetrahydro humulone can be purified from the racemic (±)-tetrahydro humulone (see, e.g., Example 14 below).

As disclosed herein, (+)-KDT501 was evaluated for its effects on lipogenesis and adipogenesis in a 3T3-L1 murine fibroblast model. (+)-KDT501 was found to induce both lipogenesis and adipogenesis in a dose-dependent manner. The 3T3-L1 murine fibroblast allows investigation of preadipocyte replication, adipocyte differentiation, and insulin sensitizing effects (Fasshauer 2002; Li 2002; Raz 2005). It has been reported that an agent that promotes lipid uptake in fat cells improve insulin sensitivity. One hypothesis is that the incorporation of fatty acids into the adipocyte from the plasma causing a relative depletion of fatty acids in the muscle with a concomitant improvement of glucose uptake (Martin 1998). Insulin desensitizing effects of free fatty acids in muscle and liver would be reduced as a consequence of thiazolidinedione treatment. These in vitro results have been confirmed clinically (Boden 1997; Stumvoll 2002).

(+)-KDT501 and (−)-KDT501 were both evaluated for their ability to competitively bind PPARγ, SCN2A, and AGTR2 in the presence of agonist ligands for each of these targets. Both molecules exhibited the ability to bind all three binding targets in the presence of their agonist ligands, with (+)-KDT501 exhibiting a higher degree of affinity for all three targets. Of the targets, (+)-KDT501 bound PPARγ with the greatest affinity. (+)-KDT501 and (−)-KDT501 were next evaluated for their effect on PPAR activity. Both compounds increased PPARγ activity while having little or no effect on PPARα or PPARδ activity. However, the effect of (+)-KDT501 on PPARγ activity was at least three times that of (−)-KDT501 at all concentrations, suggesting that (+)-KDT501 is substantially more effective as a PPARγ activator. PPARγ is a master regulator in adipogenesis, glucose homeostasis, and insulin sensitivity, and is the molecular target of thiazolidinediones, which sensitize cells to insulin and have antidiabetic effects in the liver, adipose tissue and skeletal muscle (Tontonoz 1994; Tontonoz 1994).

Based on the ability of the KDT500 derivatives provided herein to induce lipogenesis, adipogenesis, and PPARγ activity, methods are provided herein for inducing lipogenesis, inducing adipogenesis, and/or activating PPARγ, as well as methods of treating a condition responsive to PPARγ modulation, in a subject in need thereof by administering a therapeutically effective amount of one or more of the KDT500 derivatives provided herein or substantially enantiomerically pure pharmaceutical compositions thereof. Examples of conditions responsive to PPARγ modulation include, for example, conditions treatable by improved glucose and energy homeostasis, including but not limited to Type II diabetes, obesity, hyperinsulinemia, metabolic syndrome, non alcoholic fatty liver disease, non-alcoholic steatohepatitis, an autoimmune disorder, and proliferative disorder.

As discussed above, previously identified PPARγ agonists have been shown to suppress the inflammatory response. PPARγ not only activates transcription of target genes for lipid metabolism, but also reduces expression of inflammation genes (Pascual 2005). Suppression of the inflammatory response by PPARγ agonists is closely linked to anti-diabetic and anti-atherosclerotic effects. To evaluate the role of KDT501 in inflammation, (+)-KDT501 was evaluated for its ability to inhibit expression of various TNF-α-, LPS-, and IL-1β-mediated inflammatory factors. (+)-KDT501 was found to inhibit TNF-α- and LPS-mediated expression of MMP-9, MCP-1, RANTES, and MIP-1α in THP-1 cells, and to inhibit IL-1β-mediated expression of $PGE_2$ and MMP-13 in rheumatoid arthritis synovial fibroblast (RASF) cells. In addition, both (+)-KDT501 and (−)-KDT501 were found to inhibit DAPK1 activity, with (+)-KDT501 showing the greatest efficacy.

The ability of KDT501 to improve insulin sensitivity and glucose regulation as well as reduce pro-inflammatory signals suggests a mechanism that influences the interaction between insulin signaling and inflammation pathways. One potential mechanism for this activity is via stimulation of a G protein coupled receptor. To evaluate this possibility, the effect of (+)-KDT501 on the activity of the ω3 fatty acid sensitizing G-protein coupled receptor GPR120 was tested. Activation of GPR120 improves insulin sensitivity and reduces inflammation by inhibiting the NF-κB pathway (Oh 2010; Talukdar 2011). GPR120 has also been shown to mediate GLP-1 secretion in intestinal L cells (Hirasawa 2005; Hara 2011) and to increase lipogenesis in adipocytes (Goth 2007), both of which contributed to antidiabetic effects. (+)-KDT501 was found to agonize GPR120 activity with an $EC_{50}$ value of 30.3 μM, suggesting that (+)-KDT501 may exert its lipogenic effects in part via GRP120 activation.

Based on the ability of the KDT500 derivatives provided herein to induce GPR120 activity, methods are provided herein for treating a condition responsive to GPR120 modulation in a subject in need thereof by administering a therapeutically effective amount of one or more of the KDT500 derivatives provided herein or substantially enantiomerically pure pharmaceutical compositions thereof. Further, based on the ability of the KDT500 derivatives provided herein to induce GPR120 and PPARγ activity and to inhibit the expression of various TNF-α-, LPS-, and IL-1β-mediated inflammatory factors, methods are provided herein for inhibiting inflammation in a subject in need thereof by administering a therapeutically effective amount of one or more of the KDT500 derivatives provided herein or substantially enantiomerically pure pharmaceutical compositions thereof. Also provided herein are methods for treating various conditions associated with inflammation and/or conditions associated with elevated levels of one or more of the inflammatory factors MMP-9, IL-1β, MCP-1, RANTES, MIP-1α, $PGE_2$, and MMP-13 in a subject in need thereof by administering a therapeutically effective amount of one or more of the KDT500 derivatives provided herein or substantially enantiomerically pure pharmaceutical compositions thereof. Such conditions include, for example, atherosclerosis, atherosclerotic plaque instability, autoimmune diseases such as rheumatoid arthritis, cartilage degradation, osteoarthritis, allergic conditions, immunodeficiency diseases such as HIV/AIDS, nephropathies, tumors, and diabetes.

As disclosed herein, (+)-KDT501 was evaluated for its ability to alter glucose and lipid levels in rat diabetes model. At a once daily dosage of 200 mg/kg, (+)-KDT501 was found to significantly lower glucose levels. This decrease was much greater than that observed in rats treated with metformin, and similar to that seen in rats treated with pioglitazone. Similarly, (+)-KDT501 was found to decrease triglyceride levels to a degree nearly the same as that observed with pioglitazone.

In a mouse model, twice daily administration of (+)-KDT501 was effective at reducing circulating whole blood glucose and insulin levels, reducing glucose and insulin area under the concentration-time curves (AUCs) in the oral glucose tolerance test (OGTT), and decreasing fat mass in diet induced obese (DIO) mice. A reduction trend in the percentage glycated hemoglobin (HbA1c) was also observed over a 30 day period in the DIO mice.

Based on the ability of the KDT500 derivatives provided herein to lower circulating glucose, triglyceride, and insulin levels in rat and mice models, methods are provided herein for treating metabolic disturbances by administering a therapeutically effective amount of one or more of the KDT500 derivatives provided herein or substantially enantiomerically pure pharmaceutical compositions thereof. A "metabolic disturbance" as used herein refers to any condition that results in loss of metabolic control of homeostasis. Examples of metabolic disturbances include, for example, diabetes, hyperglycemia, weight gain, insulin resistance, dyslipidemia, and hypercholesterolemia. In certain embodiments, methods are provided for treating diabetes, including Type II diabetes, in a subject in need thereof by administering a therapeutically effective amount of one or more of the KDT500 derivatives or substantially enantiomerically pure pharmaceutical compositions provided herein. Similarly, in certain embodiments methods are provided for decreasing glucose and/or lipid levels in a subject in need thereof by administering a therapeutically effective amount of one or more of the KDT500 derivatives or substantially enantiomerically pure pharmaceutical compositions provided herein. In certain embodiments, administration of the KDT500 derivatives or compositions results in a decrease in blood glucose levels and/or a decrease in triglyceride levels. In certain embodiments, administration of the KDT500 derivatives or compositions results in a decrease in one or more additional lipid levels, including for example total cholesterol or LDL levels.

In certain embodiments of the methods provided herein, the subject is a mammal, and in certain of these embodiments the subject is a human. A "subject in need thereof" refers to a subject diagnosed with a condition responsive to PPARγ modulation or a metabolic disturbance, a subject who exhibits or has exhibited one or more symptoms of a condition responsive to PPARγ modulation or a metabolic disturbances, or a subject who has been deemed at risk of developing a condition responsive to PPARγ modulation or a metabolic disturbances based on one or more hereditary or environmental factors.

The terms "treat," "treating," or "treatment" as used herein with regards to a condition refers to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

A "therapeutically effective amount" of a KDT500 derivative or pharmaceutical composition as used herein is an amount of a composition that produces a desired therapeutic effect in a subject. The precise therapeutically effective amount is an amount of the compound or composition that will yield the most effective results in terms of therapeutic efficacy in a given subject. This amount will vary depending upon a variety of factors, including but not limited to the characteristics of the therapeutic compound (including, e.g., activity, pharmacokinetics, pharmacodynamics, and bioavailability), the physiological condition of the subject (including, e.g., age, sex, disease type and stage, general physical condition, responsiveness to a given dosage, and type of medication), the nature of the pharmaceutically acceptable carrier or carriers in the composition, and the route of administration. One skilled in the clinical and pharmacological arts will be able to determine a therapeutically effective amount through routine experimentation, namely by monitoring a subject's response to administration of a compound and adjusting the dosage accordingly. For additional guidance, see Remington: The Science and Practice of Pharmacy 21$^{st}$ Edition, Univ. of Sciences in Philadelphia (USIP), Lippincott Williams & Wilkins, Philadelphia, Pa., 2005, the entire disclosure of which is incorporated by reference herein.

In certain embodiments, a therapeutically effective amount of a KDT500 derivative or composition as provided herein may be selected from about $10^{-10}$ g to about 100 g, about $10^{-10}$ g to about $10^{-3}$ g, about $10^{-9}$ g to about $10^{-6}$ g, about $10^{-6}$ g to about 100 g, about 0.001 g to about 100 g, about 0.01 g to about 10 g, or about 0.1 g to about 1 g of active ingredient (i.e., KDT500 derivative) per subject per day. In certain embodiments, a therapeutically effective amount of a KDT500 derivative or composition may be calculated based on the body weight of the subject. For example, in certain embodiments, a therapeutically effective amount may be about 100 mg/kg or greater, about 150 mg/kg or greater, about 200 mg/kg or greater, about 250 mg/kg or greater, or about 300 mg/kg or greater of active ingredient (i.e., KDT500 derivative) per subject per day.

In certain embodiments, a compound or composition as provided herein may be administered one or more times a day. In other embodiments, the compound or composition may be delivered less than once a day. For example, the compound or composition may be administered once a week, once a month, or once every several months. Administration of a compound or composition provided herein may be carried out over a specific treatment period determined in advance, or it may be carried out indefinitely or until a specific therapeutic benchmark is reached. For example, administration may be carried out until glucose and/or lipid levels reach a pre-determined threshold. In certain embodiments, dosing frequency may change over the course of treatment. For example, a subject may receive less frequent administrations over the course of treatment as certain therapeutic benchmarks are met.

The compounds and compositions disclosed herein may be delivered to a subject by any administration pathway known in the art, including but not limited to oral, aerosol, enteral, nasal, ophthalmic, parenteral, or transdermal (e.g., topical cream or ointment, patch). "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Methods for preparing parenterally administrable compositions will be known or apparent to those skilled in the art and are described in more detail in such publications as Remington: The Science and Practice of Pharmacy 21st ed., Mack Publishing Company, Easton, Pa. (2005). A composition may also be administered as a bolus, electuary, or paste.

In certain embodiments, kits are provided that comprise one or more of the KDT500 derivatives or substantially enantiomerically pure compositions thereof provided herein. In certain embodiments, the kit provides instructions for usage, such as dosage or administration instructions. In certain embodiments, the kits may be used to treat a condition responsive to PPARγ or GPR120 modulation, treat a metabolic disturbance such as diabetes, decrease glucose and/or lipid levels, inhibit inflammation, or treat a condition associated with inflammation in a subject in need thereof.

In certain embodiments, the KDT500 derivatives and substantially enantiomerically pure KDT500 derivative compositions provided herein may be used as flavoring agents. In certain of these embodiments, the compounds are used as bitter flavoring agents.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Example 1

Crystallization and Characterization of Substantially Enantiomerically-Pure (+)- and (−)-KDT500 Derivatives Crystallization of (+)-KDT501 (Scheme I):

100 g of predominantly cis tetrahydro-iso alpha acids obtained during hops processing was purified using high-speed countercurrent chromatography (HSCCC) according to a reported procedure (Dahlberg 2010). HPLC and UV peak area analysis showed that the resultant product was >90% KDT500. The purified material was converted to (+)-KDT501 by reacting with 1 equivalent of potassium salt (e.g., KOH), and was recrystallized multiple times to remove discoloration. After achieving sufficient homogeneity, the (+)-KDT501 was further recrystallized to render crystals of (+)-KDT501 with sufficient dimension for x-ray diffraction experiments.

Scheme I

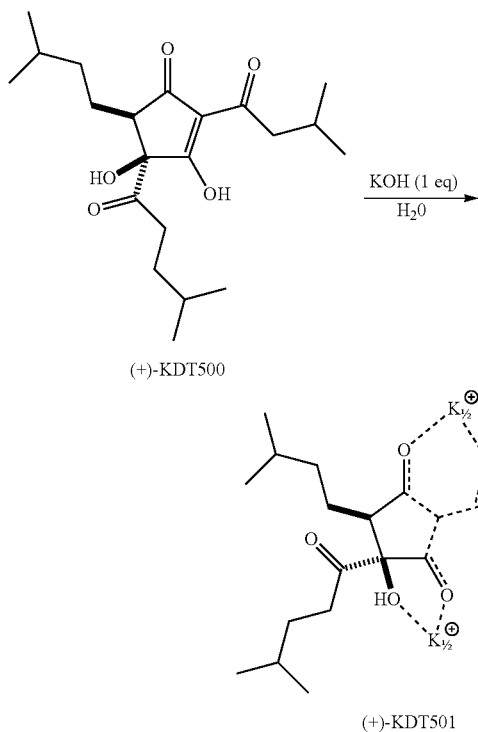

(+)-KDT500

(+)-KDT501

Water (450 μL) and (+)-KDT501 (49.5 mg) were added to a 4 mL vial, and the vial was sealed with a cap and heated using a thermal heating block (70° C.) until dissolution. The solution was allowed to cool to 35° C. over a two hour period. During this time, in situ formation of crystals was observed. The mixture was allowed to stand at room temperature (22° C.) for eight hours, at which point the formation of additional crystals was observed. An individual crystal suitable for x-ray analysis was identified, carefully removed from solution, mounted, and submitted to X-ray diffraction analysis.

Resolution of the Crystal Structure of (+)-KDT501:

A colorless block, measuring 0.37×0.30×0.28 mm$^3$ was mounted on a glass capillary with oil. Data was collected at −163° C. on a Bruker APEX II single crystal X-ray diffractometer, Mo-radiation. Crystal-to-detector distance was 40 mm and exposure time was 10 seconds per degree for all sets. The scan width was 0.5°. Data collection was 98.4% complete to 25° in θ. A total of 68211 (merged) reflections were collected covering the indices, h=−26 to 28, k=−34 to 34, l=−16 to 14. 16681 reflections were symmetry independent and the $R_{int}$=0.0386 indicated that the data was good (average quality 0.07). Indexing and unit cell refinement indicated primitive orthorhombic lattice. The space group was found to be P2$_1$ 2$_1$ 2 (No. 18).

Data was integrated and scaled using SAINT, SADABS within the APEX2 software package (Bruker 2007 APEX2 (Version 2.1-4), SAINT (version 7.34A), SADABS (version 2007/4), BrukerAXS Inc, Madison, Wis.).

Solution by direct methods (SHELXS; SIR97 (Altomare J Appl Cryst 32:115 (1999), Altomare J Appl Cryst 26:343 (1993)) produced a complete heavy atom phasing model consistent with the proposed structure. The structure was completed by difference Fourier synthesis with SHELXL97 (Sheldrick, "SHELXL-97: Program for the Refinement of Crystal Structures," University of Gottingen, Germany (1997); Mackay "MaXus: a computer program for the solution and refinement of crystal structures from diffraction data," University of Glasgow, Scotland (1997)). Scattering factors are from Waasmair and Kirfel (Waasmaier Acta Crystallogr A 51:416 (1995)). Hydrogen atoms were placed in geometrically idealised positions and constrained to ride on their parent atoms with C—H distances in the range 0.95-1.00 Angstrom. Isotropic thermal parameters $U_{eq}$ were fixed such that they were 1.2 $U_{eq}$ of their parent atom Ueq for CH's and 1.5 $U_{eq}$ of their parent atom $U_{eq}$ in the case of methyl groups. All non-hydrogen atoms were refined anisotropically by full-matrix least-squares. The crystal structure of (+)-KDT501 is set forth in FIG. 1. Crystallographic data is set forth in Table 1, three dimensional atomic coordinates are set forth in Table 2, bond lengths and angles are set forth in Table 3, and anisotropic displacement parameters (where the anisotropic displacement factor exponent takes the form: $-2\pi^2$ [$h^2 a^{*2} U^{11}+ \ldots +2hka^*b^*U^{12}$]) are set forth in Table 4.

Figure 2:
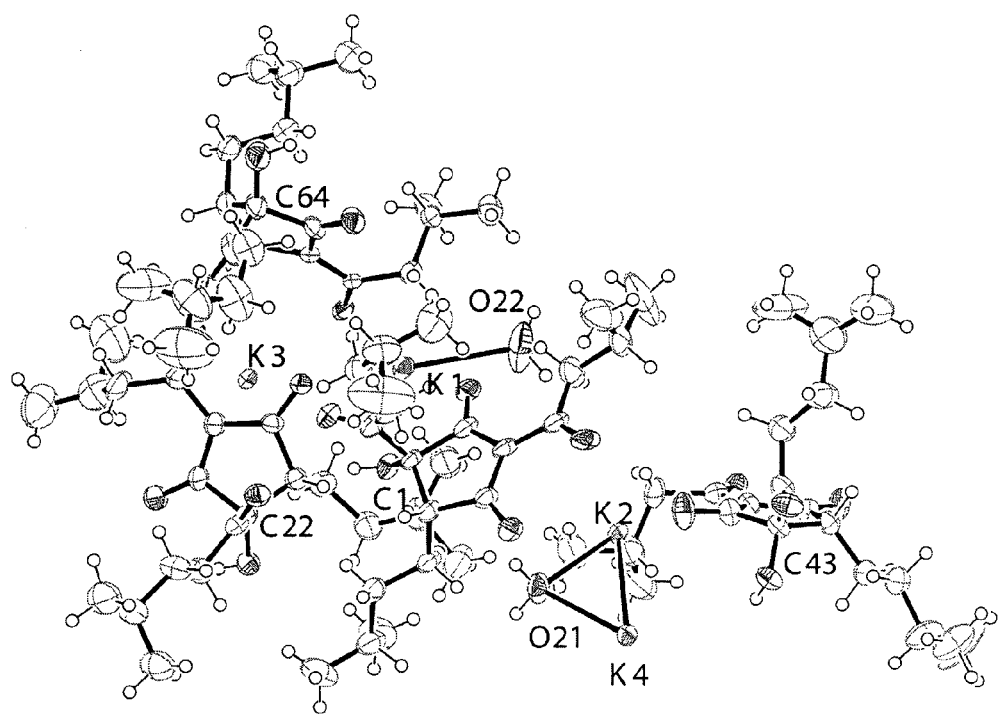
FIG. 2: An ORTEP drawing of the (+)-KDT501 crystal for its asymmetric unit.

The asymmetric unit for the (+)-KDT501 crystalline form consists of 4 of (+)-KDT501 molecules coordinating four potassium cations. Two potassium cations are bridged with oxygen; a disordered water molecule coordinates with the other two. The ketones of the organic moieties coordinate with the potassium cations leading to a close packing pattern. The asymmetric unit of (+)-KDT501 is shown in FIG. 2. The absolute configuration was obtained from anomalous scattering (Absolute structure parameter=0.04(4)).

Figure 3:
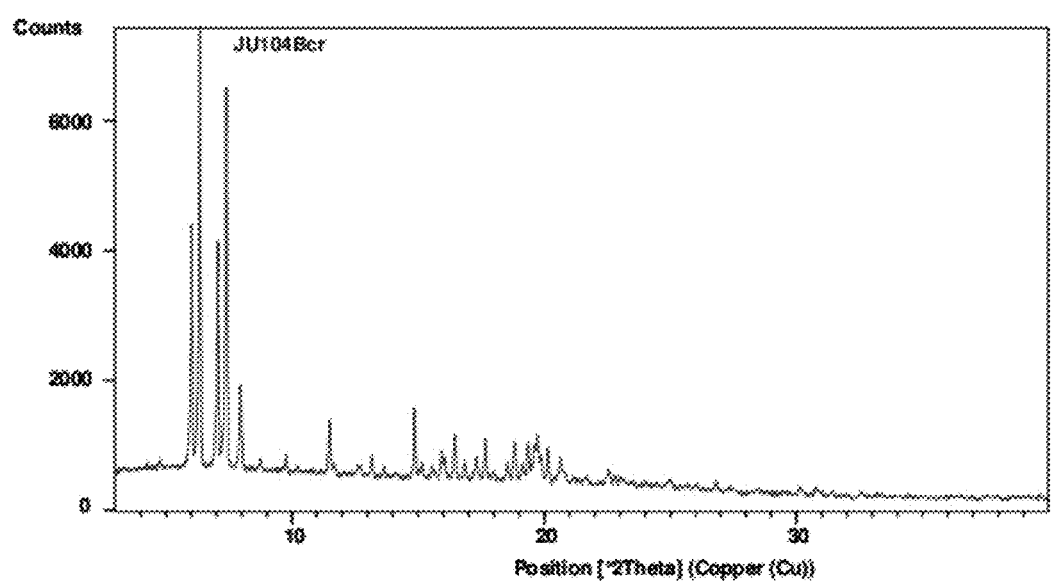
FIG. 3: XRPD diffractogram of (+)-KDT501.

X-Ray Powder Diffraction (XRPD) and Thermal Analysis of (+)-KDT501:

XRPD analyses were performed using a Panalytical Xpert Pro diffractometer equipped with a Cu X-ray tube and a Pixcel detector system. The isothermal samples were analyzed in transmission mode and held between low density polyethylene films. The XRPD diffractogram showed that (+)-KDT501 is crystalline (FIG. 3).

Thermogravimetric/Differential Temperature Analyser (TG/DTA):

Thermal analysis was carried out on a Perkin Elmer Diamond. The calibration standards were indium and tin. Samples were placed in an aluminum sample pan, inserted into the TG furnace and accurately weighed. The samples were heated from 30° C.-300° C. in a stream of nitrogen at a rate of 10° C./minute. The temperature of the furnace was equilibrated at 30° C. prior to the analysis of the samples.

Figure 4:
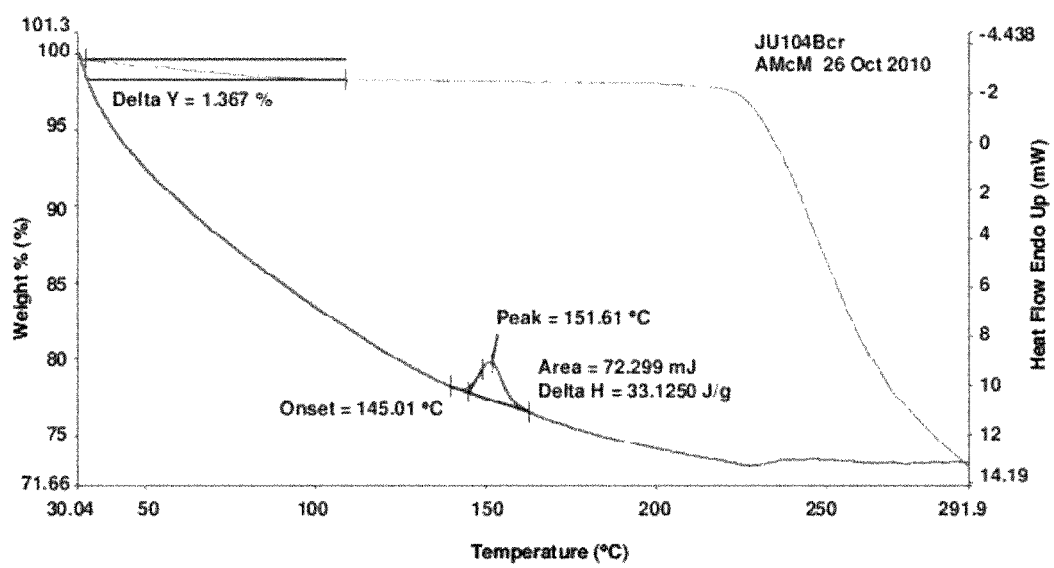
FIG. 4: TG/DTA thermogram of (+)-KDT501.

The TG/DTA thermogram (FIG. 4) showed a weight loss of 1.37% indicating some solvent loss, which was indicative of a hydrate or solvate. No other thermal events, apart from the melting endotherm with an onset of 145° C. were present.

Example 2

Effect of (+)-KDT501 on Lipogenesis in 3T3-L1 Adipocytes

The effect of (+)-KDT501 on lipogenesis was evaluated in 3T3-L1 adipocytes.

Murine 3T3-L1 preadipocytes (ATCC, Rockville, Md.) were maintained in DMEM (Invitrogen, Rockville, Md.) supplemented with 10% fetal bovine serum (FBS; ATCC). As preadipocytes, 3T3-L1 cells have a fibroblastic appearance. They replicate in culture until they form a confluent monolayer, after which cell-cell contact triggers $G_0/G_1$ growth arrest. Subsequent stimulation with 3-isobutyl-1-methylxanthane, dexamethasone, and high does of insulin for two days prompts the cells to undergo post-confluent mitotic clonal expansion, exit the cell cycle, and begin to express adipocyte-specific genes. Approximately five days after induction of differentiation, the cells display the characteristic lipid-filled adipocyte phenotype.

Cells were seeded at an initial density of approximately $1.5 \times 10^6$ cells in 24-well plates and allowed to grow for 2 days to confluence. Cells were treated with (+)-KDT501 (25, 12.5, 6.25, and 3.25 µM), rosiglitazone (10 µM, positive control; Cayman Chemicals, Ann Harbor, Mich.), or DMSO (negative control) on day 0. After this initial treatment, cells were differentiated into adipocytes by addition of differentiation medium consisting of 10% FBS/DMEM (high glucose), 0.5 mM methylisobutylxanthine (Sigma, St. Louis, Mo.), 0.5 µM dexamethasone (Sigma), and 10 µg/mL insulin (Sigma). After two days, the medium was changed to progression medium consisting of 10 µg/mL insulin in 10% FBS/DMEM. After two more days, the medium was changed to maintenance medium consisting of 10% FBS/DMEM. Cells were re-treated with (+)-KDT501 or rosiglitazone in DMSO every two days throughout the maturation phase (day 6/day 7). Whenever fresh medium was added, fresh test material was also added.

Figure 5:
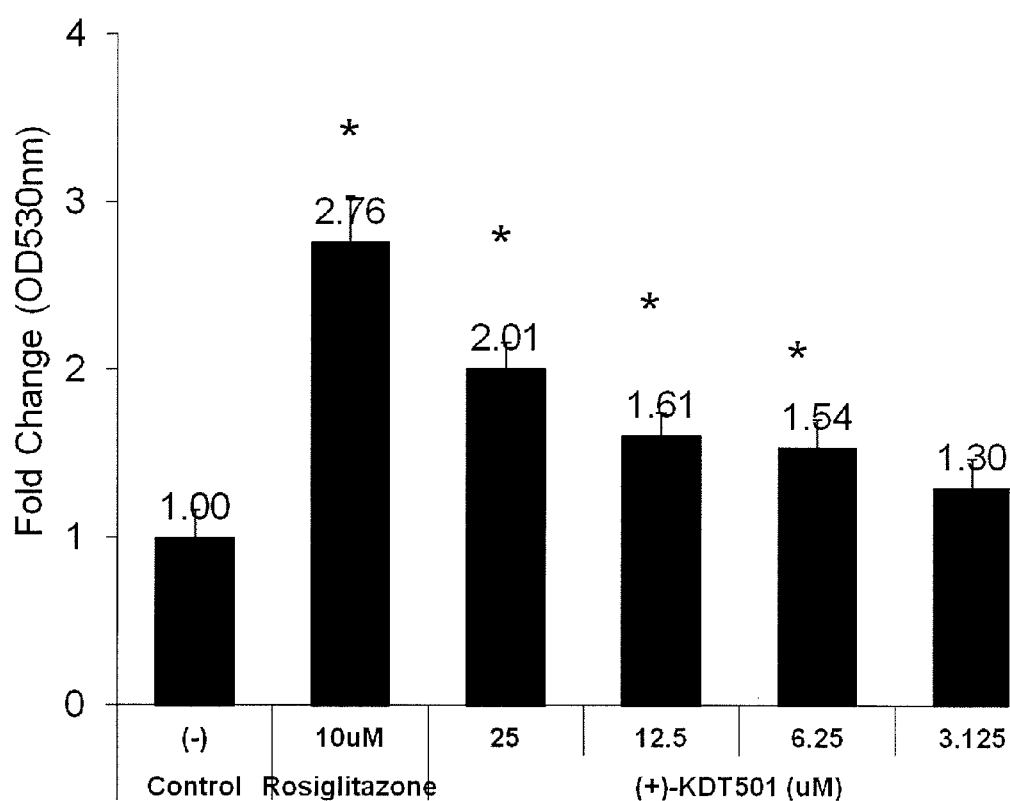
FIG. 5: Effect of (+)-KDT501 on lipogenesis in 3T3-L1 adipocytes. Rosiglitazone was used as a positive control.
Figure 6:
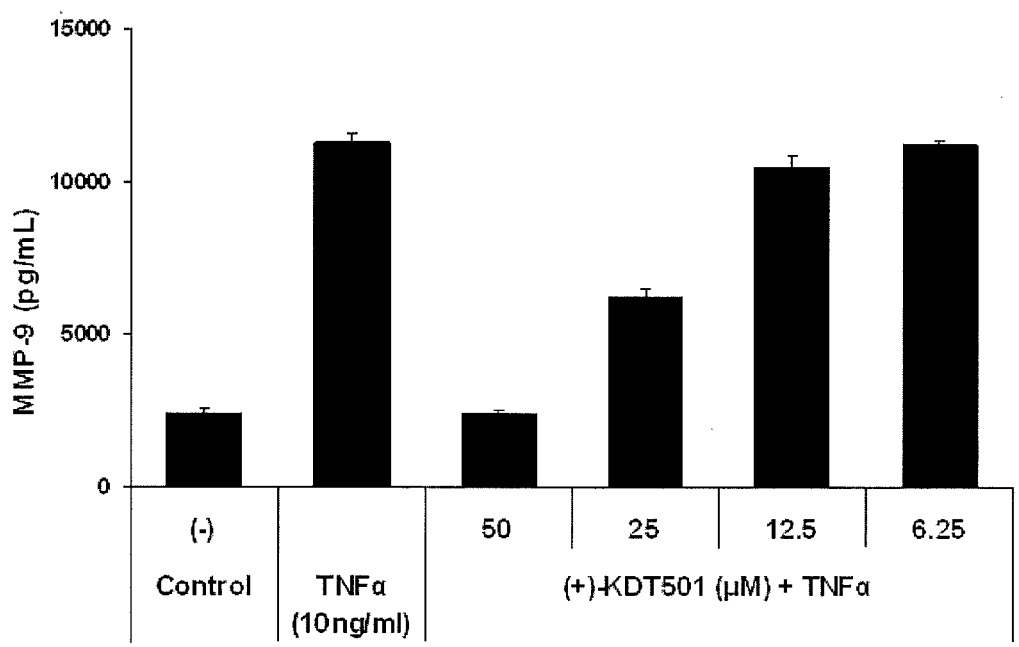
FIG. 6: Effect of (+)-KDT501 on TNF-α-(A) and LPS-(B) mediated MMP-9 expression levels in THP-1 cells. Data represents mean±SD from four experiments.
Figure 6:
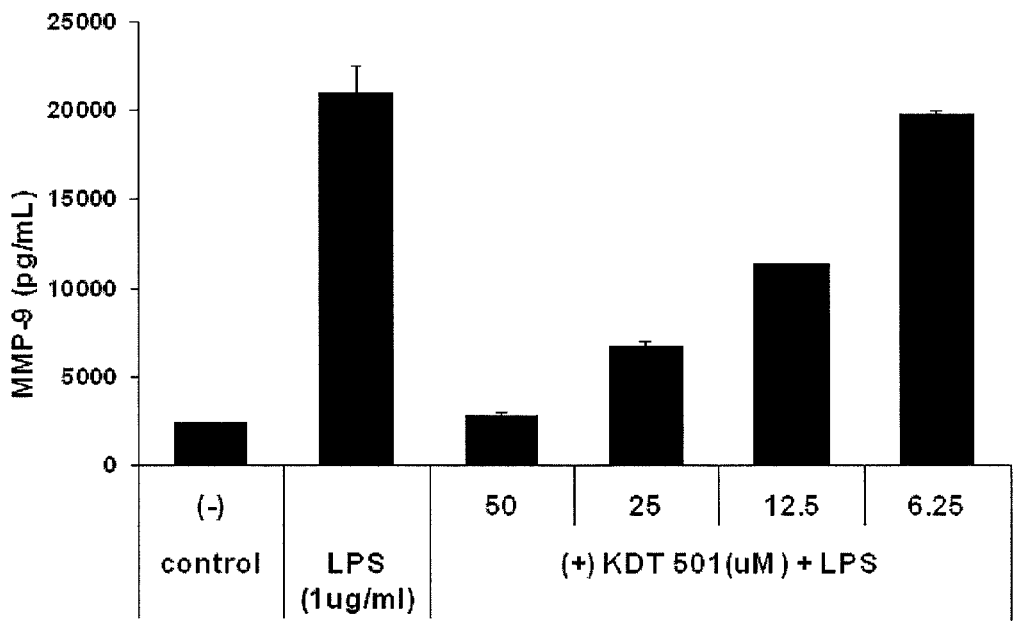
Figure 7:
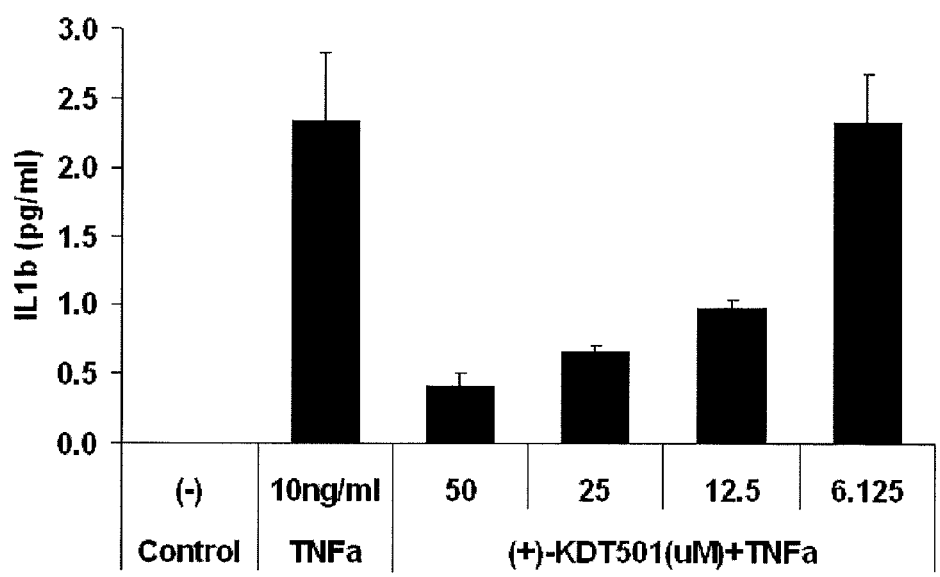
FIG. 7: Effect of (+)-KDT501 on TNF-α-(A) and LPS-(B) mediated IL-1β expression levels in THP-1 cells. Data represents mean±SD from four experiments.
Figure 7:
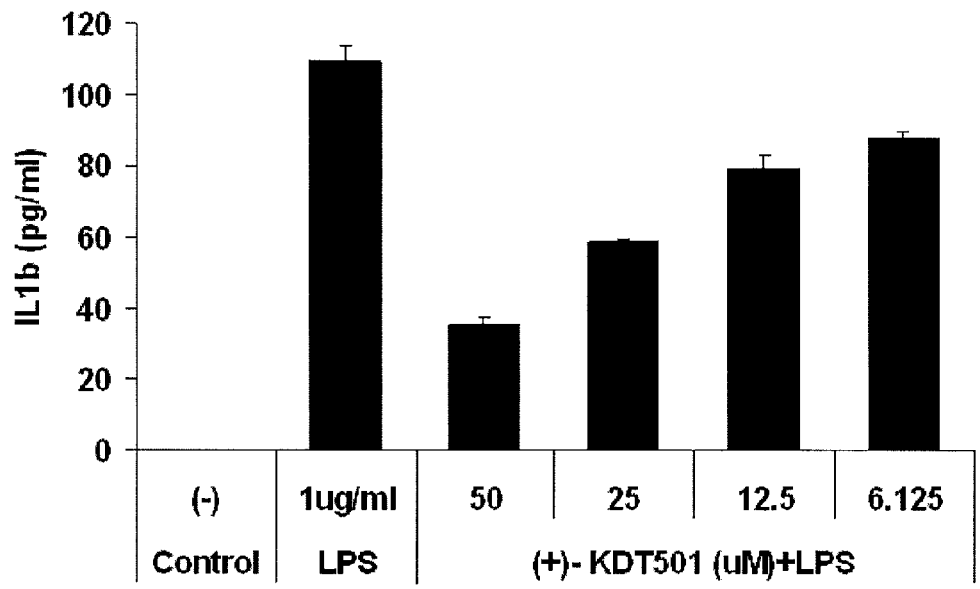
Figure 8:
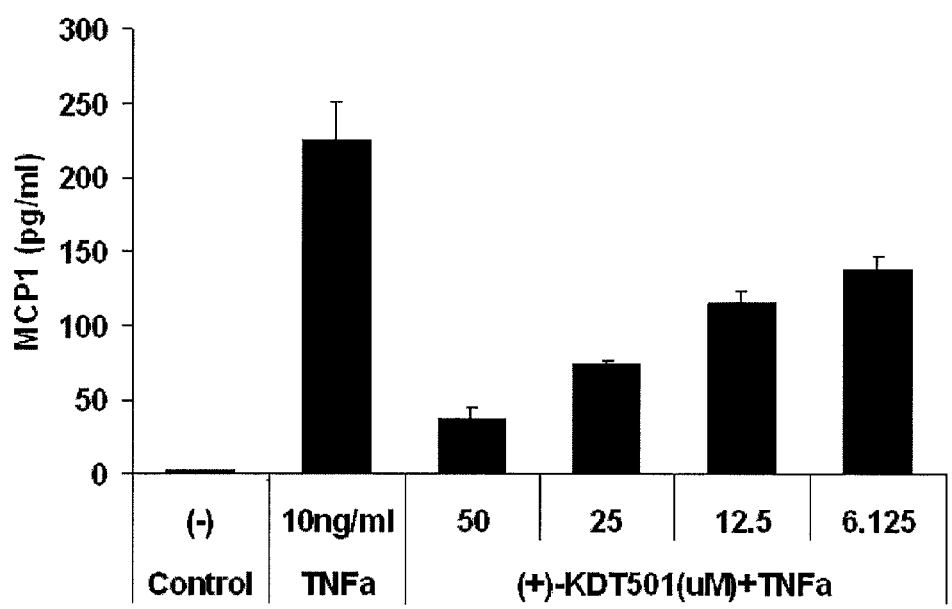
FIG. 8: Effect of (+)-KDT501 on TNF-α-(A) and LPS-(B) mediated MCP-1 expression levels in THP-1 cells. Data represents mean±SD from four experiments.
Figure 8:
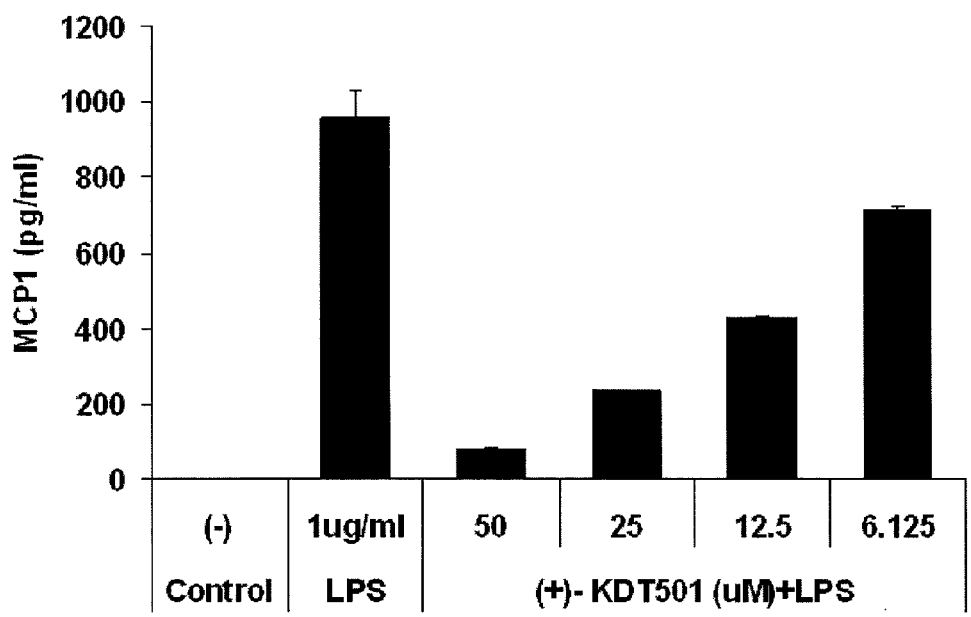
Figure 9:
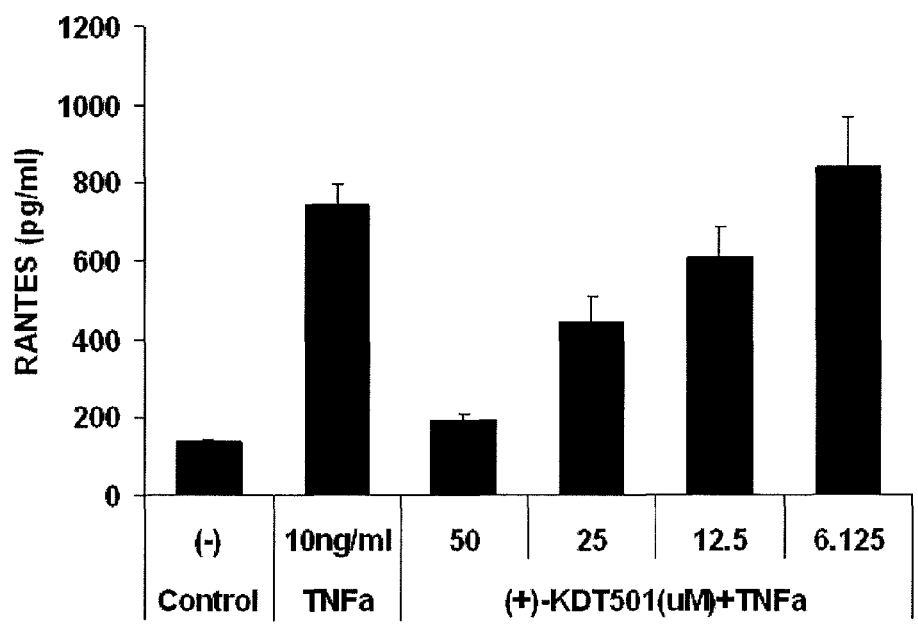
FIG. 9: Effect of (+)-KDT501 on TNF-α-(A) and LPS-(B) mediated RANTES expression levels in THP-1 cells. Data represents mean±SD from four experiments.
Figure 9:
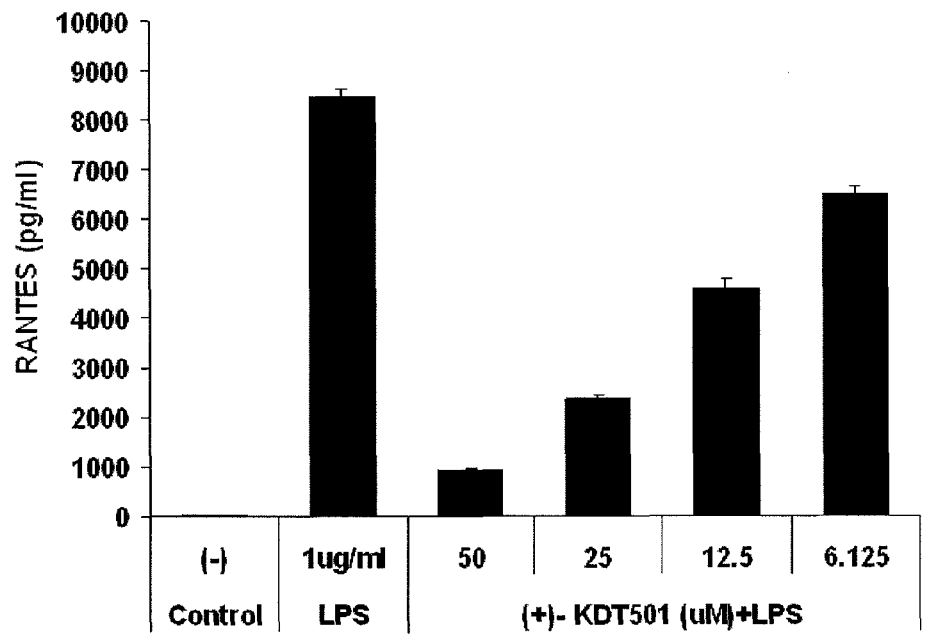
Figure 10:
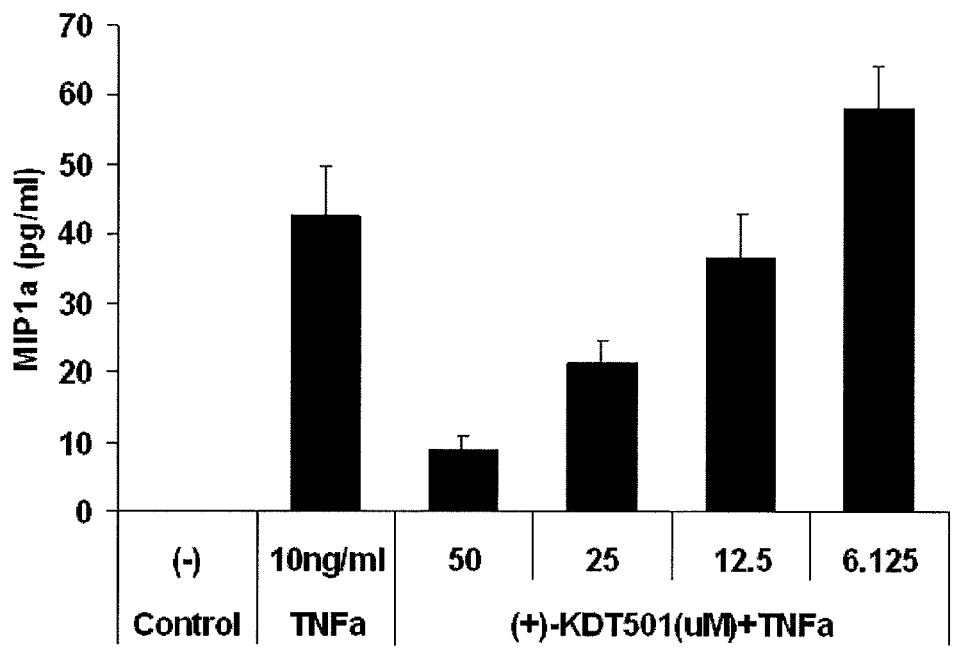
FIG. 10: Effect of (+)-KDT501 on TNF-α-(A) and LPS-(B) mediated MIP-1α expression levels in THP-1 cells. Data represents mean±SD from four experiments.
Figure 10:
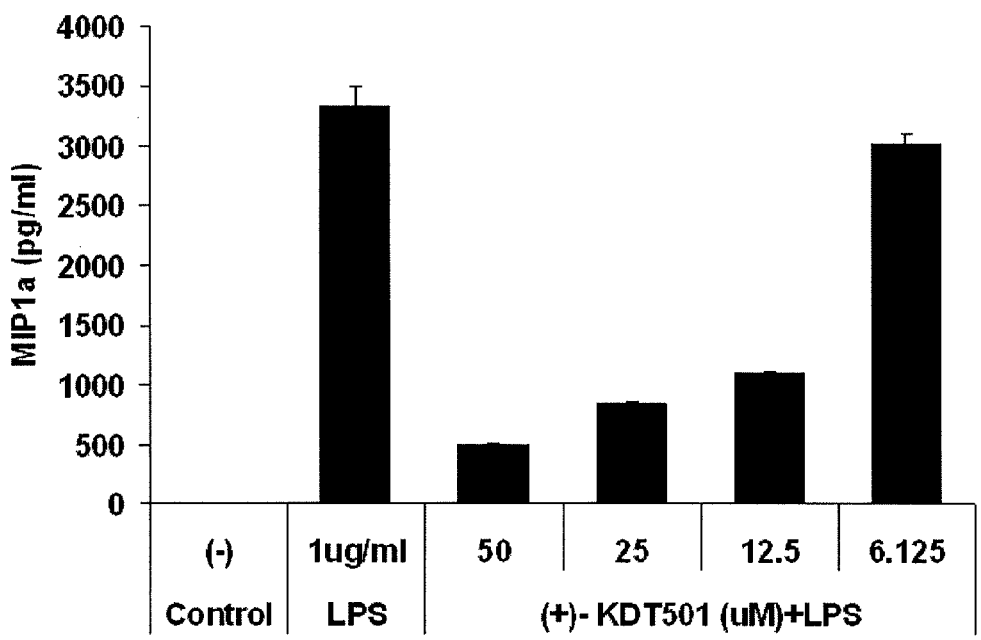

Microscopic evaluation was performed at day 0 and every two days throughout testing to assess preadipocyte differentiation to adipocyte morphology. Intracellular lipid was quantified with Oil Red O staining. The medium was carefully discarded after day 8/day 9 without disturbing the cell layer. 10% formalin was added and incubated for 15 minutes, and the plates were washed with 60% isopropanol and dried for 10 minutes at room temperature. 300 µl of Oil red O solution (0.36% in 60% ethanol; Millipore, Billerica, Mass.) was added and incubated for 10 minutes at room temperature. The plate was washed with 70% ethanol followed by two washes with water. Dye was extracted by adding 200 µl of 100% isopropanol for 20 minutes. 150 µL of sample was transferred to a 96 well plate and absorbance was measured at 530 nm using a plate reader (Thermo Electron Corp.). 100% isopropanol was used as blank. Results are summarized in FIG. 5. (+)-KDT501 at 6.25, 12.5, and 25 µM increased lipogenesis in 3T3-L1 adipocytes in a statistically significant manner. The observed increase was comparable to that seen with rosiglitazone.

Example 3

Effect of (+)-KDT501 on TNF-α- and LPS-Mediated Inflammatory Factors in THP-1 Cells The anti-inflammatory effect of (+)-KDT501 was evaluated in human monocytic THP-1 cells.

THP-1 cells (ATCC, Manassas, Va.) were maintained in RPMI1640 in the presence of 10% serum according to manufacturer's instructions. The cells were pre-incubated with (+)-KDT501 at varying concentrations (50, 25, 12.5 and 3.125 µM) for one hour, then stimulated with TNF-α(10 ng/ml; Sigma, St. Louis, Mo.) or E. coli LPS (1 µg/ml; Sigma, St. Louis, Mo.) overnight (16-20 hours). MMP-9 levels in the medium were measured using an ELISA kit (GE Healthcare, Piscataway, N.J.), and cytokines were assayed using a Milliplex MAP human cytokine/chemokine kit (Millipore, Billerica, Mass.). Analytes were quantified using a Luminex 100™ IS. Data were analyzed using a five-parameter logistic method.

Results are shown in FIGS. 6-10. (+)-KDT501 inhibited TNF-α and LPS-induced expression of MMP-9 (FIG. 6), IL-1β (FIG. 7), MCP-1 (FIG. 8), RANTES (FIG. 9), and MIP-1α (FIG. 10) in a dose-dependent manner.

Example 4

Effect of (+)-KDT501 on IL-1β-Mediated Inflammatory Factors in RASFs

The anti-inflammatory effect of (+)-KDT501 was evaluated in rheumatoid arthritis synovial fibroblasts (RASF).

Human RASF cells (Asterand, Detroit, Mich.) were cultured and maintained in DMEM/F12 (1:1) medium in the presence of 10% fetal bovine serum. Cells were subcultured in 24-well plates at a density of $1 \times 10^4$ cells per well and allowed to reach 70-80% confluence in two days. Confluent cells in serum-free medium at a final concentration of 0.1% DMSO were incubated for one hour with (+)-KDT501 at varying concentrations (50, 25, 12.5, and 6.25 µM), then stimulated with IL-1β (10 ng/ml) for 20-24 hours. MMP-13 levels in the medium were measured using an ELISA kit (GE Healthcare, Piscataway, N.J.), and $PGE_2$ levels were measured using an Immuno Assay Kit (Assay Designs, Ann Arbor, Mich.).

Figure 11:
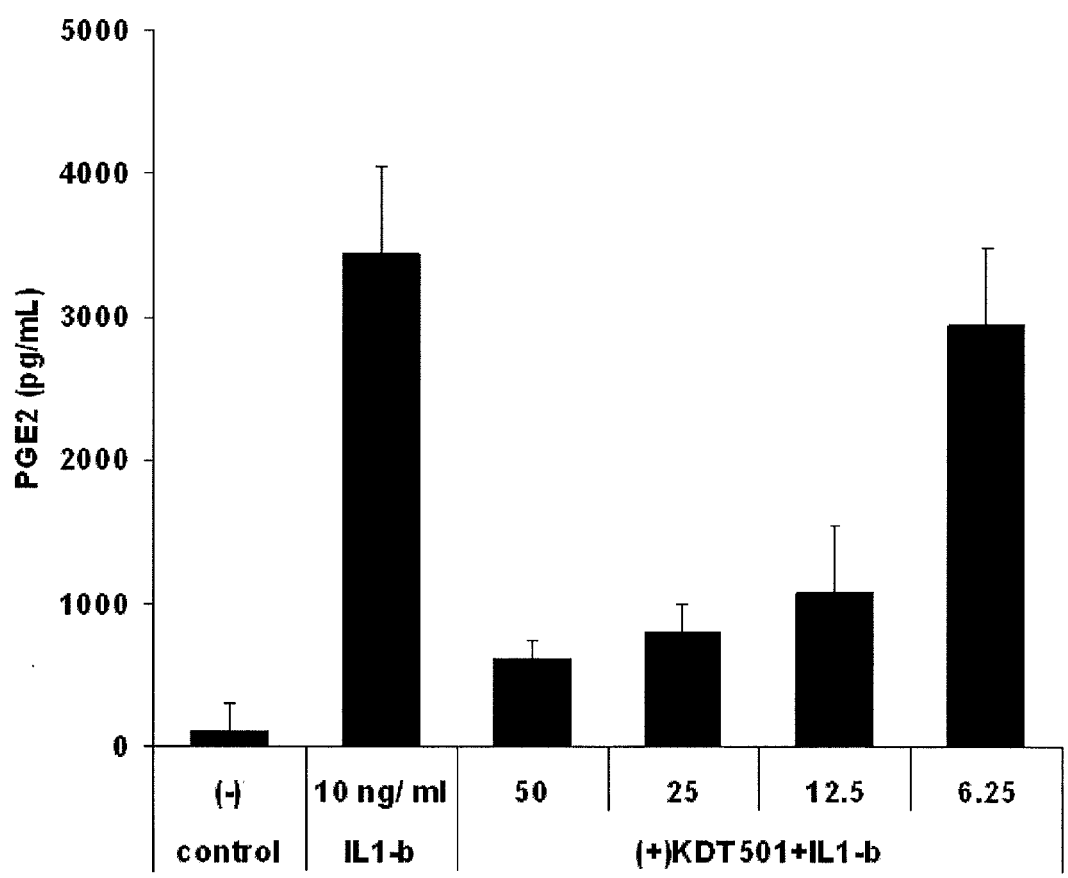
FIG. 11: Effect of (+)-KDT501 on IL-1β-mediated PGE$_2$ levels in RASFs.
Figure 12:
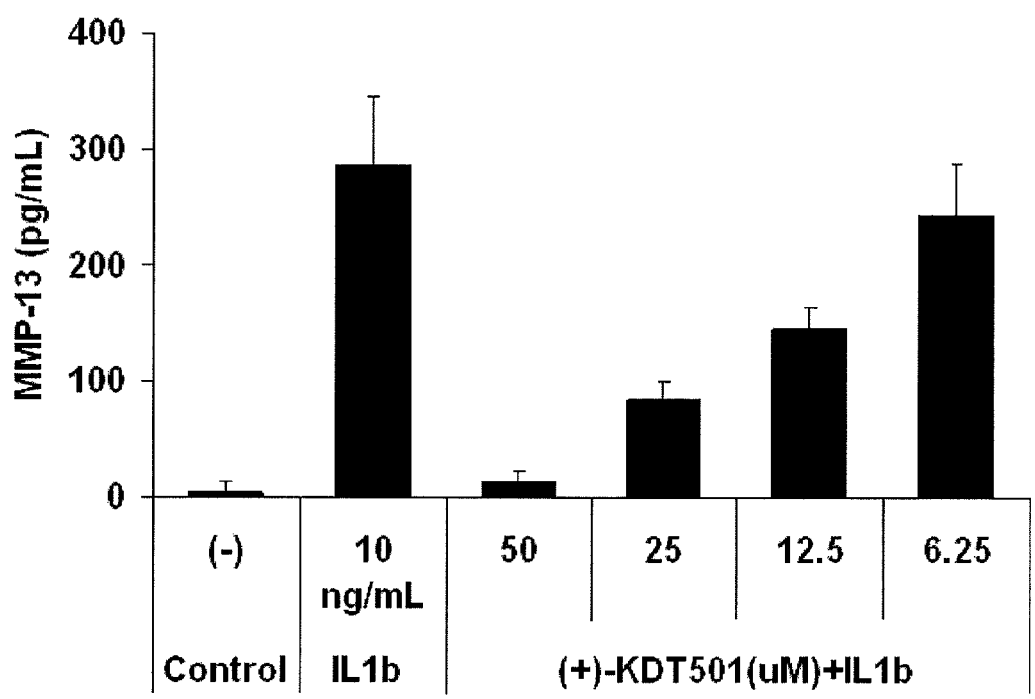
FIG. 12: Effect of (+)-KDT501 on IL-1β-mediated MMP13 levels in RASFs.

Results are shown in FIGS. 11 and 12. (+)-KDT501 inhibited IL-1β-induced expression of $PGE_2$ (FIG. 11) and MMP-13 (FIG. 12).

Example 5

Competitive Binding of KDT501 to PPARγ, SCN2A, and AGTR2

Competitive binding of (+)-KDT501 to peroxisome proliferator-activated receptor gamma (PPARγ), voltage-gated sodium channel type II (SCN2A), and angiotensin II receptor type II (AGTR2) was evaluated in the presence of the agonists rosiglitazone, veratridine, and angiotensin-II, respectively.

For PPARγ, cell membrane homogenates (8 µg protein) were incubated for 120 minutes at 4° C. with 5 nM [$^3$H] rosiglitazone in the presence or absence of (+)-KDT501 in a buffer containing 10 mM Tris-HCl (pH 8.2), 50 mM KCl and 1 mM DTT, and nonspecific binding was determined in the presence of 10 µM rosiglitazone.

For SCN2A, cell membrane homogenates of cerebral cortex (200 µg protein) were incubated for 60 minutes at 22° C. with 10 nM [$^3$H]batrachotoxinin in the presence or absence of (+)-KDT501 in a buffer containing 50 mM Hepes/Tris (pH 7.4), 130 mM choline chloride, 5.4 mM KCl, 0.8 mM $MgSO_4$, 1 g/l glucose, 0.075 g/l scorpion venom and 0.1% BSA, and nonspecific binding was determined in the presence of 300 µM veratridine.

For AGTR2, cell membrane homogenates (5 µg protein) were incubated for 240 min at 37° C. with 0.01 nM [$^{125}$I]CGP 42112A (angiotensin-II receptor type II agonist) in the presence or absence of (+)-KDT501 in a buffer containing 50 mM Tris-HCl (pH 7.4), 5 mM $MgCl_2$, 1 mM EDTA and 0.1% BSA, and nonspecific binding was determined in the presence of 1 µM angiotensin II.

Following incubation, samples were filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters were dried and then counted for radioactivity in a scintillation counter (Topcount, Packard) using a scintillation cocktail (Microscint 0, Packard).

Results are summarized in Table 5. (+)-KDT501 exhibited the ability to bind all three targets in the presence of their agonist ligands, with the highest affinity binding occurring with PPARγ.

TABLE 5

| Binding target | Competitor ligand | $IC_{50}$ (μM) | $K_i$ (μM) | $n_H$ |
|---|---|---|---|---|
| PPARγ | Rosiglitazone | 8.4 | 4.5 | 1.1 |
| SCN2A | Veratridine | 19 | 17 | 1.7 |
| AGTR2 | Angiotensin-II | 14 | 7.1 | 1.4 |

The binding experiments were repeated as described above using (−)-KDT501 instead of (+)-KDT501. These results are summarized in Table 6. Like (+)-KDT501, (−)-KDT501 exhibited the ability to bind all three targets in the presence of their agonist ligands. However, the $IC_{50}$ and $K_i$ of (−)-KDT501 for all three targets was higher than that exhibited by (+)-KDT501.

TABLE 6

| Binding target | Competitor ligand | $IC_{50}$ (μM) | $K_i$ (μM) | $n_H$ |
|---|---|---|---|---|
| PPARγ | Rosiglitazone | 30 | 16 | 1.1 |
| SCN2A | Veratridine | 24 | 22 | 0.7 |
| AGTR2 | Angiotensin-II | 32 | 16 | 0.9 |

Example 6

Effect of KDT501 on PPAR Activity

The functional effect of (+)-KDT501 on PPARα, PPARδ, and PPARγ activity was evaluated using a PPAR reporter assay (INDIGO Biosciences, PA). This assay utilizes non-human mammalian cells engineered to provide constitutive high level expression of PPARα, PPARδ, or PPARγ and containing a luciferase report gene specific to the appropriate PPAR. Following activation by agonist binding, PPAR induces expression of the luciferase reporter gene. Luciferase activity therefore provides a surrogate for measuring PPAR activity in agonist-treated cells.

Reporter cells were plated on a 96-well plate at 100 μL per well, and 100 μL of (+)-KDT501 at various final concentrations (25, 12.5, 6.25, 3.125, 1.56 and 0.78 μM) was added to each well. For the PPARγ assay, rosiglitazone (1, 0.5, 0.25, 0.125, 0.063 and 0.031 μM) and telmisartan (10, 5, 2.5, 1.25, and 0.625 μM) were used as positive controls. For the PPARα assay, GW590735 (10, 5, 1, 0.5, 0.25, 0.125, 0.063, and 0.031 μM) was used as a positive control and rosiglitazone (1, 0.5, 0.25, 0.125, 0.063 and 0.031 μM) was used as a negative control. For the PPARδ assay, GW0742 (1, 0.5, 0.25, 0.125, 0.0625, 0.031, 0.016, and 0.008 μM) was used as a positive control and rosiglitazone (1, 0.5, 0.25, 0.125, 0.063 and 0.031 μM) was used as a negative control. 0.1% DMSO was also used as a negative control for each assay. Plates are incubated for 20 hours in a humidified incubator at 37° C. and 5% $CO_2$. After incubation, cell medium was discarded and the cells were treated with 100 μL of luciferase detection reagent for 15 minutes. Plates were analyzed using a luminometer (Victor2, Perkin Elmer). Average relative light unit (RLU) and standard deviation were analyzed using GraphPad Prism.

Figure 13:
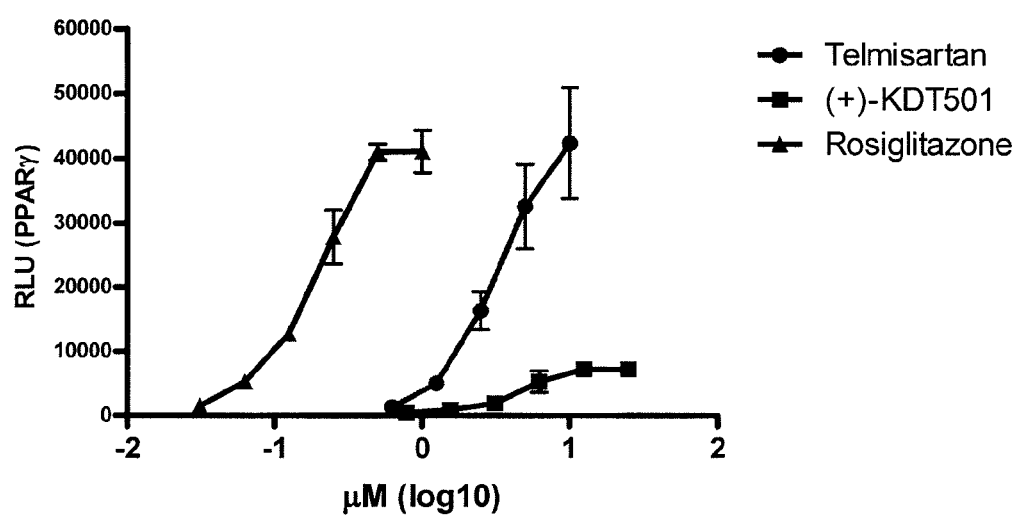
FIG. 13: Effect of (+)-KDT501 on PPARγ activity. Rosiglitazone and telmisartan were used as positive controls.
Figure 14:
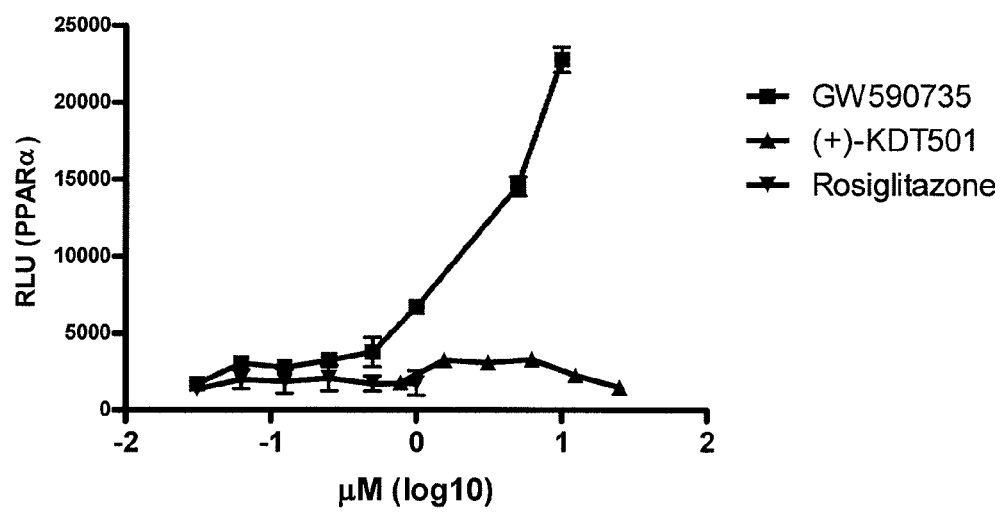
FIG. 14: Effect of (+)-KDT501 on PPARα activity. GW590735 was used as a positive control and rosiglitazone was used as a negative control.
Figure 15:
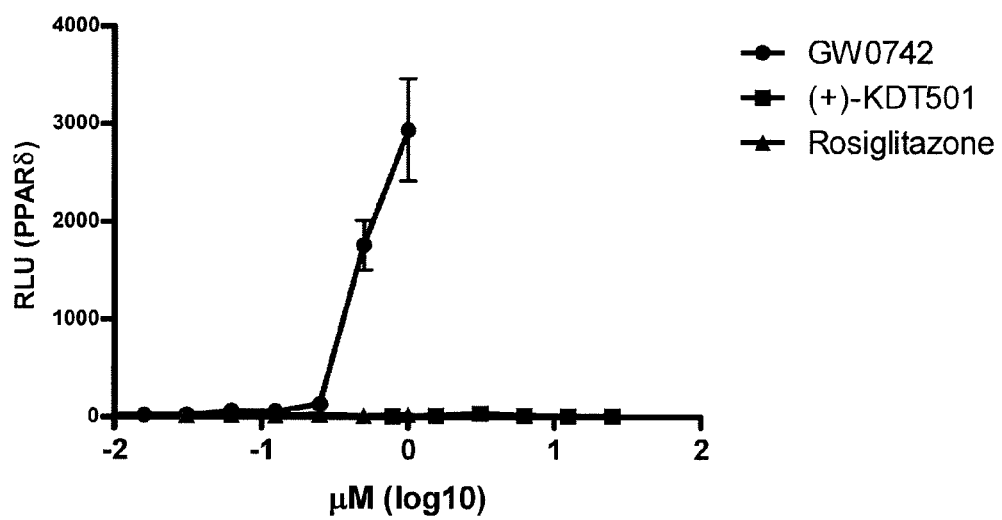
FIG. 15: Effect of (+)-KDT501 on PPARδ activity. GW0742 was used as a positive control and rosiglitazone was used as a negative control.

In the PPARγ assay, the positive agonist control (rosiglitazone) increased the activity of PPARγ as expected. Telmisartan, a known partial agonist of PPARγ, also increased PPARγ activity. (+)-KDT501 increased PPARγ activity in a statistically significant manner consistent with activity as a partial PPARγ agonist (FIG. 13). (+)-KDT501 had little or no effect on PPARα and PPARδ activity (FIGS. 14 and 15).

Figure 16:
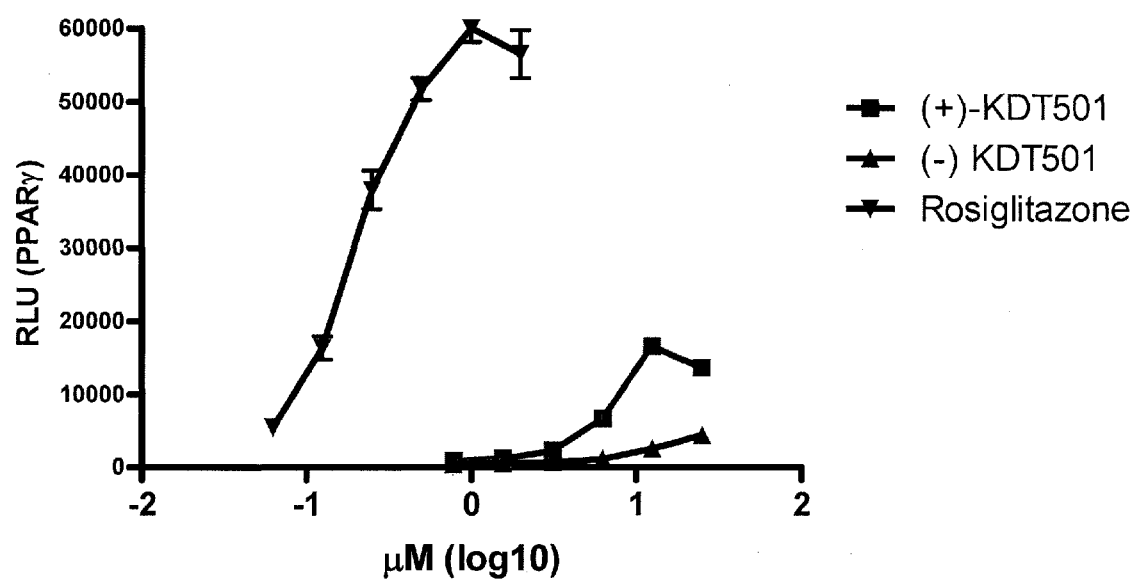
FIG. 16: Effect of (+)-KDT501 and (−)-KDT501 on PPARγ activity. Rosiglitazone was used as a positive control.

The PPAR activity assays were repeated as described above using both (+)-KDT501(12.5, 6.25, 3.125, 1.56, and 0.78 μM) and (−)-KDT501 (25, 12.5, 6.25, 3.125, 1.56, and 0.78 μM). (−)-KDT501 increased PPARγ activity, but to a significantly lesser degree than (+)-KDT501 (FIG. 16). Results for both compounds are summarized in Table 7.

TABLE 7

| Concentration of test compounds (μM) | PPARγ reporter activity (RLU) | | Fold difference | P value |
|---|---|---|---|---|
| | (+)-KDT501 | (−)-KDT501 | | |
| 25 | 13419 | 4244 | 3.2 | $8.06 \times 10^{-5}$ |
| 12.5 | 16451 | 2407 | 6.8 | $7.19 \times 10^{-4}$ |
| 6.25 | 6536 | 972 | 6.7 | $4.23 \times 10^{-3}$ |
| 3.13 | 2122 | 547 | 3.9 | $4.12 \times 10^{-3}$ |

Example 7

Effect of (+)-KDT501 on GPR120 Receptor Activity

The effect of (+)-KDT501 on GPR120 activity was evaluated using CHO-K1/GPR120/$G_{\alpha 15}$ cells that stably express GPR120. GPR120 activity was measured by intracellular calcium response.

CHO-K1/GPR120/$G_{\alpha 15}$ cells were regularly passaged to maintain optimal cell health and cultured in Ham's F12 supplemented with 10% fetal bovine serum, 200 μg/mL zeocin, and 100 μg/mL hygromycin. Cells were seeded in a 384-well black-wall, clear-bottom plate at a density of 20,000 cell per well in 20 μL of growth medium 18 hours prior to the start of the experiment, and maintained at 37° C./5% $CO_2$. Cells were loaded with calcium-4, and baseline fluorescence readings were obtained from 1 second to 20 seconds using a fluorescent imaging plate reader (FLIPR). At 20 seconds, (+)-KDT501 (5× final concentration) was added to the reading plate, and the fluorescence signal was monitored for 100 seconds (21 seconds to 120 seconds). α-linolenic acid (LA), eicosapentaenoic acid (EPA), and docosahexaenoic acid (DHA) were used as controls.

Data acquisition and analysis was performed using ScreenWorks (version 3.1) and exported to Excel. The average fluorescence value for the first 20 seconds was calculated as the baseline reading. The relative fluorescent unit (ΔRFU) intensity values were calculated with the maximal fluorescent units (21 s to 120 s), subtracting the baseline reading. Data analysis wizard written by GenScript was used to analyze $EC_{50}$. Dose response curves of antagonist were fitted using the GraphPad Prism 4 four parameter logistic equation Y=Bottom+(Top−Bottom)/(1+10^((LogIC_{50}−X)*HillSlope)), where X is the logarithm of concentration and Y is response.

Figure 17:
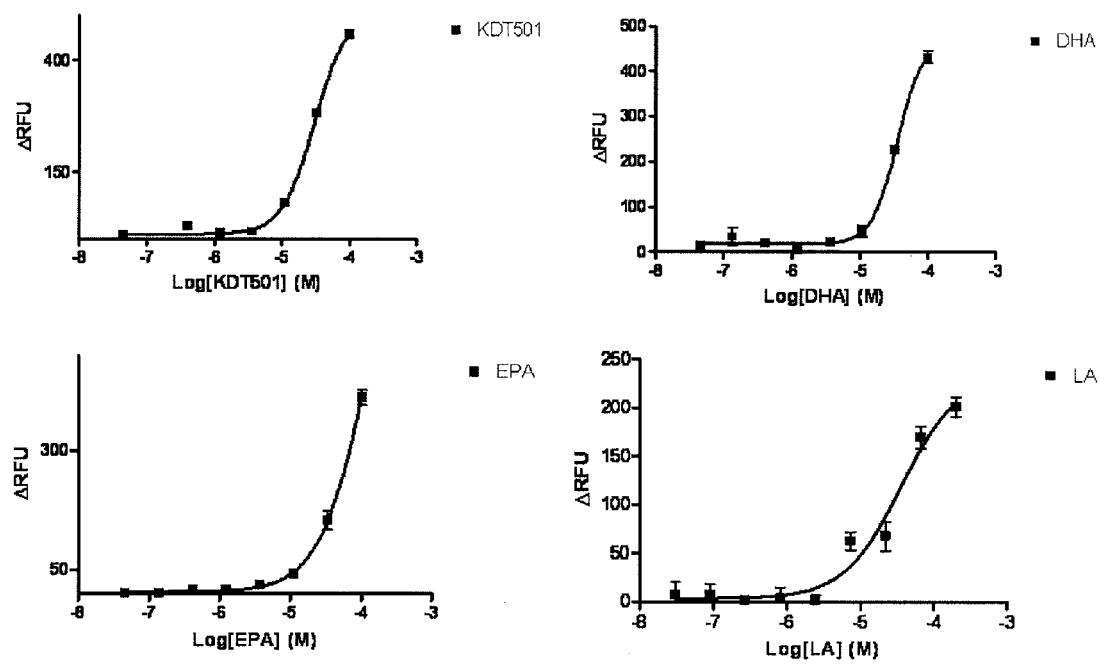
FIG. 17: Effect of (+)-KDT501 on GPR120 activity. Data represent the average +/− standard deviation of duplicate determinations. DHA, EPA, and α-LA were used as controls.

(+)-KDT501 exhibited GPR120 agonistic activity with an $EC_{50}$ value of 30.3 (FIG. 17). The $EC_{50}$ values for α-LA, DHA, and EPA were 36.1 μM, 35.3 μM and 116 μM, respectively.

Example 8

Effect of KDT501 on DAPK1 Activity

The effect of (+)-KDT501 and (−)-KDT501 on death-associated protein kinase 1 (DAPK1) activity was evaluated.

Human DAPK1 was incubated with 8 mM MOPS, pH 7.0, 0.2 mM EDTA, 250 µM ZIP peptide substrate (KKLNRTLS-FAEPG), 10 mM MgOAc, and [$\gamma$-$^{33}$P-ATP] (specific activity approximately 500 cpm/pmol, concentration as required). (+)-KDT501 or (−)-KDT501 at varying concentrations (100, 30, 10, 1, 0.3, 0.1, 0.03, 0.01 µM) were added to the reaction mixture. The reaction was initiated by addition of the MgATP mix. After incubation for 40 minutes at room temperature, the reaction was stopped by addition of 3% phosphoric acid solution. 10 µL of reaction mixture was spotted onto a P30 filtermat, washed three times for five minutes in 75 mM phosphoric acid and once in methanol prior, then dried and subjected to scintillation counting.

Figure 18:
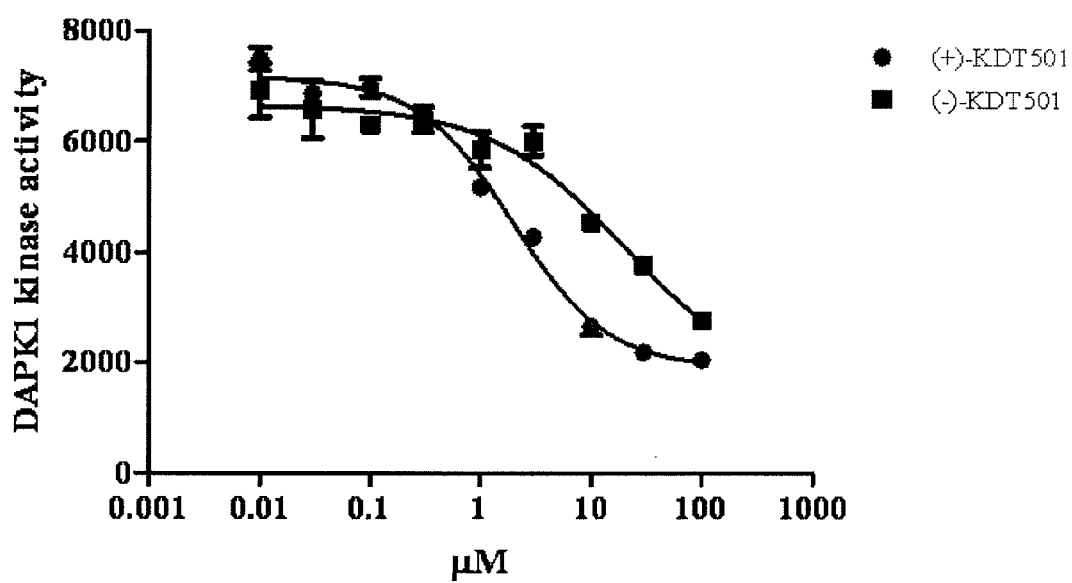
FIG. 18: Effect of (+)-KDT501 and (−)-KDT501 on DAPK1 activity in cell free assays.

Results are shown in FIG. 18. (+)-KDT501 and (−)-KDT501 inhibited DAPK1 activity in a dose-dependent manner. The calculated $IC_{50}$ values for (+)-KDT501 and (−)-KDT501 were 2.65 µM and 40.9 µM, respectively, representing approximately a 15-fold difference between the two compounds. This data suggests that (+)-KDT501 is more effective at inhibiting DAPK1 activity than (−)-KDT501.

Example 9

Effect of (+)-KDT501 on Glucose and Triglyceride Levels in a Rat Diabetes Model 64 six-week-old male Zucker diabetic fatty (ZDF) rats with glucose levels of 175-300 mg/dL were randomized and divided into eight dosing groups: 1) vehicle only (0.5% methylcellulose (w/v), 0.2% Tween 80 (w/v); negative control), 2) (+)-KDT501 25 mg/kg, 3) (+)-KDT501 50 mg/kg, 4) (+)-KDT501 100 mg/kg, 5) (+)-KDT501 200 mg/kg, 6) metformin 200 mg/kg (positive control), 7) metformin 200 mg/kg and (+)-KDT501 100 mg/kg, and 8) pioglitazone 30 mg/kg (positive control). Drugs were administered orally twice a day for 33 days.

Animals were weighed at randomization and once per week thereafter, with administration dosages calculated based on the most recent body weight measurements. Blood samples were collected by tail bleed three days prior to randomization, at randomization, and at days 15 and 29 after the start of treatment. These blood samples were used to perform whole blood glucose evaluations using a glucometer, as well as to measure blood triglyceride levels. Body composition was tested by qNMR on days 2 and 29 after the start of treatment. An oral glucose tolerance test (OGTT) was performed on days 31 and 32 after the start of treatment. Rats underwent an overnight fast prior to OGTT, and tail bleeds for glucose and insulin were performed pre-glucose bolus and at 15, 30, 60, 90, and 120 minutes post-glucose bolus. The glucose bolus was 2 g dextrose/kg of body weight. On day 33, a cardiac puncture was performed for PK analysis.

Figure 19:
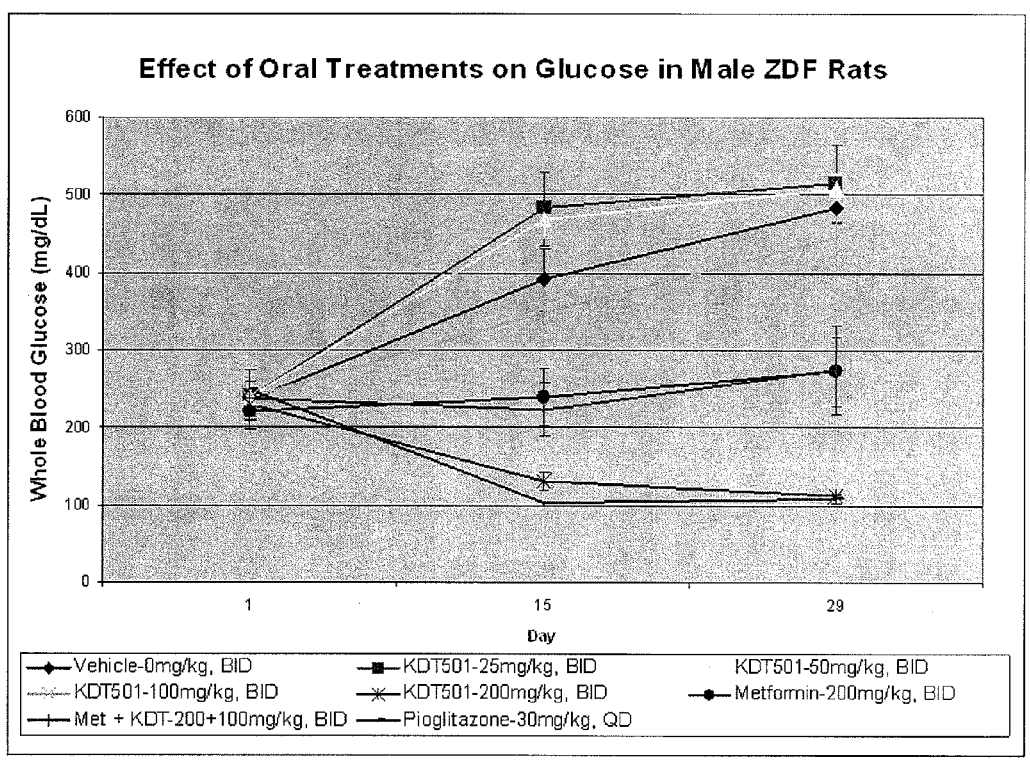
FIG. 19: Effect of KDT501 on blood glucose levels in ZDF rats.

Whole blood glucose results are set forth in FIG. 19. As expected, negative control rats exhibited a significant and steady increase in whole blood glucose levels over the course of the study. Positive control rats receiving pioglitazone showed a significant decrease in glucose levels, while positive control rats receiving metformin exhibited a slight increase in glucose levels. Rats receiving (+)-KDT501 at dosages of 25, 50, or 100 mg/kg exhibited glucose levels that were nearly the same as those observed in negative control rats. However, rats receiving (+)-KDT501 at a dosage of 200 mg/kg bid exhibited a significant decrease in glucose levels that was much greater than that observed in the metformin control rats and nearly identical to that observed in the pioglitazone control rats.

Figure 20:
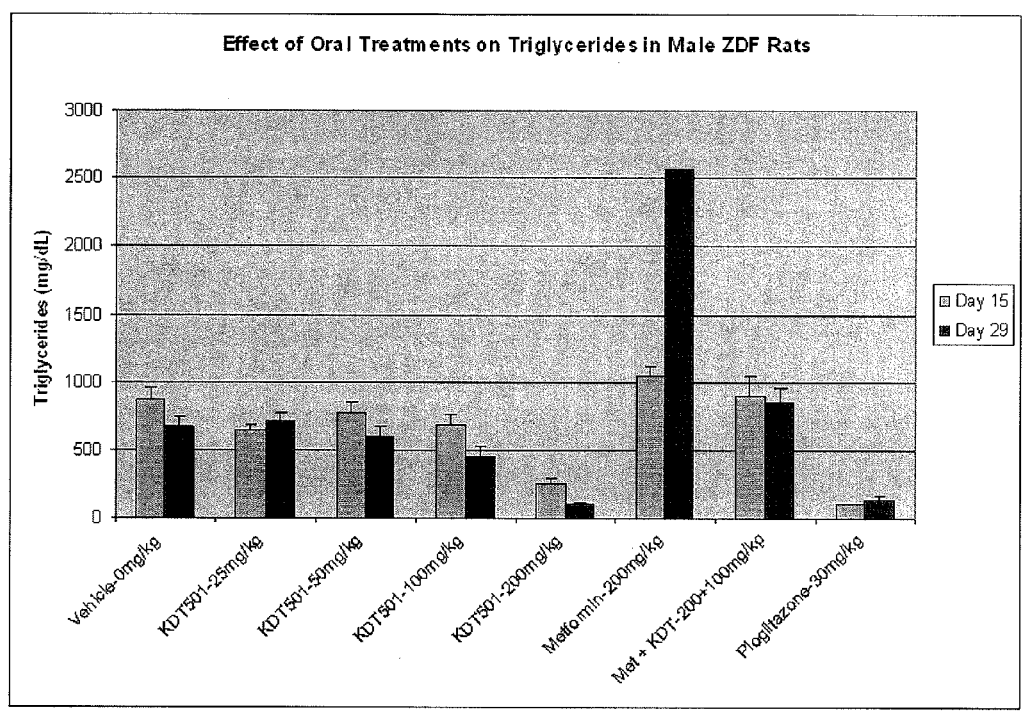
FIG. 20: Effect of KDT501 on blood triglyceride levels in ZDF rats.

Triglyceride level results are set forth in FIG. 20. Rats receiving metformin exhibited an increase in triglyceride levels at days 15 and 29 versus negative control rats, while rats receiving pioglitazone exhibited a significant decrease. Rats receiving (+)-KDT501 at dosages of 25, 50, or 100 mg/kg exhibited triglyceride levels that were similar to those observed in negative control rats. However, rats receiving (+)-KDT501 at a dosage of 200 mg/kg bid exhibited a significant decrease in triglyceride levels that was nearly as large as that observed in pioglitazone control rats.

Example 10

Effect of (+)-KDT501 on Glucose, Insulin, Hemoglobin A 1C (HbA1C) and Fat Mass in a High Fat Diet-Induced Obesity (DIO) Mouse Model 14 week-old male mice were randomized and divided into seven dosing groups with 16 animals in each group: 1) vehicle only (0.5% methylcellulose (w/v), 0.2% Tween 80 (w/v); negative control), 2) (+)-KDT501 25 mg/kg, 3) (+)-KDT501 50 mg/kg, 4) (+)-KDT501 100 mg/kg, 5) (+)-KDT501 200 mg/kg, 6) metformin 200 mg/kg (positive control), and 7) pioglitazone 30 mg/kg (positive control). Drugs were administered orally twice a day for 30 days.

Animals were weighed at randomization and once per week thereafter, with administration dosages calculated based on the most recent body weight measurements. The mice were maintained on a high fat diet (40% Kcal) (TD95217; prepared by Covance Laboratories, Greenfield, Ind.). Body composition was tested by qNMR on days −5 and 28 after the start of treatment. Blood was collected on day 29 after the start of treatment, and hemoglobin A1C (HbA1C) levels were measured. An oral glucose tolerance test (OGTT) was performed on day 30 after the start of treatment. Mice underwent an overnight fast prior to OGTT, and tail bleeds for glucose and insulin were performed pre-glucose bolus and at 15, 30, 60, 90, and 120 minutes post-glucose bolus. The glucose bolus was 2 g dextrose/kg of body weight. OGTT results were evaluated by area under the curve (AUC) measurements and Dunnett's test.

Figure 21:
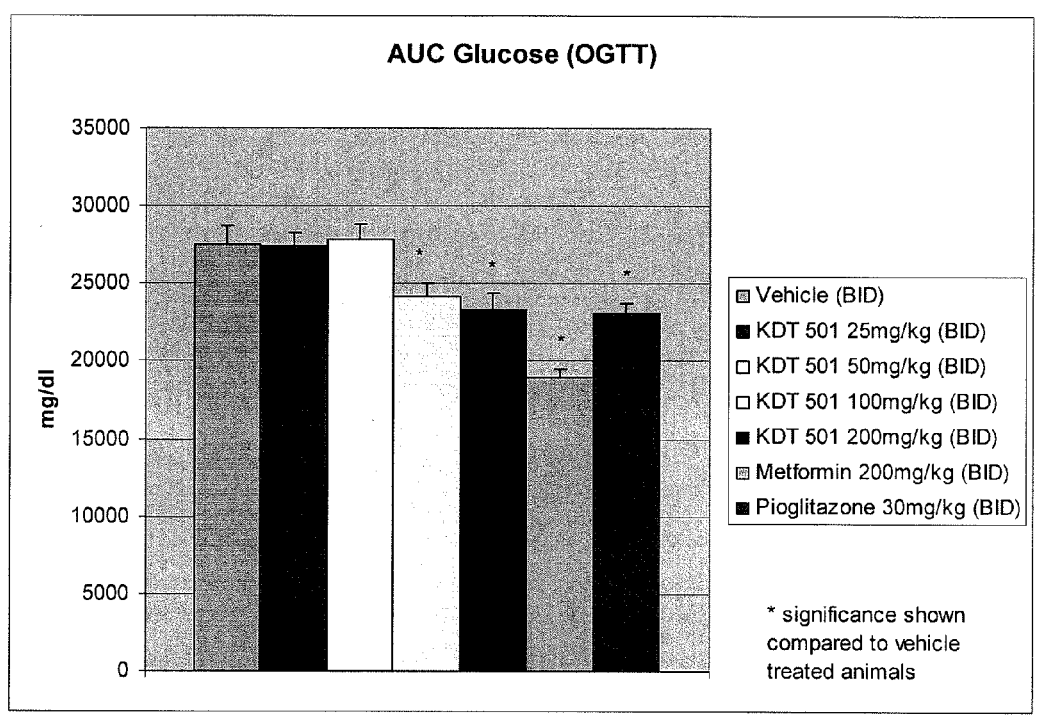
FIG. 21: Effect of KDT501 on blood glucose levels in DIO mice.

Blood glucose results from the OGTT are set forth in FIG. 21. Positive control mice receiving pioglitazone or metformin exhibited a significant decrease in glucose levels. Similarly, mice receiving (+)-KDT501 at dosages of 100 or 200 mg/kg exhibited a significant decrease in glucose levels.

Figure 22:
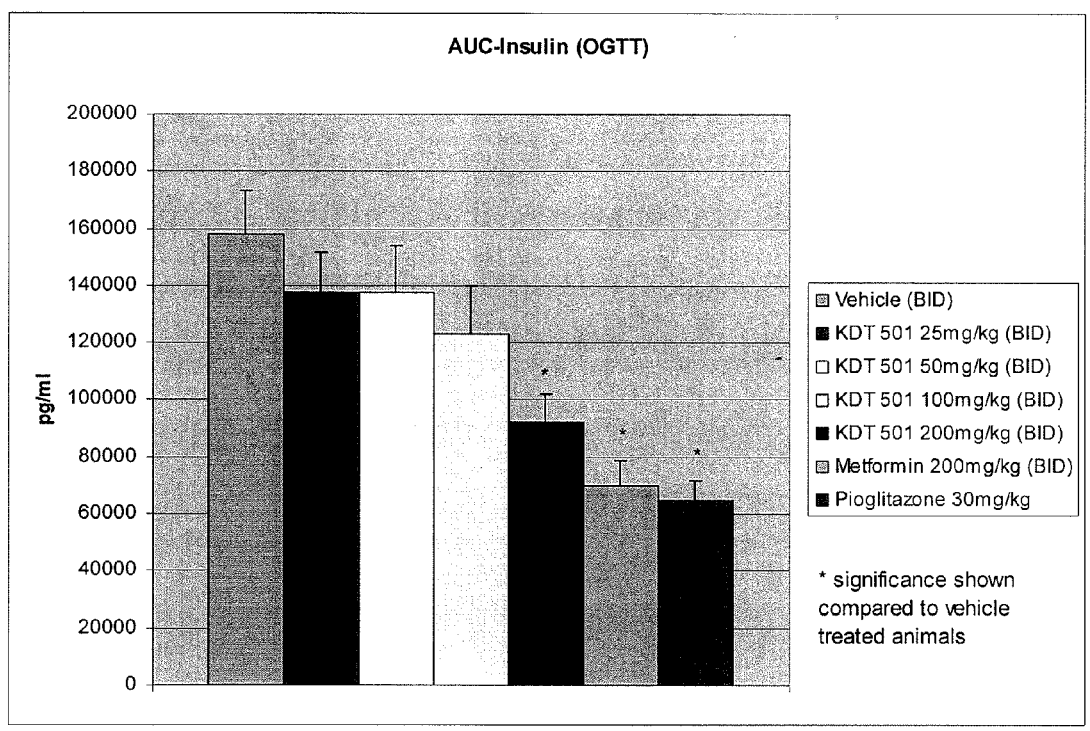
FIG. 22: Effect of KDT501 on blood insulin levels in DIO mice.

Insulin results from the OGTT are set forth in FIG. 22. Positive control mice receiving pioglitazone or metformin exhibited a significant decrease in insulin levels. Similarly, mice receiving (+)-KDT501 at a dosage of 200 mg/kg exhibited a significant decrease in insulin levels.

Figure 23:
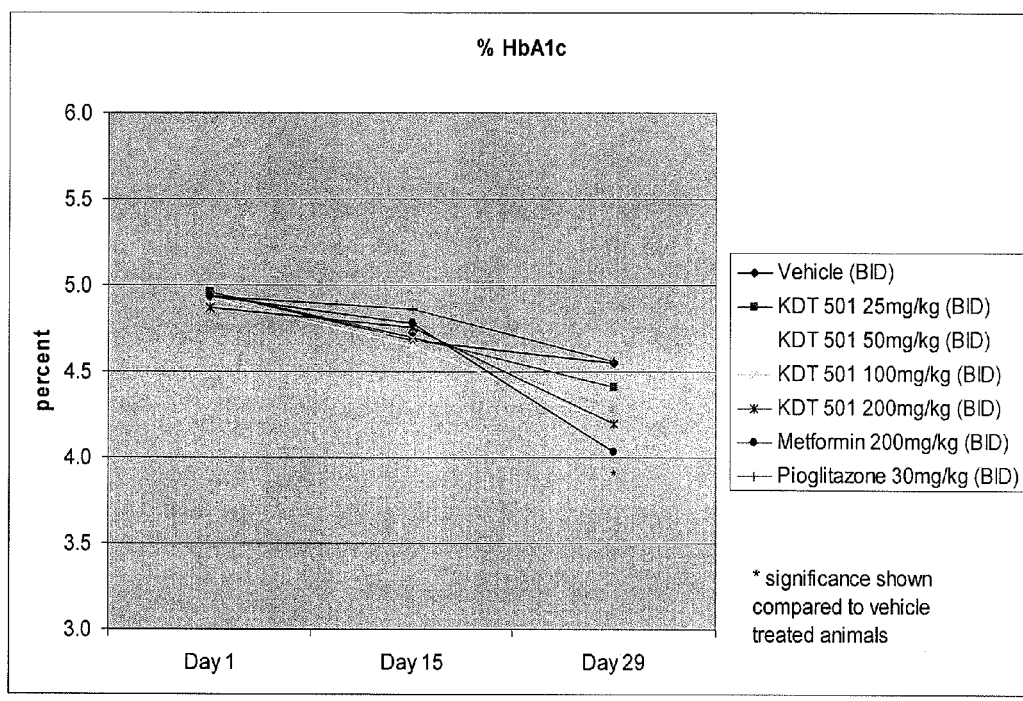
FIG. 23: Effect of KDT501 on HbA1C levels in DIO mice.

HbA1C results are set forth in FIG. 23. A significant difference in HbA1C was observed between the vehicle-only negative control and positive control metformin dosing groups. Administration of (+)-KDT501 resulted in a trend towards HbA1C inhibition.

Figure 24:
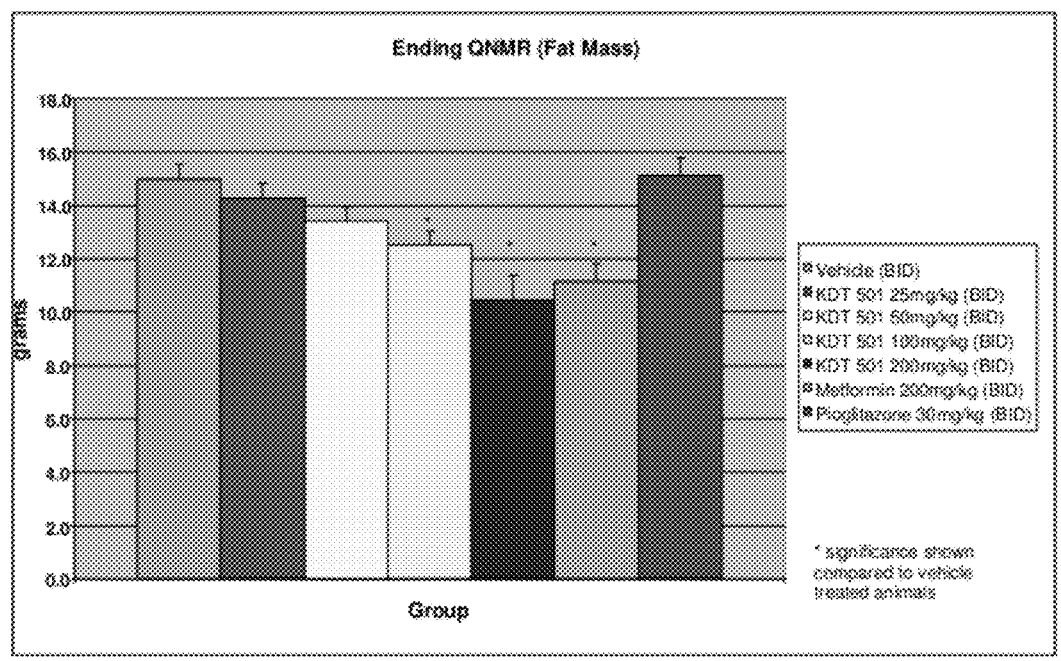
FIG. 24: Effect of KDT501 on fat mass in DIO mice.

Fat mass results are set forth in FIG. 24. Positive control mice receiving metformin exhibited a reduction in fat mass, while positive control mice receiving pioglitazone exhibited no difference. Administration of (+)-KDT501 at 100 or 200 mg/kg resulted in a significant difference in fat mass versus negative control mice.

Example 11

Asymmetric Synthesis of (+)-KDT500 or (−)-KDT500 from Lupulone

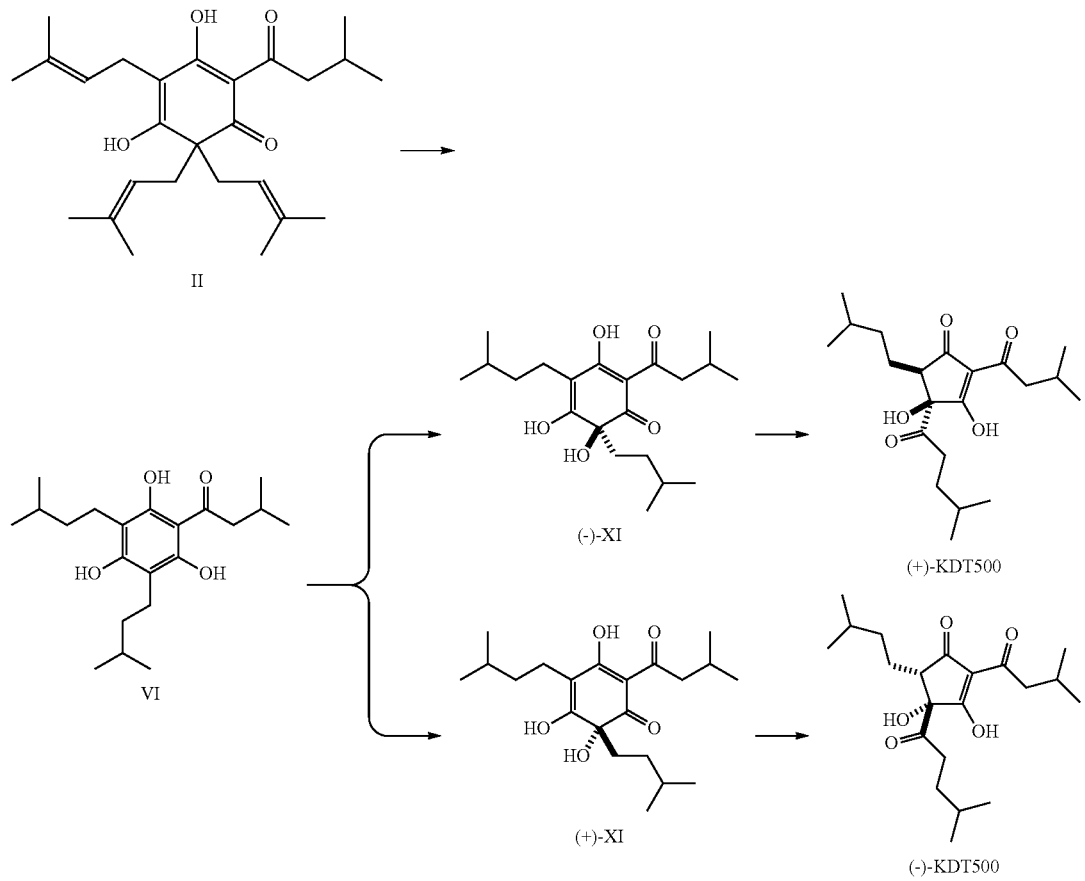

Scheme II

Step 1: Synthesis of tetrahydro deoxyhumulone (VI) from lupulone (II).

A 10% solution (w/v) of lupulone in methanol is prepared. A catalytic amount of concentrated HCl (aq) and 10% Pd/C is added. The resulting mixture is stirred under hydrogen (1.1 atm) for 3 hours, and the reaction monitored by HPLC. After the reaction is complete, the catalyst is removed via filtration, and the filtrate is concentrated in vacuo to render tetrahydro deoxyhumulone (VI), which can be used for the next reaction without further purification.

Step 2A: Asymmetric Synthesis of (−)-tetrahydro humulone ((−)-XI) from tetrahydro deoxyhumulone (VI).

Option 2A(i): Asymmetric Synthesis of (−)-tetrahydro humulone ((−)-XI) from tetrahydro deoxyhumulone (VI).

A 14% (w/v) solution of tetrahydro deoxyhumulone (VI) in anhydrous THF is prepared and cooled to −78° C. using an acetone/dry ice bath. Diisopropylethylamine (DIEA) (1.2 eq) is chilled and added drop-wise to the solution of (VI). This solution is transferred via cannula into the [(−)-sparteine]$_2$-Cu$_2$—O$_2$ complex) in THF derived from 2.2 eq Cu(CH$_3$CN)$_4$ PF$_6$ and 2.3 eq of diamine ligand under argon at −78° C. The resulting mixture is stirred at −78° C. or the desired temperature for 16 hours. The reaction is quenched with 4 volumes of 5% (by weight) aqueous sulfuric acid. The mixture is extracted with ethyl acetate (×3), and the combined extracts are washed with 5% sulfuric acid, water, and brine, dried over sodium sulfate, and concentrated in vacuo (Dong 2008).

Option 2A(ii): Asymmetric Synthesis of (−)-tetrahydro humulone ((−)-XI) from tetrahydro deoxyhumulone (VI).

A suitable P450 mutant enzyme capable of converting tetrahydro deoxyhumulone (VI) to (−)-tetrahydro humulone ((−)-XI) is constructed and purified as described in U.S. Pat. No. 7,704,715 and references contained therein. A typical reaction contains 1-4 µM purified P450 heme domain enzyme and 1-2 mM tetrahydro deoxyhumulone (VI) in 500 µL 100 mM tris-HCl, pH 8.2. The following are combined: 713 µL purified water, 200 µL 0.100 M tris-HCl pH 8.2, 100 mM final concentration, 2 µL tetrahydro deoxyhumulone (VI) in DMSO (1 mM final concentration).

The reaction is initiated by addition of 1-10 mM H$_2$O$_2$ and monitored by via HPLC for the maximum conversion. The reaction is stopped by addition of 7.5 µL 6M HCl. The (−)-tetrahydro humulone ((−)-XI) is obtained via an extractive work-up and purified as previously described.

Option 2A(iii): Asymmetric Synthesis of (−)-tetrahydro humulone ((−)-XI) from tetrahydro deoxyhumulone (VI).

A microbe capable of converting tetrahydro deoxyhumulone (VI) to (−)-tetrahydro humulone ((−)-XI) is produced according to US Patent Publ. No. 2010/0144547 and references contained therein. This microbe is grown in the presence of tetrahydro deoxyhumulone (VI) according to the following fermentation conditions: 500 mL culture with LB media with 30 mg/L kanamycin. At $OD_{600}$ of 1.0, cells are concentrated to a final $OD_{600}$ of 5.0 and induced with 1 mM IPTG. Tetrahydro deoxyhumulone (VI) is added to a final concentration of 1 mM and 4 mM. At different timepoints, culture samples are collected, centrifuged, filtered, and injected on to HPLC (54) and a maximum conversion is determined. Following maximum conversion, the broth is acidified to pH of 2.0, extracted with ethyl acetate, dried, and re-dissolved in hexanes. The (−)-tetrahydro humulone ((−)-XI) is obtained via an extractive work-up and purified as previously described.

A variety of fermentation media such as LB, F1 or TB fermentation media well known in the art which can be used or adapted for use with embodiments of the invention disclosed herein including LB, TB and F1 media. Further media tailored to growing organisms such as *A. terreus* and *M. pilosus* are also well known in the art (see, e.g. Miyake 2006; Hajjaj 2001).

Step 2B: Asymmetric Synthesis of (+)-tetrahydro humulone ((+)-XI) from tetrahydro deoxyhumulone (VI).

Option 2B(i): Asymmetric Synthesis of (+)-tetrahydro humulone ((+)-XI) from tetrahydro deoxyhumulone (VI).

A 14% (w/v) solution of tetrahydro deoxyhumulone (VI) in anhydrous THF is prepared and cooled to −78° C. using an acetone/dry ice bath. Diisopropylethylamine (DIEA) (1.2 eq) is chilled and added drop-wise to the solution of (VI). This solution is transferred via cannula into the [(+)-sparteine]$_2$-Cu$_2$—O$_2$ complex) in THF derived from 2.2 eq Cu(CH$_3$CN)$_4$PF$_6$ and 2.3 eq of diamine ligand under argon at −78° C. The resulting mixture is stirred at −78° C. or the desired temperature for 16 hours. The reaction is quenched with 4 volumes of 5% (by weight) aqueous sulfuric acid. The mixture is extracted with ethyl acetate (×3), and the combined extracts are washed with 5% sulfuric acid, water, and brine, dried over sodium sulfate, and concentrated in vacuo (Dong 2008).

Option 2B(ii): Asymmetric Synthesis of (+)-tetrahydro humulone ((+)-XI) from tetrahydro deoxyhumulone (VI).

A P450 mutant enzyme capable of converting tetrahydro deoxyhumulone (VI) to (+)-tetrahydro humulone ((+)-XI) is constructed and purified as described in U.S. Pat. No. 7,704,715 and references contained therein. A typical reaction contains 1-4 µM purified P450 heme domain enzyme and 1-2 mM tetrahydro deoxyhumulone (VI) in 500 µL 100 mM Tris-HCl, pH 8.2. The following are combined: 713 µl purified water, 200 µL 0.100 M tris-HCl pH 8.2, 100 mM final concentration, 2 µL tetrahydro deoxyhumulone (VI) in DMSO (1 mM final concentration).

The reaction is initiated by addition of 1-10 mM $H_2O_2$ and monitored via HPLC for the maximum conversion. The reaction is stopped by addition of 7.5 µL 6M HCl. The (+)-tetrahydro humulone ((+)-XI) is obtained via an extractive work-up and purified as previously described.

Option 2B(iii): Asymmetric Synthesis of (+)-tetrahydro humulone ((+)-XI) from tetrahydro deoxyhumulone (VI).

A microbe capable of converting tetrahydro deoxyhumulone (VI) to (+)-tetrahydro humulone ((+)-XI) is produced according to US Patent Publ. No. 2010/0144547 and references contained therein. The microbe is grown in the presence of tetrahydro deoxyhumulone (VI) according to the following fermentation conditions: 500 mL culture with LB media with 30 mg/L kanamycin. At $OD_{600}$ of 1.0, cells were concentrated to a final $OD_{600}$ of 5.0 and induced with 1 mM IPTG. Tetrahydro deoxyhumulone (VI) is added to a final concentration of 1 mM and 4 mM. At different timepoints, culture samples are collected, centrifuged, filtered, and injected on to HPLC (5 µL) and a maximum conversion is determined. Following maximum conversion, the broth is acidified to pH of 2.0, extracted with ethyl acetate, dried and re-dissolved in hexanes. The (−)-tetrahydro humulone is obtained via an extractive work-up and purified as previously described.

A variety of fermentation media such as LB, F1 or TB fermentation media well known in the art can be used or adapted for use with embodiments of the invention disclosed herein including LB, TB and F1 media. Further media tailored to growing organisms such as *A. terreus* and *M. pilosus* are also well known in the art (see, e.g. Miyake 2006; Hajjaj 2001).

Step 3A: Asymmetric Synthesis of (+)-KDT500 from (−)-tetrahydro humulone ((−)-XI).

A 50% (w/v) solution of (−)-tetrahydrohumulone ((−)-XI) in water is prepared and warmed to 85° C. with stirring in a sealed vessel. MgSO$_4$ (0.6 eq) is added to the solution over 5 minutes with continuous stirring. To the sealed vessel, a KOH solution (38.25% (w/v), 1.0 eq) is added drop-wise with stirring. The reaction temperature is held at 85° C. for the next 3 hours or until the isomerization is complete as judged by HPLC. The free acid of (+)-KDT-500 is formed by adding 2 volumes of isopropanol, 2 volumes of water and 1 equivalent of $H_2SO_4$ to the reaction mixture. This mixture is mixed until fully homogenous at which point 2 volumes of dichloromethane are used to extract the reaction mixture (3×). The organic extract is concentrated in vacuo, redissolved in hexanes, dried over Na$_2$SO$_4$, filtered, concentrated in vacuo and dried overnight at 0.070 mbar. The end product is the free acid form of (+) KDT-500. Further purification may be carried out via epimerization, chromatography, complexation, and/or crystallization.

Step 3B: Asymmetric Synthesis of (−)-KDT500 from (+)-tetrahydro humulone ((+)-XI).

A 50% (w/v) solution of (+)-tetrahydrohumulone ((+)-XI) in water is prepared and warmed to 85° C. with stirring in a sealed vessel. MgSO$_4$ (0.6 eq) is added to the solution over 5 minutes with continuous stirring. To the sealed vessel, a KOH solution (38.25% (w/v), 1.0 eq) is added drop-wise with stirring. The reaction temperature is held at 85° C. for the next 3 hours or until the isomerization is complete as judged by HPLC. The free acid of (−)-KDT-500 is formed by adding 2 volumes of isopropanol, 2 volumes of water and 1 equivalent of $H_2SO_4$ to the reaction mixture. This mixture is mixed until fully homogenous at which point 2 volumes of dichloromethane is used to extract the reaction mixture (3×). The organic extract is concentrated in vacuo, redissolved in hexanes, dried over Na$_2$SO$_4$, filtered, concentrated in vacuo and dried overnight at 0.070 mbar. The end product is the free acid form of (−) KDT-500. Further purification may be carried out via epimerization, chromatography, complexation and/or crystallization.

Example 12

Asymmetric Synthesis of Either (+)-KDT500 or (−)-KDT500 from Deoxyhumulone

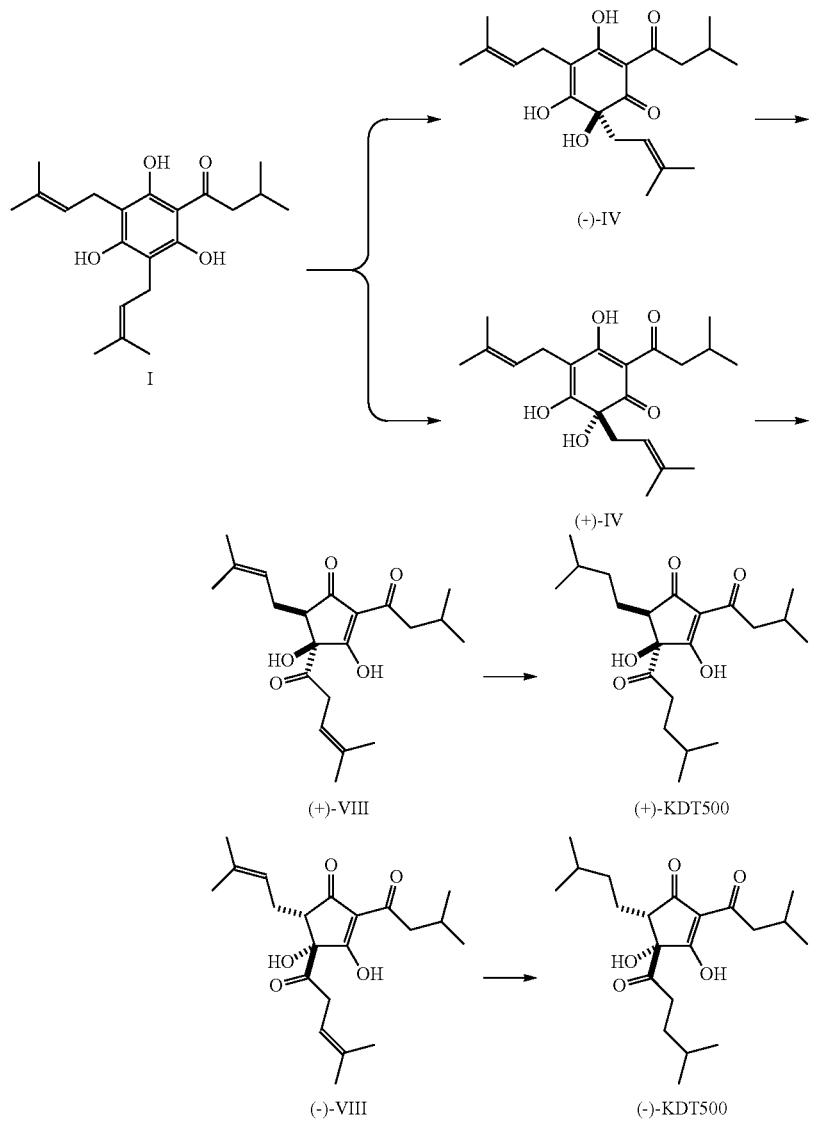

Step 1A: Asymmetric Synthesis of (−)-humulone ((−)-IV) from deoxyhumulone (I).

Option 1A(i): Asymmetric Synthesis of (−)-humulone ((−)-IV) from deoxyhumulone (I).

A 14% (w/v) solution of deoxyhumulone (I) in anhydrous THF is prepared and cooled to −78° C. using an acetone/dry ice bath. Diisopropylethylamine (DIEA) (1.2 eq) is chilled and added drop-wise to the solution of (VI). This solution is transferred via cannula into the [(−)-sparteine]$_2$-Cu$_2$—O$_2$ complex) in THF derived from 2.2 eq Cu(CH$_3$CN)$_4$ PF$_6$ and 2.3 eq of diamine ligand under argon at −78° C. The resulting mixture is stirred at −78° C. or the desired temperature for 16 hours. The reaction is quenched with 4 volumes of 5% (by weight) aqueous sulfuric acid. The mixture is extracted with ethyl acetate (×3), and the combined extracts are washed with 5% sulfuric acid, water, and brine, dried over sodium sulfate, and concentrated in vacuo (Dong 2008).

Option 1A(ii): Asymmetric Synthesis of (−)-humulone ((−)-IV) from deoxyhumulone (I).

A P450 mutant enzyme capable of converting deoxyhumulone (I) to (−)-humulone ((−)-IV) is constructed and purified as described in U.S. Pat. No. 7,704,715 and references contained therein. A typical reaction contains 1-4 μM purified P450 heme domain enzyme and 1-2 mM humulone (I) in 500 μL 100 mM tris-HCl, pH 8.2. The following are combined: 713 μL purified water, 200 μL 0.100 M tris-HCl pH 8.2, 100 mM final concentration, 2 μL deoxyhumulone (I) in DMSO (1 mM final concentration).

The reaction is initiated by the addition of 1-10 mM H$_2$O$_2$ and monitored via HPLC for the maximum conversion. The reaction is stopped by addition of 7.5 μL 6M HCl. The (−)-humulone ((−)-IV) is obtained via an extractive work-up and purified as previously described.

Option 1A(iii): Asymmetric Synthesis of (−)-humulone ((−)-IV) from deoxyhumulone (I).

A microbe capable of converting humulone (I) to (−)-humulone ((−)-IV) is produced according to US Patent Publ. No. 2010/0144547 and references contained therein. This microbe is then grown in the presence of deoxyhumulone (I) according to the following fermentation conditions: 500 mL culture with LB media with 30 mg/L kanamycin. At $OD_{600}$ of 1.0, cells are concentrated to a final $OD_{600}$ of 5.0 and induced with 1 mM IPTG. Deoxyhumulone (I) is added to a final concentration of 1 mM and 4 mM. At different timepoints, culture samples are collected, centrifuged, filtered, and injected on to HPLC (5 μL) and a maximum conversion is determined. Following maximum conversion, the broth is acidified to pH of 2.0, extracted with ethyl acetate, dried and re-dissolved in hexanes. The (−)-humulone ((−)-IV) is obtained via an extractive work-up and purified as previously described.

A variety of fermentation media such as LB, F1 or TB fermentation media well known in the art can be used or adapted for use with embodiments of the invention disclosed herein including LB, TB and F1 media. Further media tailored to growing organisms such as *A. terreus* and *M. pilosus* are also well known in the art (see, e.g. Miyake 2006; Hajjaj 2001).

Step 1B: Asymmetric Synthesis of (+)-humulone ((+)-IV) from deoxyhumulone (I).

Option 1B(i): Asymmetric Synthesis of (+)-humulone ((+)-IV) from deoxyhumulone (I).

A 14% (w/v) solution of deoxyhumulone (I) in anhydrous THF is prepared and cooled to −78° C. using an acetone/dry ice bath. Diisopropylethylamine (DIEA) (1.2 eq) is chilled and added drop-wise to the solution of (VI). This solution is transferred via cannula into the [(+)-sparteine]$_2$-Cu$_2$—O$_2$ complex) in THF derived from 2.2 eq Cu(CH$_3$CN)$_4$ PF$_6$ and 2.3 eq of diamine ligand under argon at −78° C. The resulting mixture is stirred at −78° C. or the desired temperature for 16 hours. The reaction is quenched with 4 volumes of 5% (by weight) aqueous sulfuric acid. The mixture is extracted with ethyl acetate (×3), and the combined extracts are washed with 5% sulfuric acid, water, and brine, dried over sodium sulfate, and concentrated in vacuo (Dong 2008).

Option 1B(ii): Asymmetric Synthesis of (+)-humulone ((+)-IV) from deoxyhumulone (I).

A P450 mutant enzyme capable of converting deoxyhumulone (I) to (+)-humulone ((+)-IV) is constructed and purified as described in U.S. Pat. No. 7,704,715 and references contained therein. A typical reaction contains 1-4 μM purified P450 heme domain enzyme and 1-2 mM humulone (I) in 500 μA, 100 mM tris-HCl, pH 8.2. The following are combined: 713 μl purified water, 200 μL 0.100 M tris-HCl pH 8.2, 100 mM final concentration, 2 μL deoxyhumulone (I) in DMSO (1 mM final concentration).

The reaction is initiated by addition of 1-10 mM $H_2O_2$ and monitored via HPLC for the maximum conversion. The reaction is stopped by addition of 7.5 μL 6M HCl. The (+)-humulone ((+)-IV) is obtained via an extractive work-up and purified as previously described.

Option 1B(iii): Asymmetric Synthesis of (+)-humulone ((+)-IV) from deoxyhumulone (I).

A microbe capable of converting deoxyhumulone (I) to (+)-humulone ((+)-IV) is produced according to US Patent Publ. No. 2010/0144547 and references contained therein. This microbe is then grown in the presence of (+)-humulone ((+)-IV) according to the following fermentation conditions: 500 mL culture with LB media with 30 mg/L kanamycin. At $OD_{600}$ of 1.0, cells are concentrated to a final $OD_{600}$ of 5.0 and induced with 1 mM IPTG. Deoxyhumulone (I) is added to a final concentration of 1 mM and 4 mM. At different timepoints, culture samples are collected, centrifuged, filtered, and injected on to HPLC (5 μL) and a maximum conversion is determined. Following maximum conversion, the broth is acidified to pH of 2.0, extracted with ethyl acetate, dried and re-dissolved in hexanes. The (+)-humulone ((+)-IV) is obtained via an extractive work-up and purified as previously described.

A variety of fermentation media such as LB, F1 or TB fermentation media well known in the art can be used or adapted for use with embodiments of the invention disclosed herein including LB, TB and F1 media. Further media tailored to growing organisms such as *A. terreus* and *M. pilosus* are also well known in the art (see, e.g. Miyake 2006; Hajjaj 2001).

Step 2A: Asymmetric Synthesis of (+)-cis isohumulone ((+)-VIII) from (−)-humulone ((−)-IV) (RTP: K008-49)

98.9 mg of (−)-humulone ((−)-IV) was diluted with 1704 of water and warmed to 85° C. with stirring in a capped 4 mL vial. 19.8 mg (0.6 eq) of MgSO$_4$ was added, and stirring was continued for 5 minutes. 31 μL (1.03 eq) of a 38.25% (w/v) KOH solution was added to the solution, and the reaction was allowed to proceed at 85° C. for the next 3 hours, at which point the reaction was complete as judged by HPLC. The resulting product was used to generate either the free acid or Mg salt of (+)-cis isohumulone ((+)-VIII).

The free acid of (+)-cis isohumulone ((+)-VIII) was formed by adding 0.5 mL of isopropanol, 0.5 mL of water and 1 equivalent of $H_2SO_4$ to the reaction mixture. This mixture was mixed until fully homogenous at which point 0.5 mL of dichloromethane was used to extract the reaction mixture 3 times. The organic extract was concentrated in vacuo, re-dissolved in hexanes, dried over Na$_2$SO$_4$, filtered and concentrated in vacuo and dried overnight at 0.070 mbar, resulting in the free acid form of (+)-cis isohumulone ((+)-VIII).

The Mg salt of (+)-cis isohumulone ((+)-VIII) was formed by removing the reaction mixture from heat and adding 0.5 mL of ethyl acetate with stirring until fully dissolved. 0.5 mL of water was added to separate the aqueous and organic layers and to extract the ethyl acetate. The ethyl acetate extraction was repeated 2 additional times, and the extract was concentrated in vacuo and dried overnight at 0.070 mbar. The final product was Mg salt of (+)-cis isohumulone ((+)-VIII), along with a small amount of salt impurities. Further purification may be carried via epimerization, crystallization and/or complexation to remove all (−)-trans isohumulone.

Step 2B: Asymmetric Synthesis of (−)-cis isohumulone ((−)-VIII) from (+)-humulone ((+)-IV).

1431 mg of (+)-humulone ((+)-IV) was diluted with 1 mL of water and warmed to 80° C. with stirring in a capped 4 mL vial. 273 mg (0.6 eq) of MgSO$_4$ was added, and stirring was continued for 5 minutes. 430 μL (1.0 eq) of a 38.25% (w/v) KOH solution was added to the solution, and the reaction is allowed to proceed at 80° C. for the next 6 hours, at which point the reaction was complete as judged by HPLC. The resulting product can be used to generate either the free acid or Mg salt of (−)-cis isohumulone ((−)-VIII). In this case, the reaction mixture was kept in solution and taken directly to (−) KDT 500 via step 3B below.

The free acid of (−)-cis isohumulone ((−)-VIII) is formed by adding 2 volumes of isopropanol, 2 volumes of water and 1 equivalent of $H_2SO_4$ to the reaction mixture. This mixture is mixed until fully homogenous, at which point 2 volumes of dichloromethane is used to extract the reaction mixture (3×). The organic extract is concentrated in vacuo, re-dissolved in hexanes, dried over $Na_2SO_4$, and filtered and concentrated in vacuo and dried overnight at 0.070 mbar, resulting in the free acid form of (−)-cis isohumulone ((−)-VIII).

The Mg salt of (−)-cis isohumulone ((−)-VIII) is formed by removing the reaction mixture from heat and adding 2 volumes of ethyl acetate with stirring until fully dissolved. 2 volumes of water is added to separate the aqueous and organic layers and to extract the ethyl acetate. This ethyl acetate extraction is repeated 2 more times, and the extract is concentrated in vacuo and dried overnight at 0.070 mbar, resulting in the Mg salt of (−)-cis isohumulone ((−)-VIII), along with a small amount of salt impurities. Further purification may be carried out via epimerization, crystallization, chromatography, and/or complexation to remove all (+)-trans isohumulone.

Step 3A: Synthesis of (+)-KDT500 from (+)-cis isohumulone ((+)-VIII) (RTP: K008-50)

96.3 mg of the dry Mg salt of (+)-cis isohumulone ((+)-VIII) was dissolved in 1 mL of methanol. 3.1 mg (0.3 eq) of MgO was added, and the reaction mixture was stirred for five minutes. 30 mg of 10% Pd/C was added to the solution, and stirring was resumed. A hydrogen atmosphere was introduced by bubbling hydrogen gas into the solution. After 45 minutes the reaction was judged to be complete by HPLC, the stirring was stopped, and the hydrogen atmosphere was removed by opening the vial. 1 equivalent of sulfuric acid was added to the reaction mixture (pH ~1), and the reaction was filtered through a 0.2 mm syringe filter. The reaction vessel and filter were washed 2 times successively with ethyl acetate. The filtrate was concentrated in vacuo, redissolved in hexanes, dried over $Na_2SO_4$, filtered via a cotton pipette, and concentrated in vacuo and dried overnight at 0.070 mbar. 58.1 mg of (+)-KDT-500 was produced. Further purification was carried out via chromatography and crystallization.

Step 3B: Synthesis of (−)-KDT500 from (−)-cis isohumulone ((−)-VIII).

The reaction mixture of Step 2B (~1.4 g of (−)-cis isohumulone) was dissolved in 10 mL of methanol and 256 mg of MgO was added and the reaction mixture was stirred for five minutes. The solution was filtered and split into 2 equal stocks by volume. 34 mg of MgO was added to "Reaction 1" followed by 200 mg of 10% Pd/C and the stirring was resumed. A hydrogen atmosphere was introduced by bubbling hydrogen gas into the solution. After 1 hour the reaction was judged to be complete by HPLC, the stirring was stopped, and the hydrogen atmosphere was removed by opening the vial. 1 equivalent of sulfuric acid was added to the reaction mixture (pH ~1), and the reaction was filtered through a 0.2 mm syringe filter. The reaction vessel and filter were washed 2 times successively with ethyl acetate. The filtrate was concentrated in vacuo, redissolved in hexanes, dried over $Na_2SO_4$, filtered via a cotton pipette, concentrated in vacuo, and dried overnight at 0.070 mbar. 933.5 mg of (−)-KDT-500 was produced after from the combination of both reactions. Further purification was carried out via chromatography and crystallization.

Example 13

Preparation of (+)-Humulone and (−)-Humulone from (−)-Humulone and Deoxy Humulone, Respectively

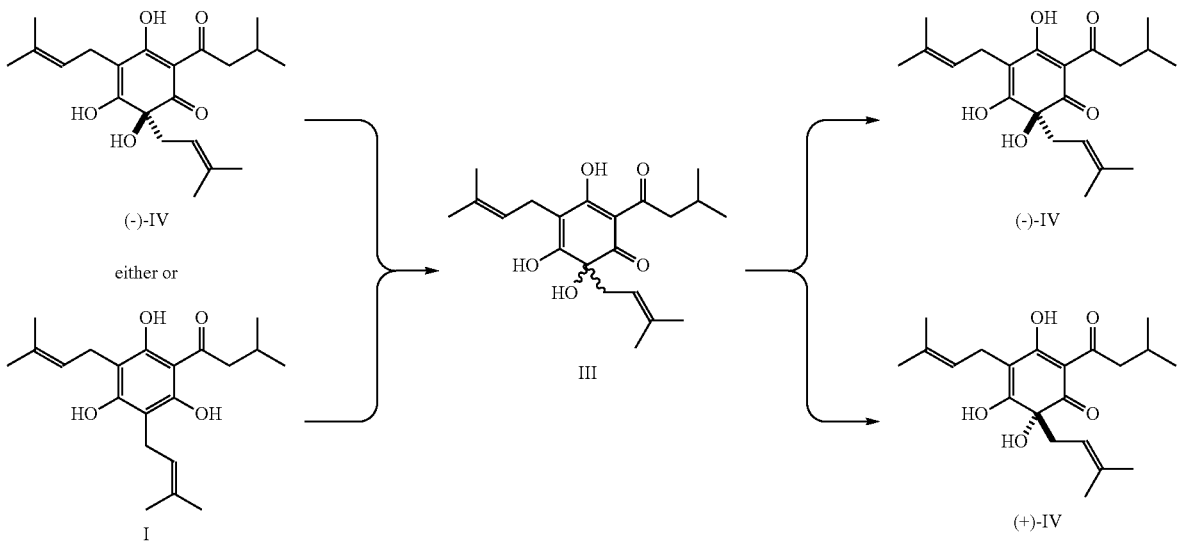

Scheme IV

Step 1: Synthesis of racemic (±)-humulone (III).

Option 1A: Synthesis of racemic (±)-humulone (III) from (−)-humulone ((−)-IV).

Pure (−)-humulone was dissolved in pinene or other suitable solvent (inert high boiling alkane, e.g., limonene, trimethylhexane) to form a 3-10% solution. This solution was placed in a pressure tube, purged with argon or nitrogen to remove all oxygen, sealed, and heated at 125 to 145° C., for 1-20 hours. The reaction was then allowed to cool to room temperature, the solvent was removed in vacuo, and racemic (±)-humulone (III) was purified, if needed, as described elsewhere.

Option 1B: Synthesis of racemic (±)-humulone (III) from deoxyhumulone (I).

Deoxyhumulone (I) is dissolved completely in methanol, and 1 eq of lead acetate is added to this solution followed by a catalytic amount (0.1 eq) of 10% Pd/C. The solution is stirred and bubbled with air. After approximately 4 hours, the lead salt is separated via filtration, and additional lead acetate is added to the filtrate to ensure complete recovery of the racemic (±)-humulone (III) as the lead salt. All of the lead salt (canary yellow) is collected and suspended in methanol followed by the addition of sulfuric acid to the solution. The lead sulfate forms an insoluble precipitate that is removed via centrifugation. The homogenous methanol solution is extracted between hexanes and water (roughly 2 volumes of each). The racemic (±)-humulone (III) is extracted into hexanes and concentrated in vacuo to yield the free acid form of the racemic (±)-humulone (III).

Step 2A: Purification of (−)-humulone ((−)-IV) from racemic (±)-humulone (III).

Solutions of racemic (±)-humulone (III) in methanol (10%, w/v) and 1R,2R-4-cyclohexene-1,2-diamine in methanol (10%, w/v) were formulated respectively. Both solutions were mixed in equimolar amounts (approximately 3:1 by volume), methanol was evaporated, and the residue was re-dissolved in a minimal amount of 2-propanole (other solvents can be used, as for example t-butyl methyl ether, acetonitrile, ethyl acetate, or benzene). Crystals were formed, consisting of the amine salt of (−)-humulone (IV), while the (+)-humulone ((+)-IV) salt remained in solution. The crystals were filtered, dried, than mixed with hexanes and aq. sulfuric acid to liberate the free acid of (−)-humulone ((−)-IV). The hexane layer was separated, washed with brine, dried with sodium sulfate and evaporated to afford (−)-humulone ((−)-IV) as indicated by chiral HPLC.

Step 2B: Purification of (+)-humulone ((+)-IV) from racemic (±)-humulone (III)

Solutions of racemic (±)-humulone (III) in methanol (10%, w/v) and 1S,2S-4-cyclohexene-1,2-diamine in methanol (10%, w/v) are formulated respectively. Both are mixed in equimolar amounts (approximately 3:1 by volume), methanol is evaporated, and the residue is re-dissolved in a minimal amount of 2-propanole (other solvents can be used, as for example t-butyl methyl ether, acetonitrile, ethyl acetate, or benzene). Crystals will form, consisting of the amine salt of (+)-humulone ((+)-IV), while the (−)-humulone ((−)-IV) salt will remain in solution. The crystals are filtered, dried, than mixed with hexanes and aq. sulfuric acid to liberate the free acid of (+)-humulone ((+)-IV). The hexane layer is separated, washed with brine, dried with sodium sulfate and evaporated to yield (+)-humulone ((+)-IV) as indicated by chiral HPLC.

Example 14

Preparation of (+)-tetrahydro humulone and (−)-tetrahydro humulone from tetrahydro deoxyhumulone Scheme V

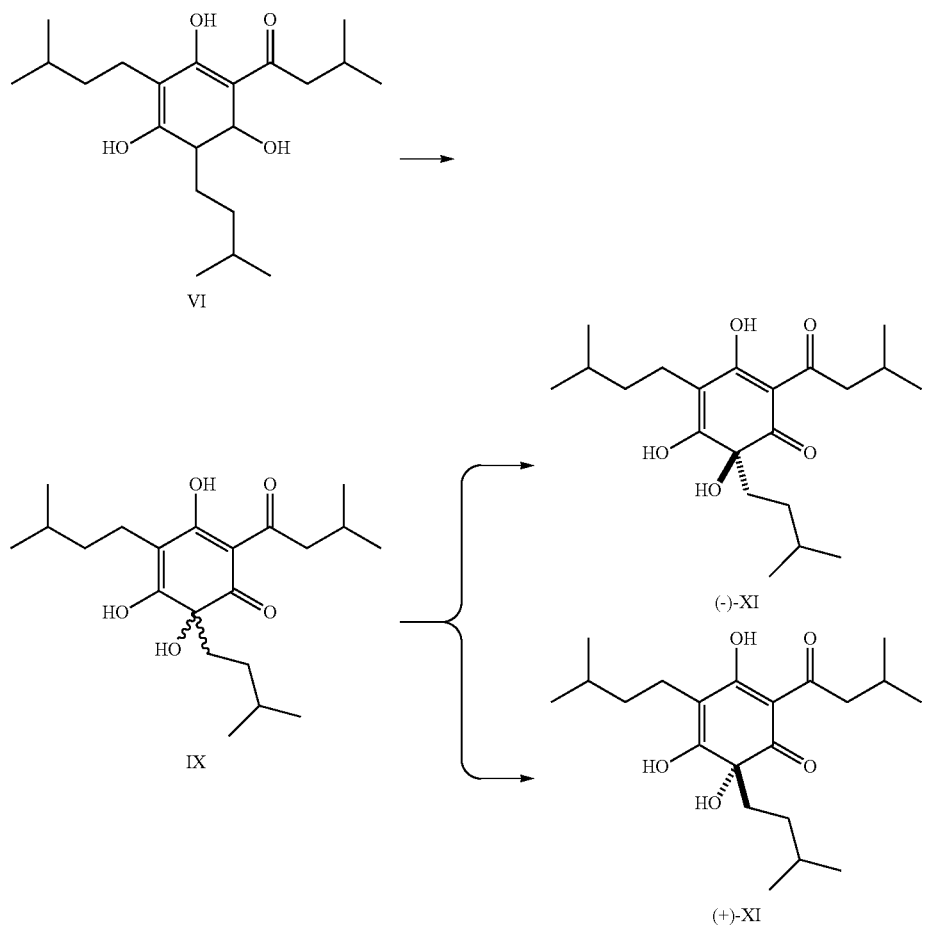

Step 1: Synthesis of racemic (±)-tetrahydro humulone (IX) from tetrahydro deoxyhumulone (VI).

A 10% (w/v) solution of tetrahydro deoxyhumulone (VI) in acetic acid is prepared, and a catalytic amount of concentrated sulfuric acid is added to the solution. The solution is stirred and 1 eq of a 30% (w/w) solution of hydrogen peroxide is added dropwise. After 2 hours the reaction is judged complete using HPLC, and water and dichloromethane are added. The racemic (±)-tetrahydro humulone (IX) is extracted into dichloromethane and concentrated in vacuo to yield the free acid form of the racemic (±)-tetrahydro humulone (IX).

Step 2A: Purification of (−)-tetrahydro humulone ((−)-XI) from racemic (±)-tetrahydro humulone (IX).

Solutions of racemic (±)-tetrahydro humulone (IX) in methanol (10%, w/v) and 1R,2R-4-cyclohexene-1,2-diamine in methanol (10%, w/v) are formulated respectively. Both solutions are mixed in equimolar amounts (approximately 3:1 by volume), methanol is evaporated, and the residue is re-dissolved in a minimal amount of 2-propanole (other solvents can be used, as for example t-butyl methyl ether, acetonitrile, ethyl acetate, or benzene). Crystals will form, consisting of the amine salt of (−)-tetrahydro humulone ((−)-XI), while the (+)-tetrahydro humulone ((+)-XI) salt will remain in solution. The crystals are filtered, dried, than mixed with hexanes and aq. sulfuric acid to liberate the free acid of (−)-tetrahydro humulone ((−)-XI). The hexane layer is separated, washed with brine, dried with sodium sulfate and evaporated to (−)-tetrahydro humulone ((−)-XI) as indicated by chiral HPLC.

Step 2B: Purification of (+)-tetrahydro humulone ((+)-XI) from racemic (±)-tetrahydro humulone Solutions of racemic (±)-tetrahydro humulone (IX) in methanol (10%, w/v) and 1S,2S-4-cyclohexene-1,2-diamine in methanol (10%, w/v) are formulated respectively. Both solutions are mixed in equimolar amounts (approximately 3:1 by volume), methanol is evaporated, and the residue is re-dissolved in a minimal amount of 2-propanole (other solvents can be used, as for example t-butyl methyl ether, acetonitrile, ethyl acetate, or benzene). Crystals will form, consisting of the amine salt of (+)-tetrahydro humulone ((+)-XI), while the (−)-tetrahydro humulone ((−)-XI) salt will remain in solution. The crystals are filtered, dried, than mixed with hexanes and aq. sulfuric acid to liberate the free acid of (+)-tetrahydro humulone ((+)-XI). The hexane layer is separated, washed with brine, dried with sodium sulfate and evaporated to (+)-tetrahydro humulone ((+)-XI) as indicated by chiral HPLC.

Example 15

Preparation of Additional KDT500 Salts

Preparation of Calcium(II) Salt ("KDT505")

Water (1000 µL) and the potassium salt of KDT500 (88.2 mg) were added to a 4 mL vial, followed by 26.6 mg of calcium chloride (1.10 eq) in 120 µL of water. The mixture was stirred for one hour and precipitate was filtered off, washed 4× with 1 mL of water, and dried under high vacuum to obtain 6.9 mg of product. The product had a melting point of 125.1° C. and a water content of 1.28 KF.

Preparation of Magnesium(II) Salt ("KDT506")

Water (1200 µL) and the potassium salt of KDT500 (50.1 mg) were added to a 4 mL vial, followed by 7.8 mg of magnesium sulfate (0.53 eq) in 200 µL of water. The mixture was stirred for one hour and precipitate was filtered off, washed 2× with 1 mL of water, and dried under high vacuum to obtain 47 mg of product. The product had a melting point of 130.0° C. and a water content of 1.27 KF.

Preparation of Zinc(II) Salt ("KDT507")

Water (1300 µL) and the potassium salt of KDT500 (84.7 mg) were added to a 4 mL vial, followed by 31.6 mg of zinc sulfate heptahydrate (0.53 eq) in 300 µL of water. The mixture was stirred for one hour and precipitate was filtered off, washed 2× with 1 mL of water, and dried under high vacuum to obtain 71.6 mg of product. The product had a melting point of 134.7° C. and a water content of 2.42 KF.

Preparation of Iron(III) Salt ("KDT508")

Water (1000 µL) and the potassium salt of KDT500 (61.9 mg) were added to a 4 mL vial, followed by 43.4 mg of iron(III) chloride hexahydrate (0.53 eq) in 300 µL of water. The mixture was stirred for one hour and precipitate was filtered off, washed 2× with 1 mL of water, and dried under high vacuum to obtain 71.6 mg of product. The product had a melting point of 72.9° C. and a water content of 1.07 KF.

Preparation of Sodium(I) Salt ("KDT509")

Water (1000 µL) and KDT500 free salt (109.5 mg) were added to a 4 mL vial, followed by 1M aq. NaOH solution (300 µL, 1.00 eq). The mixture was evaporated and dried under high vacuum. The product had a melting point of 113.9° C. and a water content of 1.15 KF.

Preparation of Copper(II) Salt ("KDT510")

Water (1000 µL) and KDT500 free salt (109.5 mg) were added to a 4 mL vial, followed by 1M aq. NaOH solution (300 4, 1.00 eq). The mixture evaporated and dried under high vacuum. The product had a melting point of 104.9° C. and a water content of 1.18 KF.

Preparation of Guanidinium Salt ("KDT511")

Water (1000 µL) and KDT500 free salt (109.5 mg) were added to a 4 mL vial, followed by 1M aq. NaOH solution (300 µL, 1.00 eq). The mixture evaporated and dried under high vacuum. The product had a melting point of 140.8° C. and a water content of 0.94 KF.

As stated above, the foregoing is merely intended to illustrate various embodiments of the present invention. The specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference as if fully set forth herein.

REFERENCES

1. Babish J Med Food 13:535 (2010)
2. Berge J Pharm Sci 66:1 (1977)
3. Boden Diabetes 46:3 (1997)
4. Dahlberg J Sep Sci 33:2828 (2010)
5. De Keukeleire Tetrahedron 26:385 (1970)
6. De Keukeleire Tetrahedron 27:4939 (1971)
7. Dong J Am Chem Soc 130:2738 (2008)

8. Fasshauer Biochem Biophys Res Commun 290:1084 (2002)
9. Gotoh Biochem Biophys Res Commun 354:591 (2007)
10. Hajjaj Appl Environ Microbiol 67:2596 (2001)
11. Hara J Pharmaceut Sci 100:3594 (2011)
12. Hirasawa Nature Med 11:90 (2005)
13. Konda Arthritis Rheum 62:1683 (2010)
14. Li Mol Endocrinol 16:1040 (2002)
15. Martin Atherosclerosis 137:S75 (1998)
16. Miyake Biosci Biotechnol Biochem 70:1154 (2006)
17. Oh Cell 142:687 (2010)
18. Pascual Nature (London) 437:759 (2005)
19. Raz Diabetes Metab Res Rev 21:3 (2005)
20. Stumvoll Ann Med 34:217 (2002)
21. Talukdar Trends Pharmacol Sci 32:543 (2011)
22. Tontonoz Cell 79:1147 (1994)
23. Tontonoz Genes Dev 8:1224 (1994)
24. Tripp Acta Hort (ISHS) 848:221 (2009)
25. Wang Plant Physiol 148:1254 (2008)

TABLE 1

Crystallographic data for the structures provided

| | |
|---|---|
| Identification code | kdtt_501_0ma |
| Empirical formula | C168 H270 K8 O43 |
| Formula weight | 3290.64 |
| Temperature | 110(2) K |
| Wavelength | 0.71073 Å |
| Crystal system | Orthorhombic |
| Space group | P 21 21 2 |
| Unit cell dimensions | a = 23.3110(9) Å   α = 90° |
| | b = 28.9052(12) Å  β = 90° |
| | c = 13.6845(5) Å   γ = 90° |
| Volume | 9220.7(6) Å$^3$ |
| Z | 2 |
| Density (calculated) | 1.185 Mg/m$^3$ |
| Absorption coefficient | 0.258 mm$^{-1}$ |
| F(000) | 3548 |
| Crystal size | 0.37 × 0.30 × 0.28 mm$^3$ |
| Theta range for data collection | 2.05 to 25.35° |
| Index ranges | −26 <= h <= 28, −34 <= k <= 34, −16 <= l <= 14 |
| Reflections collected | 68211 |
| Independent reflections | 16681 [R(int) = 0.0386] |
| Completeness to theta = 25.00° | 98.4% |
| Max. and min. transmission | 0.9312 and 0.9106 |
| Refinement method | Full-matrix least-squares on F$^2$ |
| Data/restraints/parameters | 16681/0/1019 |
| Goodness-of-fit on F$^2$ | 1.079 |
| Final R indices [I > 2sigma(I)] | R1 = 0.0694, wR2 = 0.1704 |
| R indices (all data) | R1 = 0.0795, wR2 = 0.1823 |
| Absolute structure parameter | 0.04(4) |
| Largest diff. peak and hole | 0.949 and −0.424 e · Å$^{-3}$ |

TABLE 2

Atomic coordinates (×10$^4$) and equivalent isotropic displacement parameters (Å$^2$ × 10$^3$) for crystal (+)-KDT501 (U(eq) defined as 1/3 of the trace of the orthogonalized U$^{ij}$ tensor)

| | x | y | z | U(eq) |
|---|---|---|---|---|
| C(1) | 7524(2) | 5106(1) | 9242(3) | 28(1) |
| C(2) | 8024(2) | 4959(1) | 9927(3) | 35(1) |
| C(3) | 7914(2) | 4506(1) | 10298(3) | 33(1) |
| C(4) | 7453(2) | 4302(1) | 9756(3) | 34(1) |
| C(5) | 7216(2) | 4643(1) | 8998(3) | 33(1) |
| C(6) | 7115(2) | 5428(1) | 9834(3) | 36(1) |
| C(7) | 6892(4) | 5255(2) | 10809(5) | 72(2) |
| C(8) | 6566(3) | 5590(2) | 11380(4) | 50(1) |
| C(9) | 6337(3) | 5389(3) | 12359(5) | 68(2) |
| C(10) | 5872(6) | 5053(5) | 12195(8) | 148(6) |
| C(11) | 6796(4) | 5225(3) | 13006(6) | 91(3) |
| C(12) | 8204(2) | 4288(1) | 11112(3) | 41(1) |
| C(13) | 8714(3) | 4528(2) | 11556(5) | 56(2) |
| C(14) | 8911(3) | 4318(2) | 12552(5) | 60(2) |
| C(15) | 8487(5) | 4435(3) | 13312(5) | 93(3) |
| C(16) | 9491(5) | 4512(4) | 12823(11) | 159(6) |
| C(17) | 7316(2) | 4476(2) | 7954(3) | 39(1) |
| C(18) | 6870(2) | 4671(2) | 7236(4) | 44(1) |
| C(19) | 6917(3) | 4494(2) | 6194(4) | 54(1) |
| C(20) | 6405(3) | 4629(3) | 5597(5) | 74(2) |
| C(21) | 7461(4) | 4659(3) | 5703(5) | 82(2) |
| O(1) | 7752(1) | 5356(1) | 8454(2) | 34(1) |
| O(2) | 8426(2) | 5226(1) | 10086(3) | 42(1) |
| O(3) | 7256(2) | 3907(1) | 9822(3) | 43(1) |
| O(4) | 7004(1) | 5799(1) | 9500(2) | 38(1) |
| O(5) | 8047(2) | 3916(1) | 11452(3) | 60(1) |
| C(22) | 7596(2) | 6286(1) | 5706(3) | 32(1) |
| C(23) | 7561(2) | 6826(1) | 5706(4) | 39(1) |
| C(24) | 7773(2) | 6981(2) | 6619(3) | 35(1) |
| C(25) | 8071(2) | 6608(2) | 7085(3) | 30(1) |
| C(26) | 8089(2) | 6191(2) | 6411(3) | 33(1) |
| C(27) | 7030(2) | 6134(1) | 6157(3) | 35(1) |
| C(28) | 6532(2) | 6085(1) | 5470(4) | 44(1) |
| C(29) | 5957(2) | 6096(2) | 5957(4) | 50(1) |
| C(30) | 5435(2) | 6099(2) | 5260(4) | 54(1) |
| C(31) | 4893(3) | 6202(3) | 5806(6) | 75(2) |
| C(32) | 5377(3) | 5650(3) | 4727(5) | 69(2) |
| C(33) | 8688(2) | 6152(2) | 5906(4) | 43(1) |
| C(34) | 8850(3) | 5656(2) | 5614(4) | 53(1) |
| C(35) | 8940(3) | 5313(3) | 6443(5) | 60(2) |
| C(36) | 9068(4) | 4832(3) | 5990(6) | 77(2) |
| C(37) | 9412(4) | 5462(3) | 7133(5) | 84(2) |
| C(38) | 7655(2) | 7431(2) | 7050(3) | 39(1) |
| C(39) | 7350(4) | 7795(2) | 6449(5) | 70(2) |
| C(40) | 7632(4) | 8042(3) | 5651(7) | 87(2) |
| C(41) | 7251(5) | 8330(3) | 5056(7) | 108(3) |
| C(42) | 8045(6) | 8295(5) | 6214(12) | 172(6) |
| O(6) | 7666(2) | 6098(1) | 4775(3) | 41(1) |
| O(7) | 7349(2) | 7029(1) | 5011(3) | 52(1) |
| O(8) | 8285(1) | 6599(1) | 7913(2) | 34(1) |
| O(9) | 6986(1) | 6066(1) | 7050(2) | 38(1) |
| O(10) | 7759(2) | 7512(1) | 7914(3) | 45(1) |
| C(43) | 9206(2) | 2357(2) | 11169(3) | 32(1) |
| C(44) | 9254(2) | 2831(2) | 10658(4) | 36(1) |
| C(45) | 9825(2) | 2899(2) | 10303(3) | 34(1) |
| C(46) | 10172(2) | 2515(1) | 10586(3) | 32(1) |
| C(47) | 9823(2) | 2157(2) | 11149(3) | 32(1) |
| C(48) | 8995(2) | 2406(2) | 12207(3) | 37(1) |
| C(49) | 9293(3) | 2753(2) | 12844(4) | 50(1) |
| C(50) | 9393(4) | 2593(2) | 13886(5) | 74(2) |
| C(51) | 9820(5) | 2928(3) | 14482(7) | 106(3) |
| C(52) | 9616(8) | 3368(3) | 14555(6) | 167(7) |
| C(53) | 9965(6) | 2714(4) | 15395(7) | 115(3) |
| C(54) | 10026(2) | 3288(2) | 9736(3) | 33(1) |
| C(55) | 9587(2) | 3651(2) | 9436(4) | 45(1) |
| C(56) | 9221(3) | 3489(3) | 8539(5) | 59(2) |
| C(57) | 8725(3) | 3809(3) | 8372(6) | 82(2) |
| C(58) | 9567(4) | 3424(4) | 7645(6) | 108(3) |
| C(59) | 9882(2) | 1677(2) | 10713(3) | 36(1) |
| C(60) | 9653(2) | 1295(2) | 11353(4) | 42(1) |
| C(61) | 9602(3) | 834(2) | 10846(5) | 67(2) |
| C(62) | 9336(4) | 470(2) | 11526(6) | 81(2) |
| C(63) | 10172(5) | 682(3) | 10454(8) | 125(5) |
| O(11) | 8798(1) | 2080(1) | 10663(2) | 37(1) |
| O(12) | 8825(1) | 3073(1) | 10574(3) | 53(1) |
| O(13) | 10687(1) | 2447(1) | 10439(3) | 44(1) |
| O(14) | 8606(2) | 2161(1) | 12507(2) | 45(1) |
| O(15) | 10531(1) | 3326(1) | 9471(2) | 35(1) |
| C(64) | 6773(2) | 7178(2) | 12470(4) | 47(1) |
| C(65) | 7186(2) | 6744(2) | 12389(3) | 40(1) |
| C(66) | 7458(2) | 6767(1) | 11475(3) | 31(1) |
| C(67) | 7333(2) | 7202(2) | 11015(3) | 34(1) |
| C(68) | 7027(2) | 7519(2) | 11725(4) | 44(1) |
| C(69) | 6192(3) | 6998(2) | 12142(4) | 54(1) |
| C(70) | 5847(3) | 6754(3) | 12876(6) | 72(2) |
| C(71) | 5325(4) | 6482(3) | 12490(7) | 95(3) |

TABLE 2-continued

Atomic coordinates ($\times 10^4$) and equivalent isotropic displacement parameters ($Å^2 \times 10^3$) for crystal (+)-KDT501 (U(eq) defined as 1/3 of the trace of the orthogonalized $U^{ij}$ tensor)

| | x | y | z | U(eq) |
|---|---|---|---|---|
| C(72) | 4752(4) | 6633(4) | 12595(7) | 100(3) |
| C(73) | 4721(6) | 7091(4) | 12195(9) | 135(4) |
| C(74) | 4301(5) | 6345(7) | 12259(12) | 174(7) |
| C(75) | 7464(3) | 7874(2) | 12165(4) | 49(1) |
| C(76) | 8000(3) | 7660(2) | 12596(4) | 50(1) |
| C(77) | 8409(3) | 7997(2) | 13104(5) | 54(1) |
| C(78) | 8696(3) | 8341(2) | 12393(5) | 66(2) |
| C(79) | 8864(3) | 7718(3) | 13668(7) | 89(3) |
| C(80) | 7868(2) | 6439(1) | 11068(3) | 27(1) |
| C(81) | 8128(2) | 6080(1) | 11742(3) | 34(1) |
| C(82) | 8581(2) | 6290(2) | 12429(3) | 36(1) |
| C(83) | 9073(2) | 6516(2) | 11867(4) | 50(1) |
| C(84) | 8812(2) | 5905(2) | 13095(4) | 49(1) |
| O(16) | 6741(2) | 7354(1) | 13432(3) | 56(1) |
| O(17) | 7214(2) | 6461(1) | 13049(2) | 46(1) |
| O(18) | 7471(1) | 7341(1) | 10200(2) | 35(1) |
| O(19) | 6045(2) | 7027(1) | 11291(3) | 55(1) |
| O(20) | 8024(1) | 6460(1) | 10215(2) | 31(1) |
| O(21) | 6520(2) | 3179(1) | 10191(3) | 50(1) |
| O(22) | 9560(4) | 5349(3) | 10090(10) | 96(4) |
| K(1) | 8740(1) | 5960(1) | 9107(1) | 32(1) |
| K(2) | 7682(1) | 3139(1) | 10764(1) | 32(1) |
| K(3) | 7153(1) | 6676(1) | 8756(1) | 28(1) |
| K(4) | 6484(1) | 2234(1) | 10709(1) | 33(1) |

TABLE 3

Bond lengths [Å] and angles [ ] for crystal (+)-KDT501 (symmetry transformations used to generate equivalent atoms: #1 −x + 3/2, y + 1/2, −z + 2 #2 −x + 3/2, y − 1/2, −z + 2)

| | x |
|---|---|
| C(1)—O(1) | 1.402(5) |
| C(1)—C(5) | 1.554(5) |
| C(1)—C(2) | 1.556(7) |
| C(1)—C(6) | 1.559(6) |
| C(2)—O(2) | 1.234(6) |
| C(2)—C(3) | 1.428(6) |
| C(3)—C(4) | 1.432(6) |
| C(3)—C(12) | 1.447(7) |
| C(4)—O(3) | 1.235(5) |
| C(4)—C(5) | 1.533(6) |
| C(5)—C(17) | 1.527(6) |
| C(5)—H(5) | 1.0000 |
| C(6)—O(4) | 1.195(5) |
| C(6)—C(7) | 1.517(7) |
| C(7)—C(8) | 1.457(8) |
| C(7)—H(7A) | 0.9900 |
| C(7)—H(7B) | 0.9900 |
| C(8)—C(9) | 1.555(9) |
| C(8)—H(8A) | 0.9900 |
| C(8)—H(8B) | 0.9900 |
| C(9)—C(11) | 1.469(12) |
| C(9)—C(10) | 1.474(12) |
| C(9)—H(9) | 1.0000 |
| C(10)—H(10A) | 0.9800 |
| C(10)—H(10B) | 0.9800 |
| C(10)—H(10C) | 0.9800 |
| C(11)—H(11A) | 0.9800 |
| C(11)—H(11B) | 0.9800 |
| C(11)—H(11C) | 0.9800 |
| C(12)—O(5) | 1.227(6) |
| C(12)—C(13) | 1.505(8) |
| C(13)—C(14) | 1.561(8) |
| C(13)—H(13A) | 0.9900 |
| C(13)—H(13B) | 0.9900 |
| C(14)—C(15) | 1.475(11) |
| C(14)—C(16) | 1.510(11) |
| C(14)—H(14) | 1.0000 |
| C(15)—H(15A) | 0.9800 |

TABLE 3-continued

Bond lengths [Å] and angles [ ] for crystal (+)-KDT501 (symmetry transformations used to generate equivalent atoms: #1 −x + 3/2, y + 1/2, −z + 2 #2 −x + 3/2, y − 1/2, −z + 2)

| | x |
|---|---|
| C(15)—H(15B) | 0.9800 |
| C(15)—H(15C) | 0.9800 |
| C(16)—H(16A) | 0.9800 |
| C(16)—H(16B) | 0.9800 |
| C(16)—H(16C) | 0.9800 |
| C(17)—C(18) | 1.537(7) |
| C(17)—H(17A) | 0.9900 |
| C(17)—H(17B) | 0.9900 |
| C(18)—C(19) | 1.518(7) |
| C(18)—H(18A) | 0.9900 |
| C(18)—H(18B) | 0.9900 |
| C(19)—C(20) | 1.498(9) |
| C(19)—C(21) | 1.513(10) |
| C(19)—H(19) | 1.0000 |
| C(20)—H(20A) | 0.9800 |
| C(20)—H(20B) | 0.9800 |
| C(20)—H(20C) | 0.9800 |
| C(21)—H(21A) | 0.9800 |
| C(21)—H(21B) | 0.9800 |
| C(21)—H(21C) | 0.9800 |
| O(1)—H(1) | 0.8400 |
| C(22)—O(6) | 1.395(5) |
| C(22)—C(27) | 1.522(6) |
| C(22)—C(26) | 1.527(6) |
| C(22)—C(23) | 1.562(6) |
| C(23)—O(7) | 1.223(6) |
| C(23)—C(24) | 1.417(7) |
| C(24)—C(25) | 1.434(6) |
| C(24)—C(38) | 1.454(6) |
| C(25)—O(8) | 1.237(5) |
| C(25)—C(26) | 1.517(6) |
| C(26)—C(33) | 1.561(7) |
| C(26)—H(26) | 1.0000 |
| C(27)—O(9) | 1.242(6) |
| C(27)—C(28) | 1.500(7) |
| C(28)—C(29) | 1.498(7) |
| C(28)—H(28A) | 0.9900 |
| C(28)—H(28B) | 0.9900 |
| C(29)—C(30) | 1.546(8) |
| C(29)—H(29A) | 0.9900 |
| C(29)—H(29B) | 0.9900 |
| C(30)—C(32) | 1.497(9) |
| C(30)—C(31) | 1.499(9) |
| C(30)—H(30) | 1.0000 |
| C(31)—H(31A) | 0.9800 |
| C(31)—H(31B) | 0.9800 |
| C(31)—H(31C) | 0.9800 |
| C(32)—H(32A) | 0.9800 |
| C(32)—H(32B) | 0.9800 |
| C(32)—H(32C) | 0.9800 |
| C(33)—C(34) | 1.535(7) |
| C(33)—H(33A) | 0.9900 |
| C(33)—H(33B) | 0.9900 |
| C(34)—C(35) | 1.521(8) |
| C(34)—H(34A) | 0.9900 |
| C(34)—H(34B) | 0.9900 |
| C(35)—C(37) | 1.512(10) |
| C(35)—C(36) | 1.551(9) |
| C(35)—H(35) | 1.0000 |
| C(36)—H(36A) | 0.9800 |
| C(36)—H(36B) | 0.9800 |
| C(36)—H(36C) | 0.9800 |
| C(37)—H(37A) | 0.9800 |
| C(37)—H(37B) | 0.9800 |
| C(37)—H(37C) | 0.9800 |
| C(38)—O(10) | 1.229(6) |
| C(38)—C(39) | 1.513(7) |
| C(39)—C(40) | 1.460(11) |
| C(39)—H(39A) | 0.9900 |
| C(39)—H(39B) | 0.9900 |
| C(40)—C(42) | 1.434(15) |
| C(40)—C(41) | 1.465(13) |
| C(40)—H(40) | 1.0000 |
| C(41)—H(41A) | 0.9800 |

TABLE 3-continued

Bond lengths [Å] and angles [ ] for crystal (+)-KDT501
(symmetry transformations used to generate equivalent atoms:
1 −x + 3/2, y + 1/2, −z + 2  #2 −x + 3/2, y − 1/2, −z + 2)

| | x |
|---|---|
| C(41)—H(41B) | 0.9800 |
| C(41)—H(41C) | 0.9800 |
| C(42)—H(42A) | 0.9800 |
| C(42)—H(42B) | 0.9800 |
| C(42)—H(42C) | 0.9800 |
| O(6)—H(6) | 0.8400 |
| C(43)—O(11) | 1.423(5) |
| C(43)—C(48) | 1.510(7) |
| C(43)—C(44) | 1.544(6) |
| C(43)—C(47) | 1.549(6) |
| C(44)—O(12) | 1.226(6) |
| C(44)—C(45) | 1.430(6) |
| C(45)—C(46) | 1.429(6) |
| C(45)—C(54) | 1.443(6) |
| C(46)—O(13) | 1.233(5) |
| C(46)—C(47) | 1.526(6) |
| C(47)—C(59) | 1.518(6) |
| C(47)—H(47) | 1.0000 |
| C(48)—O(14) | 1.223(6) |
| C(48)—C(49) | 1.499(7) |
| C(49)—C(50) | 1.518(9) |
| C(49)—H(49A) | 0.9900 |
| C(49)—H(49B) | 0.9900 |
| C(50)—C(51) | 1.608(12) |
| C(50)—H(50A) | 0.9900 |
| C(50)—H(50B) | 0.9900 |
| C(51)—C(52) | 1.364(15) |
| C(51)—C(53) | 1.433(13) |
| C(51)—H(51) | 1.0000 |
| C(52)—H(52A) | 0.9800 |
| C(52)—H(52B) | 0.9800 |
| C(52)—H(52C) | 0.9800 |
| C(53)—H(53A) | 0.9800 |
| C(53)—H(53B) | 0.9800 |
| C(53)—H(53C) | 0.9800 |
| C(54)—O(15) | 1.235(5) |
| C(54)—C(55) | 1.523(6) |
| C(55)—C(56) | 1.566(8) |
| C(55)—H(55A) | 0.9900 |
| C(55)—H(55B) | 0.9900 |
| C(56)—C(58) | 1.477(11) |
| C(56)—C(57) | 1.500(9) |
| C(56)—H(56) | 1.0000 |
| C(57)—H(57A) | 0.9800 |
| C(57)—H(57B) | 0.9800 |
| C(57)—H(57C) | 0.9800 |
| C(58)—H(58A) | 0.9800 |
| C(58)—H(58B) | 0.9800 |
| C(58)—H(58C) | 0.9800 |
| C(59)—C(60) | 1.507(6) |
| C(59)—H(59A) | 0.9900 |
| C(59)—H(59B) | 0.9900 |
| C(60)—C(61) | 1.505(8) |
| C(60)—H(60A) | 0.9900 |
| C(60)—H(60B) | 0.9900 |
| C(61)—C(63) | 1.498(12) |
| C(61)—C(62) | 1.535(8) |
| C(61)—H(61) | 1.0000 |
| C(62)—H(62A) | 0.9800 |
| C(62)—H(62B) | 0.9800 |
| C(62)—H(62C) | 0.9800 |
| C(63)—H(63A) | 0.9800 |
| C(63)—H(63B) | 0.9800 |
| C(63)—H(63C) | 0.9800 |
| O(11)—H(11) | 0.8400 |
| C(64)—O(16) | 1.412(6) |
| C(64)—C(69) | 1.520(9) |
| C(64)—C(68) | 1.537(8) |
| C(64)—C(65) | 1.585(7) |
| C(65)—O(17) | 1.220(6) |
| C(65)—C(66) | 1.404(7) |
| C(66)—C(67) | 1.435(6) |
| C(66)—C(80) | 1.457(6) |
| C(67)—O(18) | 1.229(6) |
| C(67)—C(68) | 1.514(7) |
| C(68)—C(75) | 1.565(8) |
| C(68)—H(68) | 1.0000 |
| C(69)—O(19) | 1.216(7) |
| C(69)—C(70) | 1.468(9) |
| C(70)—C(71) | 1.542(11) |
| C(70)—H(70A) | 0.9900 |
| C(70)—H(70B) | 0.9900 |
| C(71)—C(72) | 1.414(12) |
| C(71)—H(71A) | 0.9900 |
| C(71)—H(71B) | 0.9900 |
| C(72)—C(74) | 1.418(15) |
| C(72)—C(73) | 1.433(16) |
| C(72)—H(72) | 1.0000 |
| C(73)—H(73A) | 0.9800 |
| C(73)—H(73B) | 0.9800 |
| C(73)—H(73C) | 0.9800 |
| C(74)—H(74A) | 0.9800 |
| C(74)—H(74B) | 0.9800 |
| C(74)—H(74C) | 0.9800 |
| C(75)—C(76) | 1.515(8) |
| C(75)—H(75A) | 0.9900 |
| C(75)—H(75B) | 0.9900 |
| C(76)—C(77) | 1.531(8) |
| C(76)—H(76A) | 0.9900 |
| C(76)—H(76B) | 0.9900 |
| C(77)—C(79) | 1.540(9) |
| C(77)—C(78) | 1.543(9) |
| C(77)—H(77) | 1.0000 |
| C(78)—H(78A) | 0.9800 |
| C(78)—H(78B) | 0.9800 |
| C(78)—H(78C) | 0.9800 |
| C(79)—H(79A) | 0.9800 |
| C(79)—H(79B) | 0.9800 |
| C(79)—H(79C) | 0.9800 |
| C(80)—O(20) | 1.223(5) |
| C(80)—C(81) | 1.515(6) |
| C(81)—C(82) | 1.538(7) |
| C(81)—H(81A) | 0.9900 |
| C(81)—H(81B) | 0.9900 |
| C(82)—C(83) | 1.529(7) |
| C(82)—C(84) | 1.535(7) |
| C(82)—H(82) | 1.0000 |
| C(83)—H(83A) | 0.9800 |
| C(83)—H(83B) | 0.9800 |
| C(83)—H(83C) | 0.9800 |
| C(84)—H(84A) | 0.9800 |
| C(84)—H(84B) | 0.9800 |
| C(84)—H(84C) | 0.9800 |
| O(16)—H(16) | 0.8400 |
| O(21)—K(4) | 2.823(3) |
| O(21)—K(2) | 2.824(4) |
| O(21)—H(21D) | 0.9900 |
| O(21)—H(21E) | 0.9900 |
| O(22)—K(1) | 2.931(9) |
| O(22)—H(22A) | 0.9500 |
| O(22)—H(22B) | 0.9500 |
| K(1)—K(4)#1 | 3.7279(12) |
| K(1)—K(3) | 4.2658(13) |
| K(2)—K(4) | 3.8267(12) |
| K(2)—K(3)#2 | 4.2957(12) |
| K(3)—K(4)#1 | 3.6395(13) |
| K(3)—K(2)#1 | 4.2957(12) |
| K(4)—K(3)#2 | 3.6395(13) |
| K(4)—K(1)#2 | 3.7279(12) |
| O(1)—C(1)—C(5) | 117.0(3) |
| O(1)—C(1)—C(2) | 108.6(3) |
| C(5)—C(1)—C(2) | 103.8(3) |
| O(1)—C(1)—C(6) | 109.0(3) |
| C(5)—C(1)—C(6) | 110.1(3) |
| C(2)—C(1)—C(6) | 107.9(3) |
| O(2)—C(2)—C(3) | 130.4(5) |
| O(2)—C(2)—C(1) | 120.3(4) |

TABLE 3-continued

Bond lengths [Å] and angles [ ] for crystal (+)-KDT501
(symmetry transformations used to generate equivalent atoms:
1 −x + 3/2, y + 1/2, −z + 2  #2 −x + 3/2, y − 1/2, −z + 2)

| | x |
|---|---|
| C(3)—C(2)—C(1) | 109.3(4) |
| C(2)—C(3)—C(4) | 109.1(4) |
| C(2)—C(3)—C(12) | 126.1(4) |
| C(4)—C(3)—C(12) | 124.8(4) |
| O(3)—C(4)—C(3) | 128.3(4) |
| O(3)—C(4)—C(5) | 120.7(4) |
| C(3)—C(4)—C(5) | 110.9(4) |
| C(17)—C(5)—C(4) | 112.0(3) |
| C(17)—C(5)—C(1) | 113.8(4) |
| C(4)—C(5)—C(1) | 104.1(3) |
| C(17)—C(5)—H(5) | 108.9 |
| C(4)—C(5)—H(5) | 108.9 |
| C(1)—C(5)—H(5) | 108.9 |
| O(4)—C(6)—C(7) | 124.0(4) |
| O(4)—C(6)—C(1) | 118.0(4) |
| C(7)—C(6)—C(1) | 118.0(4) |
| C(8)—C(7)—C(6) | 115.5(5) |
| C(8)—C(7)—H(7A) | 108.4 |
| C(6)—C(7)—H(7A) | 108.4 |
| C(8)—C(7)—H(7B) | 108.4 |
| C(6)—C(7)—H(7B) | 108.4 |
| H(7A)—C(7)—H(7B) | 107.5 |
| C(7)—C(8)—C(9) | 113.2(5) |
| C(7)—C(8)—H(8A) | 108.9 |
| C(9)—C(8)—H(8A) | 108.9 |
| C(7)—C(8)—H(8B) | 108.9 |
| C(9)—C(8)—H(8B) | 108.9 |
| H(8A)—C(8)—H(8B) | 107.8 |
| C(11)—C(9)—C(10) | 114.5(9) |
| C(11)—C(9)—C(8) | 112.9(6) |
| C(10)—C(9)—C(8) | 111.6(6) |
| C(11)—C(9)—H(9) | 105.7 |
| C(10)—C(9)—H(9) | 105.7 |
| C(8)—C(9)—H(9) | 105.7 |
| O(5)—C(12)—C(3) | 122.3(5) |
| O(5)—C(12)—C(13) | 119.1(4) |
| C(3)—C(12)—C(13) | 118.7(4) |
| C(12)—C(13)—C(14) | 114.0(4) |
| C(12)—C(13)—H(13A) | 108.8 |
| C(14)—C(13)—H(13A) | 108.8 |
| C(12)—C(13)—H(13B) | 108.8 |
| C(14)—C(13)—H(13B) | 108.8 |
| H(13A)—C(13)—H(13B) | 107.7 |
| C(15)—C(14)—C(16) | 109.9(9) |
| C(15)—C(14)—C(13) | 109.2(6) |
| C(16)—C(14)—C(13) | 109.5(6) |
| C(15)—C(14)—H(14) | 109.4 |
| C(16)—C(14)—H(14) | 109.4 |
| C(13)—C(14)—H(14) | 109.4 |
| C(5)—C(17)—C(18) | 112.3(4) |
| C(5)—C(17)—H(17A) | 109.2 |
| C(18)—C(17)—H(17A) | 109.2 |
| C(5)—C(17)—H(17B) | 109.2 |
| C(18)—C(17)—H(17B) | 109.2 |
| H(17A)—C(17)—H(17B) | 107.9 |
| C(19)—C(18)—C(17) | 115.4(4) |
| C(19)—C(18)—H(18A) | 108.4 |
| C(17)—C(18)—H(18A) | 108.4 |
| C(19)—C(18)—H(18B) | 108.4 |
| C(17)—C(18)—H(18B) | 108.4 |
| H(18A)—C(18)—H(18B) | 107.5 |
| C(20)—C(19)—C(21) | 110.0(5) |
| C(20)—C(19)—C(18) | 111.6(5) |
| C(21)—C(19)—C(18) | 111.7(5) |
| C(20)—C(19)—H(19) | 107.8 |
| C(21)—C(19)—H(19) | 107.8 |
| C(18)—C(19)—H(19) | 107.8 |
| O(6)—C(22)—C(27) | 111.0(4) |
| O(6)—C(22)—C(26) | 114.8(4) |
| C(27)—C(22)—C(26) | 110.2(4) |
| O(6)—C(22)—C(23) | 113.3(4) |
| C(27)—C(22)—C(23) | 104.1(3) |
| C(26)—C(22)—C(23) | 102.6(3) |
| O(7)—C(23)—C(24) | 132.5(4) |
| O(7)—C(23)—C(22) | 120.0(4) |
| C(24)—C(23)—C(22) | 107.4(4) |
| C(23)—C(24)—C(25) | 108.8(4) |
| C(23)—C(24)—C(38) | 125.1(4) |
| C(25)—C(24)—C(38) | 125.8(4) |
| O(8)—C(25)—C(24) | 128.1(4) |
| O(8)—C(25)—C(26) | 122.0(4) |
| C(24)—C(25)—C(26) | 109.9(4) |
| C(25)—C(26)—C(22) | 102.8(3) |
| C(25)—C(26)—C(33) | 110.6(4) |
| C(22)—C(26)—C(33) | 113.9(4) |
| C(25)—C(26)—H(26) | 109.8 |
| C(22)—C(26)—H(26) | 109.8 |
| C(33)—C(26)—H(26) | 109.8 |
| O(9)—C(27)—C(28) | 122.5(4) |
| O(9)—C(27)—C(22) | 121.1(4) |
| C(28)—C(27)—C(22) | 116.4(4) |
| C(29)—C(28)—C(27) | 114.4(4) |
| C(29)—C(28)—H(28A) | 108.7 |
| C(27)—C(28)—H(28A) | 108.7 |
| C(29)—C(28)—H(28B) | 108.7 |
| C(27)—C(28)—H(28B) | 108.7 |
| H(28A)—C(28)—H(28B) | 107.6 |
| C(28)—C(29)—C(30) | 115.5(5) |
| C(28)—C(29)—H(29A) | 108.4 |
| C(30)—C(29)—H(29A) | 108.4 |
| C(28)—C(29)—H(29B) | 108.4 |
| C(30)—C(29)—H(29B) | 108.4 |
| H(29A)—C(29)—H(29B) | 107.5 |
| C(32)—C(30)—C(31) | 109.8(5) |
| C(32)—C(30)—C(29) | 111.5(5) |
| C(31)—C(30)—C(29) | 110.9(5) |
| C(32)—C(30)—H(30) | 108.2 |
| C(31)—C(30)—H(30) | 108.2 |
| C(29)—C(30)—H(30) | 108.2 |
| C(30)—C(31)—H(31A) | 109.5 |
| C(30)—C(31)—H(31B) | 109.5 |
| H(31A)—C(31)—H(31B) | 109.5 |
| C(30)—C(31)—H(31C) | 109.5 |
| H(31A)—C(31)—H(31C) | 109.5 |
| H(31B)—C(31)—H(31C) | 109.5 |
| C(30)—C(32)—H(32A) | 109.5 |
| C(30)—C(32)—H(32B) | 109.5 |
| H(32A)—C(32)—H(32B) | 109.5 |
| C(30)—C(32)—H(32C) | 109.5 |
| H(32A)—C(32)—H(32C) | 109.5 |
| H(32B)—C(32)—H(32C) | 109.5 |
| C(34)—C(33)—C(26) | 113.8(4) |
| C(34)—C(33)—H(33A) | 108.8 |
| C(26)—C(33)—H(33A) | 108.8 |
| C(34)—C(33)—H(33B) | 108.8 |
| C(26)—C(33)—H(33B) | 108.8 |
| H(33A)—C(33)—H(33B) | 107.7 |
| C(35)—C(34)—C(33) | 116.7(5) |
| C(35)—C(34)—H(34A) | 108.1 |
| C(33)—C(34)—H(34A) | 108.1 |
| C(35)—C(34)—H(34B) | 108.1 |
| C(33)—C(34)—H(34B) | 108.1 |
| H(34A)—C(34)—H(34B) | 107.3 |
| C(37)—C(35)—C(34) | 112.3(6) |
| C(37)—C(35)—C(36) | 111.4(6) |
| C(34)—C(35)—C(36) | 108.2(5) |
| C(37)—C(35)—H(35) | 108.3 |
| C(34)—C(35)—H(35) | 108.3 |
| C(36)—C(35)—H(35) | 108.3 |
| C(35)—C(36)—H(36A) | 109.5 |
| C(35)—C(36)—H(36B) | 109.5 |
| H(36A)—C(36)—H(36B) | 109.5 |
| C(35)—C(36)—H(36C) | 109.5 |
| H(36A)—C(36)—H(36C) | 109.5 |
| H(36B)—C(36)—H(36C) | 109.5 |
| C(35)—C(37)—H(37A) | 109.5 |
| C(35)—C(37)—H(37B) | 109.5 |
| H(37A)—C(37)—H(37B) | 109.5 |

TABLE 3-continued

Bond lengths [Å] and angles [ ] for crystal (+)-KDT501
(symmetry transformations used to generate equivalent atoms:
1 −x + 3/2, y + 1/2, −z + 2  #2 −x + 3/2, y − 1/2, −z + 2)

| | x |
|---|---|
| C(35)—C(37)—H(37C) | 109.5 |
| H(37A)—C(37)—H(37C) | 109.5 |
| H(37B)—C(37)—H(37C) | 109.5 |
| O(10)—C(38)—C(24) | 121.5(4) |
| O(10)—C(38)—C(39) | 118.9(4) |
| C(24)—C(38)—C(39) | 119.4(4) |
| C(40)—C(39)—C(38) | 122.4(7) |
| C(40)—C(39)—H(39A) | 106.7 |
| C(38)—C(39)—H(39A) | 106.7 |
| C(40)—C(39)—H(39B) | 106.7 |
| C(38)—C(39)—H(39B) | 106.7 |
| H(39A)—C(39)—H(39B) | 106.6 |
| C(42)—C(40)—C(39) | 98.6(10) |
| C(42)—C(40)—C(41) | 114.6(9) |
| C(39)—C(40)—C(41) | 114.9(7) |
| C(42)—C(40)—H(40) | 109.4 |
| C(39)—C(40)—H(40) | 109.4 |
| C(41)—C(40)—H(40) | 109.4 |
| C(40)—C(41)—H(41A) | 109.5 |
| C(40)—C(41)—H(41B) | 109.5 |
| H(41A)—C(41)—H(41B) | 109.5 |
| C(40)—C(41)—H(41C) | 109.5 |
| H(41A)—C(41)—H(41C) | 109.5 |
| H(41B)—C(41)—H(41C) | 109.5 |
| C(40)—C(42)—H(42A) | 109.5 |
| C(40)—C(42)—H(42B) | 109.5 |
| H(42A)—C(42)—H(42B) | 109.5 |
| C(40)—C(42)—H(42C) | 109.5 |
| H(42A)—C(42)—H(42C) | 109.5 |
| H(42B)—C(42)—H(42C) | 109.5 |
| C(22)—O(6)—H(6) | 109.5 |
| O(11)—C(43)—C(48) | 107.1(4) |
| O(11)—C(43)—C(44) | 109.1(3) |
| C(48)—C(43)—C(44) | 111.5(4) |
| O(11)—C(43)—C(47) | 113.7(4) |
| C(48)—C(43)—C(47) | 110.7(4) |
| C(44)—C(43)—C(47) | 104.8(3) |
| O(12)—C(44)—C(45) | 130.5(4) |
| O(12)—C(44)—C(43) | 119.3(4) |
| C(45)—C(44)—C(43) | 110.1(4) |
| C(46)—C(45)—C(44) | 109.2(4) |
| C(46)—C(45)—C(54) | 124.5(4) |
| C(44)—C(45)—C(54) | 126.3(4) |
| O(13)—C(46)—C(45) | 129.2(4) |
| O(13)—C(46)—C(47) | 119.6(4) |
| C(45)—C(46)—C(47) | 111.2(4) |
| C(59)—C(47)—C(46) | 111.9(4) |
| C(59)—C(47)—C(43) | 115.7(4) |
| C(46)—C(47)—C(43) | 104.6(3) |
| C(59)—C(47)—H(47) | 108.1 |
| C(46)—C(47)—H(47) | 108.1 |
| C(43)—C(47)—H(47) | 108.1 |
| O(14)—C(48)—C(49) | 122.5(5) |
| O(14)—C(48)—C(43) | 120.1(4) |
| C(49)—C(48)—C(43) | 117.4(4) |
| C(48)—C(49)—C(50) | 114.5(5) |
| C(48)—C(49)—H(49A) | 108.6 |
| C(50)—C(49)—H(49A) | 108.6 |
| C(48)—C(49)—H(49B) | 108.6 |
| C(50)—C(49)—H(49B) | 108.6 |
| H(49A)—C(49)—H(49B) | 107.6 |
| C(49)—C(50)—C(51) | 112.9(6) |
| C(49)—C(50)—H(50A) | 109.0 |
| C(51)—C(50)—H(50A) | 109.0 |
| C(49)—C(50)—H(50B) | 109.0 |
| C(51)—C(50)—H(50B) | 109.0 |
| H(50A)—C(50)—H(50B) | 107.8 |
| C(52)—C(51)—C(53) | 114.9(9) |
| C(52)—C(51)—C(50) | 112.5(10) |
| C(53)—C(51)—C(50) | 109.3(8) |
| C(52)—C(51)—H(51) | 106.5 |
| C(53)—C(51)—H(51) | 106.5 |
| C(50)—C(51)—H(51) | 106.5 |
| O(15)—C(54)—C(45) | 122.5(4) |
| O(15)—C(54)—C(55) | 120.0(4) |
| C(45)—C(54)—C(55) | 117.5(4) |
| C(54)—C(55)—C(56) | 111.8(4) |
| C(54)—C(55)—H(55A) | 109.3 |
| C(56)—C(55)—H(55A) | 109.3 |
| C(54)—C(55)—H(55B) | 109.3 |
| C(56)—C(55)—H(55B) | 109.3 |
| H(55A)—C(55)—H(55B) | 107.9 |
| C(58)—C(56)—C(57) | 111.8(6) |
| C(58)—C(56)—C(55) | 112.9(6) |
| C(57)—C(56)—C(55) | 110.8(6) |
| C(58)—C(56)—H(56) | 107.0 |
| C(57)—C(56)—H(56) | 107.0 |
| C(55)—C(56)—H(56) | 107.0 |
| C(60)—C(59)—C(47) | 114.1(4) |
| C(60)—C(59)—H(59A) | 108.7 |
| C(47)—C(59)—H(59A) | 108.7 |
| C(60)—C(59)—H(59B) | 108.7 |
| C(47)—C(59)—H(59B) | 108.7 |
| H(59A)—C(59)—H(59B) | 107.6 |
| C(61)—C(60)—C(59) | 114.1(4) |
| C(61)—C(60)—H(60A) | 108.7 |
| C(59)—C(60)—H(60A) | 108.7 |
| C(61)—C(60)—H(60B) | 108.7 |
| C(59)—C(60)—H(60B) | 108.7 |
| H(60A)—C(60)—H(60B) | 107.6 |
| C(63)—C(61)—C(60) | 110.9(6) |
| C(63)—C(61)—C(62) | 111.9(6) |
| C(60)—C(61)—C(62) | 111.0(5) |
| C(63)—C(61)—H(61) | 107.6 |
| C(60)—C(61)—H(61) | 107.6 |
| C(62)—C(61)—H(61) | 107.6 |
| O(16)—C(64)—C(69) | 110.5(5) |
| O(16)—C(64)—C(68) | 114.1(5) |
| C(69)—C(64)—C(68) | 111.4(4) |
| O(16)—C(64)—C(65) | 112.5(4) |
| C(69)—C(64)—C(65) | 104.6(4) |
| C(68)—C(64)—C(65) | 103.1(4) |
| O(17)—C(65)—C(66) | 131.9(4) |
| O(17)—C(65)—C(64) | 120.7(4) |
| C(66)—C(65)—C(64) | 107.3(4) |
| C(65)—C(66)—C(67) | 110.0(4) |
| C(65)—C(66)—C(80) | 127.2(4) |
| C(67)—C(66)—C(80) | 122.4(4) |
| O(18)—C(67)—C(66) | 129.2(4) |
| O(18)—C(67)—C(68) | 120.5(4) |
| C(66)—C(67)—C(68) | 110.1(4) |
| C(67)—C(68)—C(64) | 102.7(4) |
| C(67)—C(68)—C(75) | 109.8(4) |
| C(64)—C(68)—C(75) | 114.5(4) |
| C(67)—C(68)—H(68) | 109.9 |
| C(64)—C(68)—H(68) | 109.9 |
| C(75)—C(68)—H(68) | 109.9 |
| O(19)—C(69)—C(70) | 122.3(6) |
| O(19)—C(69)—C(64) | 120.7(5) |
| C(70)—C(69)—C(64) | 116.8(5) |
| C(69)—C(70)—C(71) | 116.3(6) |
| C(69)—C(70)—H(70A) | 108.2 |
| C(71)—C(70)—H(70A) | 108.2 |
| C(69)—C(70)—H(70B) | 108.2 |
| C(71)—C(70)—H(70B) | 108.2 |
| H(70A)—C(70)—H(70B) | 107.4 |
| C(72)—C(71)—C(70) | 123.6(9) |
| C(72)—C(71)—H(71A) | 106.4 |
| C(70)—C(71)—H(71A) | 106.4 |
| C(72)—C(71)—H(71B) | 106.4 |
| C(70)—C(71)—H(71B) | 106.4 |
| H(71A)—C(71)—H(71B) | 106.5 |
| C(71)—C(72)—C(74) | 119.0(11) |
| C(71)—C(72)—C(73) | 107.1(10) |
| C(74)—C(72)—C(73) | 112.5(12) |
| C(71)—C(72)—H(72) | 105.8 |
| C(74)—C(72)—H(72) | 105.8 |
| C(73)—C(72)—H(72) | 105.8 |

TABLE 3-continued

Bond lengths [Å] and angles [ ] for crystal (+)-KDT501
(symmetry transformations used to generate equivalent atoms:
1 −x + 3/2, y + 1/2, −z + 2 #2 −x + 3/2, y − 1/2, −z + 2)

| | x |
|---|---|
| C(76)—C(75)—C(68) | 114.8(4) |
| C(76)—C(75)—H(75A) | 108.6 |
| C(68)—C(75)—H(75A) | 108.6 |
| C(76)—C(75)—H(75B) | 108.6 |
| C(68)—C(75)—H(75B) | 108.6 |
| H(75A)—C(75)—H(75B) | 107.6 |
| C(75)—C(76)—C(77) | 115.5(4) |
| C(75)—C(76)—H(76A) | 108.4 |
| C(77)—C(76)—H(76A) | 108.4 |
| C(75)—C(76)—H(76B) | 108.4 |
| C(77)—C(76)—H(76B) | 108.4 |
| H(76A)—C(76)—H(76B) | 107.5 |
| C(76)—C(77)—C(79) | 108.8(5) |
| C(76)—C(77)—C(78) | 113.2(5) |
| C(79)—C(77)—C(78) | 110.8(6) |
| C(76)—C(77)—H(77) | 108.0 |
| C(79)—C(77)—H(77) | 108.0 |
| C(78)—C(77)—H(77) | 108.0 |
| O(20)—C(80)—C(66) | 121.8(4) |
| O(20)—C(80)—C(81) | 119.7(4) |
| C(66)—C(80)—C(81) | 118.4(4) |
| C(80)—C(81)—C(82) | 112.1(3) |
| C(80)—C(81)—H(81A) | 109.2 |
| C(82)—C(81)—H(81A) | 109.2 |
| C(80)—C(81)—H(81B) | 109.2 |
| C(82)—C(81)—H(81B) | 109.2 |
| H(81A)—C(81)—H(81B) | 107.9 |
| C(83)—C(82)—C(84) | 110.2(4) |
| C(83)—C(82)—C(81) | 112.1(4) |
| C(84)—C(82)—C(81) | 108.5(4) |
| C(83)—C(82)—H(82) | 108.6 |
| C(84)—C(82)—H(82) | 108.6 |
| C(81)—C(82)—H(82) | 108.6 |
| K(4)—O(21)—K(2) | 85.33(10) |
| K(4)—O(21)—H(21D) | 114.4 |
| K(2)—O(21)—H(21D) | 114.4 |
| K(4)—O(21)—H(21E) | 114.4 |
| K(2)—O(21)—H(21E) | 114.4 |
| H(21D)—O(21)—H(21E) | 111.6 |
| K(1)—O(22)—H(22A) | 120.0 |
| K(1)—O(22)—H(22B) | 120.0 |
| H(22A)—O(22)—H(22B) | 120.0 |
| O(22)—K(1)—K(4)#1 | 131.0(3) |
| O(22)—K(1)—K(3) | 155.5(2) |
| K(4)#1—K(1)—K(3) | 53.66(2) |
| O(21)—K(2)—K(4) | 47.32(7) |
| O(21)—K(2)—K(3)#2 | 99.75(7) |
| K(4)—K(2)—K(3)#2 | 52.86(2) |
| K(4)#1—K(3)—K(1) | 55.59(2) |
| K(4)#1—K(3)—K(2)#1 | 56.94(2) |
| K(1)—K(3)—K(2)#1 | 112.48(3) |
| O(21)—K(4)—K(3)#2 | 116.98(8) |
| O(21)—K(4)—K(1)#2 | 167.66(9) |
| K(3)#2—K(4)—K(1)#2 | 70.75(2) |
| O(21)—K(4)—K(2) | 47.35(7) |
| K(3)#2—K(4)—K(2) | 70.20(2) |
| K(1)#2—K(4)—K(2) | 140.84(3) |

TABLE 4

Anisotropic displacement parameters
($Å^2 \times 10^3$) for crystal (+)-KDT501

| | $U^{11}$ | $U^{22}$ | $U^{33}$ | $U^{23}$ | $U^{13}$ | $U^{12}$ |
|---|---|---|---|---|---|---|
| C(1) | 43(2) | 16(2) | 26(2) | 0(2) | 4(2) | −1(2) |
| C(2) | 61(3) | 19(2) | 25(2) | −3(2) | 8(2) | 0(2) |
| C(3) | 48(3) | 19(2) | 34(2) | −5(2) | 4(2) | −8(2) |
| C(4) | 48(3) | 23(2) | 32(2) | 0(2) | 0(2) | −4(2) |
| C(5) | 44(2) | 21(2) | 35(2) | 1(2) | 4(2) | −2(2) |
| C(6) | 47(3) | 21(2) | 39(2) | 0(2) | 10(2) | −1(2) |

TABLE 4-continued

Anisotropic displacement parameters
($Å^2 \times 10^3$) for crystal (+)-KDT501

| | $U^{11}$ | $U^{22}$ | $U^{33}$ | $U^{23}$ | $U^{13}$ | $U^{12}$ |
|---|---|---|---|---|---|---|
| C(7) | 112(5) | 39(3) | 66(4) | 2(3) | 54(4) | 3(3) |
| C(8) | 54(3) | 50(3) | 47(3) | −4(2) | 6(3) | 7(2) |
| C(9) | 75(4) | 81(4) | 48(3) | −12(3) | 21(3) | −9(4) |
| C(10) | 156(11) | 207(13) | 82(6) | −26(8) | 52(7) | −101(10) |
| C(11) | 138(8) | 81(5) | 54(3) | 20(3) | 29(5) | 17(5) |
| C(12) | 73(3) | 21(2) | 29(2) | −5(2) | 2(2) | −1(2) |
| C(13) | 63(3) | 44(3) | 61(4) | 19(3) | −18(3) | −7(3) |
| C(14) | 73(4) | 33(3) | 72(4) | 20(3) | −29(3) | −6(3) |
| C(15) | 141(8) | 92(6) | 47(4) | 9(4) | −13(5) | −23(5) |
| C(16) | 132(9) | 131(9) | 213(13) | 93(9) | −127(10) | −43(7) |
| C(17) | 63(3) | 23(2) | 33(2) | −4(2) | 3(2) | 1(2) |
| C(18) | 55(3) | 30(2) | 46(3) | 0(2) | −1(2) | 1(2) |
| C(19) | 89(4) | 35(2) | 38(3) | −2(2) | −1(3) | −1(3) |
| C(20) | 92(5) | 78(4) | 52(4) | 11(3) | −25(4) | −27(4) |
| C(21) | 97(5) | 104(6) | 43(3) | −6(4) | 11(4) | 11(4) |
| O(1) | 41(2) | 28(2) | 32(2) | 6(2) | 11(2) | 3(1) |
| O(2) | 57(2) | 22(2) | 47(2) | 1(2) | −9(2) | −10(1) |
| O(3) | 59(2) | 23(2) | 48(2) | 7(2) | −9(2) | −10(1) |
| O(4) | 44(2) | 26(2) | 44(2) | −1(1) | 5(2) | 1(1) |
| O(5) | 115(5) | 23(2) | 42(2) | 6(1) | −30(2) | −19(2) |
| C(22) | 40(2) | 28(2) | 28(2) | −2(2) | −1(2) | 1(2) |
| C(23) | 53(3) | 29(2) | 34(2) | 7(2) | −6(2) | 6(2) |
| C(24) | 44(3) | 27(2) | 33(2) | 7(2) | −2(2) | −1(2) |
| C(25) | 35(2) | 30(2) | 25(2) | −2(2) | −1(2) | −3(2) |
| C(26) | 39(2) | 30(2) | 28(2) | 2(2) | 0(2) | 1(2) |
| C(27) | 40(2) | 27(2) | 36(3) | −9(2) | 1(2) | 4(2) |
| C(28) | 39(3) | 49(3) | 44(3) | −2(2) | −3(2) | 0(2) |
| C(29) | 46(3) | 64(3) | 41(3) | −9(2) | −2(2) | −6(2) |
| C(30) | 50(3) | 65(4) | 47(3) | −4(3) | −6(3) | −3(3) |
| C(31) | 54(4) | 83(5) | 89(5) | −15(4) | −7(4) | 4(3) |
| C(32) | 49(3) | 85(5) | 73(4) | −18(4) | −5(3) | 0(3) |
| C(33) | 47(3) | 46(3) | 36(3) | −3(2) | 6(2) | 0(2) |
| C(34) | 53(3) | 63(3) | 41(3) | −3(2) | 2(3) | 12(3) |
| C(35) | 64(4) | 67(4) | 49(3) | 7(3) | 2(3) | 20(3) |
| C(36) | 98(5) | 54(4) | 80(5) | −3(3) | 9(4) | 23(3) |
| C(37) | 100(6) | 99(6) | 53(4) | −24(4) | −11(4) | 48(5) |
| C(38) | 55(3) | 31(2) | 32(2) | 1(2) | −9(2) | −3(2) |
| C(39) | 126(6) | 28(2) | 56(3) | 3(2) | −11(4) | 18(3) |
| C(40) | 81(5) | 86(5) | 94(6) | −8(5) | 13(5) | 0(4) |
| C(41) | 155(9) | 87(6) | 81(5) | 28(5) | 17(6) | 18(6) |
| C(42) | 154(12) | 154(12) | 209(16) | −2(12) | −93(12) | 22(10) |
| O(6) | 63(2) | 36(2) | 23(2) | 3(1) | −4(2) | 6(2) |
| O(7) | 88(3) | 32(2) | 36(2) | 8(1) | −19(2) | 3(2) |
| O(8) | 44(2) | 29(2) | 29(2) | −3(1) | −7(1) | 2(1) |
| O(9) | 42(2) | 39(2) | 32(2) | −3(1) | 3(1) | −2(1) |
| O(10) | 62(2) | 26(2) | 48(2) | −6(2) | −6(2) | 6(2) |
| C(43) | 31(2) | 38(2) | 26(2) | 6(2) | −6(2) | −5(2) |
| C(44) | 29(2) | 37(2) | 42(3) | 11(2) | 2(2) | −3(2) |
| C(45) | 34(2) | 35(2) | 33(2) | 3(2) | −10(2) | 1(2) |
| C(46) | 30(2) | 30(2) | 35(2) | 1(2) | 2(2) | −6(2) |
| C(47) | 34(2) | 33(2) | 28(2) | 8(2) | 0(2) | −1(2) |
| C(48) | 36(2) | 40(2) | 33(2) | 8(2) | −2(2) | −4(2) |
| C(49) | 51(3) | 47(3) | 51(3) | 2(2) | −8(3) | −3(2) |
| C(50) | 115(6) | 50(3) | 58(4) | 3(3) | −21(4) | −19(4) |
| C(51) | 149(9) | 97(7) | 73(6) | 7(5) | −23(6) | 9(6) |
| C(52) | 370(20) | 71(6) | 61(5) | 5(4) | −69(9) | −63(9) |
| C(53) | 161(10) | 106(7) | 79(6) | −28(5) | −28(6) | 3(7) |
| C(54) | 35(2) | 31(2) | 33(2) | −2(2) | 1(2) | −3(2) |
| C(55) | 41(3) | 30(2) | 63(3) | 16(2) | 0(2) | 1(2) |
| C(56) | 61(4) | 56(3) | 59(4) | 10(3) | −13(3) | 1(3) |
| C(57) | 77(5) | 83(5) | 86(5) | 16(4) | −22(4) | 5(4) |
| C(58) | 101(6) | 155(9) | 69(5) | −16(6) | −24(5) | 42(6) |
| C(59) | 39(2) | 32(2) | 37(2) | 6(2) | 2(2) | −2(2) |
| C(60) | 46(3) | 34(2) | 44(3) | 10(2) | 4(2) | −4(2) |
| C(61) | 99(5) | 39(3) | 62(4) | −3(3) | 18(4) | −22(3) |
| C(62) | 109(6) | 38(3) | 96(5) | −1(3) | 45(5) | −24(3) |
| C(63) | 180(10) | 31(3) | 164(10) | 2(4) | 107(8) | −3(4) |
| O(11) | 37(2) | 49(2) | 26(2) | 3(1) | −5(1) | −6(1) |
| O(12) | 31(2) | 56(2) | 73(3) | 28(2) | 7(2) | 8(2) |
| O(13) | 32(2) | 34(2) | 64(2) | 18(2) | 7(2) | 2(1) |
| O(14) | 49(2) | 58(2) | 29(2) | −2(2) | 3(2) | −13(2) |
| O(15) | 35(2) | 28(1) | 42(2) | 5(1) | 4(1) | −2(1) |
| C(64) | 59(3) | 50(3) | 32(3) | −4(2) | −5(2) | 22(2) |
| C(65) | 48(3) | 47(3) | 24(2) | −2(2) | −11(2) | 12(2) |
| C(66) | 40(2) | 25(2) | 27(2) | −7(2) | −12(2) | 4(2) |

TABLE 4-continued

Anisotropic displacement parameters ($Å^2 \times 10^3$) for crystal (+)-KDT501

| | $U^{11}$ | $U^{22}$ | $U^{33}$ | $U^{23}$ | $U^{13}$ | $U^{12}$ |
|---|---|---|---|---|---|---|
| C(67) | 41(2) | 30(2) | 31(2) | −8(2) | −12(2) | 4(2) |
| C(68) | 50(3) | 44(3) | 38(3) | 0(2) | −8(2) | 18(2) |
| C(69) | 54(3) | 70(4) | 39(3) | 10(3) | −4(3) | 24(3) |
| C(70) | 62(4) | 82(5) | 72(4) | 14(4) | −3(3) | 1(3) |
| C(71) | 76(5) | 112(7) | 99(6) | 48(5) | 1(5) | −17(5) |
| C(72) | 61(5) | 155(10) | 85(6) | 7(6) | −2(4) | 7(5) |
| C(73) | 176(12) | 131(10) | 97(8) | −41(7) | −3(8) | −35(9) |
| C(74) | 80(7) | 254(19) | 188(15) | −85(14) | 9(8) | −36(9) |
| C(75) | 70(4) | 33(2) | 44(3) | 1(2) | −7(3) | 6(2) |
| C(76) | 62(3) | 38(3) | 49(3) | −6(2) | −8(3) | 5(2) |
| C(77) | 50(3) | 48(3) | 65(4) | −12(3) | −6(3) | 3(2) |
| C(78) | 57(4) | 69(4) | 72(4) | −13(3) | −5(3) | 3(3) |
| C(79) | 78(5) | 70(4) | 117(7) | −15(4) | −46(5) | 11(4) |
| C(80) | 34(2) | 19(2) | 29(2) | −6(2) | −11(2) | −2(2) |
| C(81) | 43(2) | 25(2) | 33(2) | 0(2) | 2(2) | 3(2) |
| C(82) | 47(3) | 33(2) | 27(2) | 1(2) | −5(2) | 7(2) |
| C(83) | 43(3) | 59(3) | 48(3) | 11(2) | −6(2) | −8(2) |
| C(84) | 54(3) | 55(3) | 38(3) | 9(2) | 6(2) | 12(3) |
| O(16) | 76(3) | 55(2) | 37(2) | −1(2) | −3(2) | 23(2) |
| O(17) | 59(2) | 53(2) | 27(2) | 2(1) | −1(2) | 17(2) |
| O(18) | 46(2) | 24(1) | 36(2) | −3(1) | −5(1) | 3(1) |
| O(19) | 58(2) | 66(2) | 42(2) | −1(2) | 2(2) | −12(2) |
| O(20) | 41(2) | 24(1) | 29(2) | −4(1) | 0(1) | 3(1) |
| O(21) | 45(2) | 31(2) | 74(2) | 16(2) | −11(2) | −2(1) |
| O(22) | 52(5) | 56(5) | 181(12) | 49(7) | 0(6) | 7(4) |
| K(1) | 38(1) | 21(1) | 36(1) | 1(1) | 0(1) | −2(1) |
| K(2) | 37(1) | 18(1) | 42(1) | −1(1) | −7(1) | −1(1) |
| K(3) | 34(1) | 21(1) | 29(1) | −2(1) | −3(1) | 4(1) |
| K(4) | 35(1) | 24(1) | 39(1) | 2(1) | −9(1) | 0(1) |

What is claimed is:

1. A potassium salt of (+)-(4S,5R)-3,4-dihydroxy-2-(3-methylbutanoyl)-5-(3-methylbutyl)-4-(4-methylpentanoyl)cyclopent-2-en-1-one having the structure:

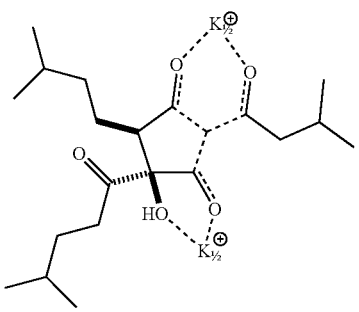

2. A crystal of the potassium salt of claim 1, wherein the crystal has a monoclinic space group P 21 21 2, and unit cell dimensions of a=23.3110(9) Å, α=90°, b=28.9052(12) Å, β=90°, c=13.6845(5) Å, and γ=90°.

3. The crystal of claim 2, wherein the crystal has the three-dimensional atomic coordinates set forth in the following table:

| | x | y | z | U(eq) |
|---|---|---|---|---|
| C(1) | 7524(2) | 5106(1) | 9242(3) | 28(1) |
| C(2) | 8024(2) | 4959(1) | 9927(3) | 35(1) |
| C(3) | 7914(2) | 4506(1) | 10298(3) | 33(1) |
| C(4) | 7453(2) | 4302(1) | 9756(3) | 34(1) |
| C(5) | 7216(2) | 4643(1) | 8998(3) | 33(1) |
| C(6) | 7115(2) | 5428(1) | 9834(3) | 36(1) |
| C(7) | 6892(4) | 5255(2) | 10809(5) | 72(2) |
| C(8) | 6566(3) | 5590(2) | 11380(4) | 50(1) |
| C(9) | 6337(3) | 5389(3) | 12359(5) | 68(2) |
| C(10) | 5872(6) | 5053(5) | 12195(8) | 148(6) |
| C(11) | 6796(4) | 5225(3) | 13006(6) | 91(3) |
| C(12) | 8204(2) | 4288(1) | 11112(3) | 41(1) |
| C(13) | 8714(3) | 4528(1) | 11556(5) | 56(2) |
| C(14) | 8911(3) | 4318(2) | 12552(5) | 60(2) |
| C(15) | 8487(5) | 4435(3) | 13312(5) | 93(3) |
| C(16) | 9491(5) | 4512(4) | 12823(11) | 159(6) |
| C(17) | 7316(2) | 4476(2) | 7954(3) | 39(1) |
| C(18) | 6870(2) | 4671(2) | 7236(4) | 44(1) |
| C(19) | 6917(3) | 4494(2) | 6194(4) | 54(1) |
| C(20) | 6405(3) | 4629(3) | 5597(5) | 74(2) |
| C(21) | 7461(4) | 4659(3) | 5703(5) | 82(2) |
| O(1) | 7752(1) | 5356(1) | 8454(2) | 34(1) |
| O(2) | 8426(2) | 5226(1) | 10086(3) | 42(1) |
| O(3) | 7256(2) | 3907(1) | 9822(3) | 43(1) |
| O(4) | 7004(1) | 5799(1) | 9500(2) | 38(1) |
| O(5) | 8047(2) | 3916(1) | 11452(3) | 60(1) |
| C(22) | 7596(2) | 6286(1) | 5706(3) | 32(1) |
| C(23) | 7561(2) | 6826(2) | 5706(4) | 39(1) |
| C(24) | 7773(2) | 6981(2) | 6619(3) | 35(1) |
| C(25) | 8071(2) | 6608(2) | 7085(3) | 30(1) |
| C(26) | 8089(2) | 6191(2) | 6411(3) | 33(1) |
| C(27) | 7030(2) | 6134(1) | 6157(3) | 35(1) |
| C(28) | 6532(2) | 6085(2) | 5470(4) | 44(1) |
| C(29) | 5957(2) | 6096(2) | 5957(4) | 50(1) |
| C(30) | 5435(2) | 6099(2) | 5260(4) | 54(1) |
| C(31) | 4893(3) | 6202(3) | 5806(6) | 75(2) |
| C(32) | 5377(3) | 5650(3) | 4727(5) | 69(2) |
| C(33) | 8688(2) | 6152(2) | 5906(4) | 43(1) |
| C(34) | 8850(3) | 5656(2) | 5614(4) | 53(1) |
| C(35) | 8940(3) | 5313(2) | 6443(5) | 60(2) |
| C(36) | 9068(4) | 4832(2) | 5990(6) | 77(2) |
| C(37) | 9412(4) | 5462(3) | 7133(5) | 84(2) |
| C(38) | 7655(2) | 7431(2) | 7050(3) | 39(1) |
| C(39) | 7350(4) | 7795(2) | 6449(5) | 70(2) |
| C(40) | 7632(4) | 8042(3) | 5651(7) | 87(2) |
| C(41) | 7251(5) | 8330(3) | 5056(7) | 108(3) |
| C(42) | 8045(6) | 8295(5) | 6214(12) | 172(6) |
| O(6) | 7666(2) | 6098(1) | 4775(2) | 41(1) |
| O(7) | 7349(2) | 7029(1) | 5011(3) | 52(1) |
| O(8) | 8285(1) | 6599(1) | 7913(2) | 34(1) |
| O(9) | 6986(1) | 6066(1) | 7050(2) | 38(1) |
| O(10) | 7759(2) | 7512(1) | 7914(3) | 45(1) |
| C(43) | 9206(2) | 2357(2) | 11169(3) | 32(1) |
| C(44) | 9254(2) | 2831(2) | 10658(4) | 36(1) |
| C(45) | 9825(2) | 2899(2) | 10303(3) | 34(1) |
| C(46) | 10172(2) | 2515(1) | 10586(3) | 32(1) |
| C(47) | 9823(2) | 2157(1) | 11149(3) | 32(1) |
| C(48) | 8995(2) | 2406(2) | 12207(3) | 37(1) |
| C(49) | 9293(3) | 2753(2) | 12844(4) | 50(1) |
| C(50) | 9393(4) | 2593(2) | 13886(5) | 74(2) |
| C(51) | 9820(5) | 2928(3) | 14482(7) | 106(3) |
| C(52) | 9616(8) | 3368(3) | 14555(6) | 167(7) |
| C(53) | 9965(6) | 2714(4) | 15395(7) | 115(3) |
| C(54) | 10026(2) | 3288(2) | 9736(3) | 33(1) |
| C(55) | 9587(2) | 3651(2) | 9436(4) | 45(1) |
| C(56) | 9221(3) | 3489(2) | 8539(5) | 59(2) |
| C(57) | 8725(3) | 3809(3) | 8372(6) | 82(2) |
| C(58) | 9567(4) | 3424(4) | 7645(6) | 108(3) |
| C(59) | 9882(2) | 1677(2) | 10713(5) | 36(1) |
| C(60) | 9653(2) | 1295(2) | 11353(4) | 42(1) |
| C(61) | 9602(3) | 834(2) | 10846(5) | 67(2) |
| C(62) | 9336(4) | 470(2) | 11526(6) | 81(2) |
| C(63) | 10172(5) | 682(2) | 10454(8) | 125(5) |
| O(11) | 8798(1) | 2080(1) | 10663(2) | 37(1) |
| O(12) | 8825(1) | 3073(1) | 10574(3) | 53(1) |
| O(13) | 10687(1) | 2447(1) | 10439(3) | 44(1) |
| O(14) | 8606(2) | 2161(1) | 12507(2) | 45(1) |
| O(15) | 10531(1) | 3326(1) | 9471(2) | 35(1) |
| C(64) | 6773(2) | 7178(2) | 12470(4) | 47(1) |
| C(65) | 7186(2) | 6744(2) | 12389(5) | 40(1) |
| C(66) | 7458(2) | 6767(1) | 11475(3) | 31(1) |
| C(67) | 7333(2) | 7202(2) | 11015(3) | 34(1) |
| C(68) | 7027(2) | 7519(2) | 11725(4) | 44(1) |
| C(69) | 6192(3) | 6998(2) | 12142(4) | 54(1) |

-continued

| | x | y | z | U(eq) |
|---|---|---|---|---|
| C(70) | 5847(3) | 6754(3) | 12876(6) | 72(2) |
| C(71) | 5325(4) | 6482(3) | 12490(7) | 95(3) |
| C(72) | 4752(4) | 6633(4) | 12595(7) | 100(3) |
| C(73) | 4721(6) | 7091(4) | 12195(9) | 135(4) |
| C(74) | 4301(5) | 6345(7) | 12259(12) | 174(7) |
| C(75) | 7464(3) | 7874(2) | 12165(4) | 49(1) |
| C(76) | 8000(3) | 7660(2) | 12596(4) | 50(1) |
| C(77) | 8409(3) | 7997(2) | 13104(5) | 54(1) |
| C(78) | 8696(3) | 8341(2) | 12393(5) | 66(2) |
| C(79) | 8864(3) | 7718(3) | 13668(7) | 89(3) |
| C(80) | 7868(2) | 6439(1) | 11068(3) | 27(1) |
| C(81) | 8128(2) | 6080(1) | 11742(3) | 34(1) |
| C(82) | 8581(2) | 6290(2) | 12429(3) | 36(1) |
| C(83) | 9073(2) | 6516(2) | 11867(4) | 50(1) |
| C(84) | 8812(2) | 5905(2) | 13095(4) | 49(1) |
| O(16) | 6741(2) | 7354(1) | 13432(3) | 56(1) |
| O(17) | 7214(2) | 6461(1) | 13049(2) | 46(1) |
| O(18) | 7471(1) | 7341(1) | 10200(2) | 35(1) |
| O(19) | 6045(2) | 7027(1) | 11291(3) | 55(1) |
| O(20) | 8024(1) | 6460(1) | 10215(2) | 31(1) |
| O(21) | 6520(2) | 3179(1) | 10191(3) | 50(1) |
| O(22) | 9560(4) | 5349(3) | 10090(10) | 96(4) |
| K(1) | 8740(1) | 5960(1) | 9107(1) | 32(1) |
| K(2) | 7682(1) | 3139(1) | 10764(1) | 32(1) |
| K(3) | 7153(1) | 6676(1) | 8756(1) | 28(1) |
| K(4) | 6484(1) | 2234(1) | 10709(1) | 33(1). |

4. A pharmaceutical composition comprising the potassium salt of claim 1 and a pharmaceutically acceptable carrier.

5. A method of treating a condition responsive to PPARγ modulation in a subject in need thereof comprising administering to the subject a therapeutically effective amount of a pharmaceutical composition comprising (+)-(4S,5R)-3,4-dihydroxy-2-(3-methylbutanoyl)-5-(3-methylbutyl)-4-(4-methylpentanoyl)cyclopent-2-en-1-one having the structure:

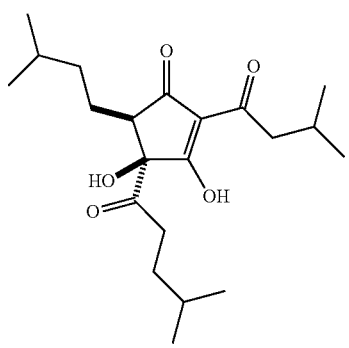 [SMILES: CC(C)CCC(=O)[C@@]1(O)C(O)=C(C(=O)CC(C)C)C(=O)[C@@H]1CCC(C)C]

or a salt or crystal thereof and a pharmaceutically acceptable carrier.

6. A method of treating a condition responsive to GPR120 modulation in a subject in need thereof comprising administering to the subject a therapeutically effective amount of a pharmaceutical composition comprising (+)-(4S,5R)-3,4-dihydroxy-2-(3-methylbutanoyl)-5-(3-methylbutyl)-4-(4-methylpentanoyl)cyclopent-2-en-1-one having the structure:

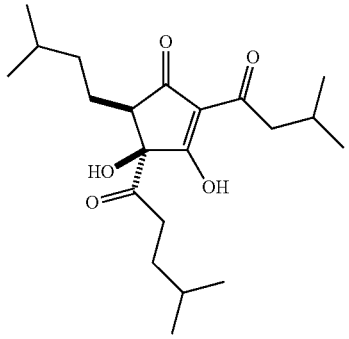 [SMILES: CC(C)CCC(=O)[C@@]1(O)C(O)=C(C(=O)CC(C)C)C(=O)[C@@H]1CCC(C)C]

or a salt or crystal thereof and a pharmaceutically acceptable carrier.

7. A method of treating a metabolic disturbance in a subject in need thereof comprising administering to the subject a therapeutically effective amount of a pharmaceutical composition comprising (+)-(4S,5R)-3,4-dihydroxy-2-(3-methylbutanoyl-5-(3-methylbutyl)-4-(4-methylpentanoyl)cyclopent-2-en-1-one having the structure:

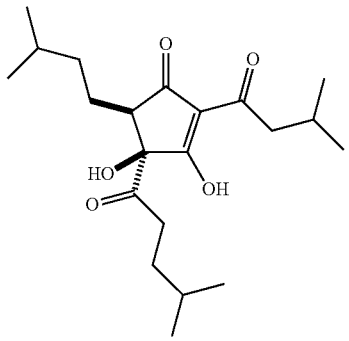 [SMILES: CC(C)CCC(=O)[C@@]1(O)C(O)=C(C(=O)CC(C)C)C(=O)[C@@H]1CCC(C)C]

or a salt or crystal thereof and a pharmaceutically acceptable carrier.

8. Crystalline (+)-(4S,5R)-3,4-dihydroxy-2-(3-methylbutanoyl)-5-(3-methylbutyl)-4-(4-methylpentanoyl)cyclopent-2-en-1-one potassium salt (1:1).

9. Crystalline (−)-(4R,5S)-3,4-dihydroxy-2-(3-methylbutanoyl)-5-(3-methylbutyl)-4-(4-methylpentanoyl)cyclopent-2-en-1-one potassium salt (1:1).

10. A method of treating a condition responsive to PPARγ modulation in a subject in need thereof comprising administering to the subject a therapeutically effective amount of a substantially enantiomerically pure composition of (+)-(4S,5R)-3,4-dihydroxy-2-(3-methylbutanoyl)-5-(3-methylbutyl)-4-(4-methylpentanoyl)cyclopent-2-en-1-one having the structure:

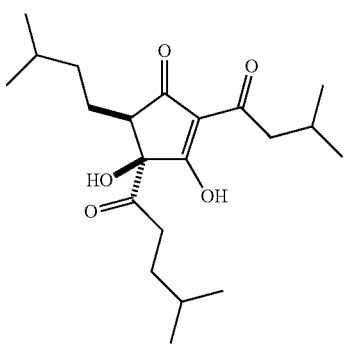 [SMILES: CC(C)CCC(=O)[C@@]1(O)C(O)=C(C(=O)CC(C)C)C(=O)[C@@H]1CCC(C)C]

or a salt or crystal thereof.

11. A method of treating a condition responsive to GPR120 modulation in a subject in need thereof comprising administering to the subject a therapeutically effective amount of a substantially enantiomerically pure composition of (+)-(4S,5R)-3,4-dihydroxy-2-(3-methylbutanoyl)-5-(3-methylbutyl)-4-(4-methylpentanoyl)cyclopent-2-en-1-one having the structure:

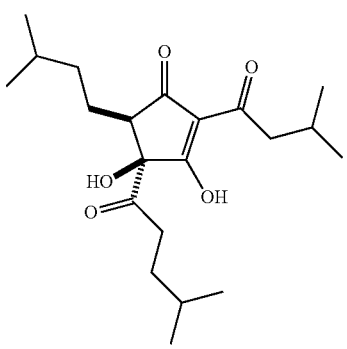 [SMILES: CC(C)CCC(=O)[C@@]1(O)C(O)=C(C(=O)CC(C)C)C(=O)[C@@H]1CCC(C)C]

or a salt or crystal thereof.

12. A method of treating a metabolic disturbance in a subject in need thereof comprising administering to the subject a therapeutically effective amount of a substantially enantiomerically pure composition of (+)-(4S,5R)-3,4-dihydroxy-2-(3-methylbutanoyl)-5-(3-methylbutyl)-4-(4-methylpentanoyl)cyclopent-2-en-1-one having the structure:

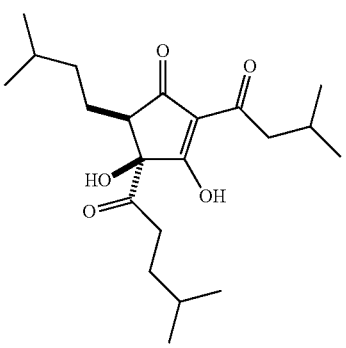 [SMILES: CC(C)CCC(=O)[C@@]1(O)C(O)=C(C(=O)CC(C)C)C(=O)[C@@H]1CCC(C)C]

or a salt or crystal thereof.

13. The method of claim 5, 6, 7, 10, 11, or 12, wherein the salt thereof is a potassium salt having the structure:

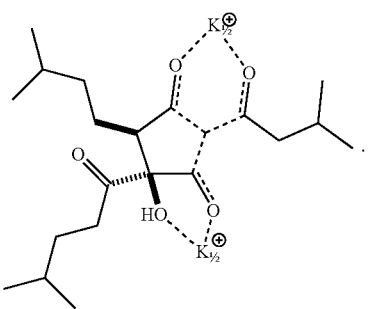

14. The method of claim 10, 11, or 12, wherein the composition further comprises a pharmaceutically acceptable carrier.

15. The method of claim 5 or 10, wherein the condition is selected from the group consisting of diabetes and obesity.

16. The method of claim 7 or 12, wherein the metabolic disturbance is diabetes.

17. The method of claim 7 or 12, wherein administration of the pharmaceutical composition results in a decrease in glucose and/or lipid levels.

\* \* \* \* \*

UNITED STATES PATENT AND TRADEMARK OFFICE
CERTIFICATE OF CORRECTION

PATENT NO. : 8,410,178 B2
APPLICATION NO. : 13/284852
DATED : April 2, 2013
INVENTOR(S) : Brian J. Carroll et al.

It is certified that error appears in the above-identified patent and that said Letters Patent is hereby corrected as shown below:

In the Claims

Claim 17, column 54, line 42, delete "pharmaceutical" between "the" and "composition".

Signed and Sealed this
Twenty-first Day of May, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,410,178 B2
APPLICATION NO. : 13/284852
DATED : April 2, 2013
INVENTOR(S) : Brian J. Carroll et al.

It is certified that error appears in the above-identified patent and that said Letters Patent is hereby corrected as shown below:

On the Title Page, item (54) and in the specification, column 1, line 4, Title, insert --ONE-- between "-2-EN-1-" and "DERIVATIVES".

Signed and Sealed this
Fifteenth Day of October, 2013

Teresa Stanek Rea
*Deputy Director of the United States Patent and Trademark Office*